United States Patent
Bischof et al.

(10) Patent No.: US 11,859,025 B2
(45) Date of Patent: *Jan. 2, 2024

(54) OLIGOMERIZATION CATALYST SYSTEM ACTIVATION AND RELATED ETHYLENE OLIGOMERIZATION PROCESSES AND REACTION SYSTEMS

(71) Applicant: Chevron Phillips Chemical Company LP, The Woodlands, TX (US)

(72) Inventors: Steven M. Bischof, Humble, TX (US); James L. Hillier, Kingwood, TX (US); Uriah J. Kilgore, Kingwood, TX (US); Steve R. Hutchison, Spring, TX (US); Bruce E. Kreischer, Humble, TX (US); Orson L. Sydora, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 156 days.

This patent is subject to a terminal disclaimer.

(21) Appl. No.: 17/467,505

(22) Filed: Sep. 7, 2021

(65) Prior Publication Data
US 2022/0025081 A1 Jan. 27, 2022

Related U.S. Application Data

(63) Continuation of application No. 16/929,204, filed on Jul. 15, 2020, now Pat. No. 11,267,909.

(51) Int. Cl.
*C08F 4/69* (2006.01)
*C08F 2/00* (2006.01)
(Continued)

(52) U.S. Cl.
CPC ............... *C08F 10/02* (2013.01); *C07C 2/36* (2013.01); *B01J 31/143* (2013.01); *B01J 31/189* (2013.01);
(Continued)

(58) Field of Classification Search
CPC ...... C08F 2/01; C08F 4/78; C08F 4/69; C08F 4/69068
See application file for complete search history.

(56) References Cited

U.S. PATENT DOCUMENTS 5,689,012 A * 11/1997 Pazos ................ C08G 65/2663
568/619
5,910,619 A 6/1999 Urata
(Continued)

FOREIGN PATENT DOCUMENTS

WO 2010051415 A1 5/2010
WO 2013116922 A1 8/2013

OTHER PUBLICATIONS

Agapie, et al. "Mechanistic Studies of Olefin and Alkyne Trimerization with Chromium Catalysts: Deuterium Labeling and Studies of Regiochemistry Using a Model Chromacyclopentane Complex." Journal of the American Chemical Society. 2007. 129. pp. 14281-14295.

(Continued)

*Primary Examiner* — Rip A Lee
(74) *Attorney, Agent, or Firm* — Merchant & Gould P.C.

(57) ABSTRACT

Disclosed herein are oligomerization processes in which ethylene and a catalyst system are first combined for a suitable residence time in an activation vessel, prior to introduction into a reaction zone to oligomerize ethylene to form a desired oligomer product, such as 1-hexene and/or 1-octene. Related oligomerization reaction systems that include the activation vessel also are disclosed. In these oligomerization processes and reaction systems, the catalyst system can be fully activated as it leaves the activation vessel and enters the reaction zone, thus providing greater catalyst utilization and less catalyst waste.

21 Claims, 6 Drawing Sheets

(51) Int. Cl.
*C08F 10/02* (2006.01)
*C07C 2/36* (2006.01)
*B01J 31/14* (2006.01)
*B01J 31/18* (2006.01)
*B01J 31/24* (2006.01)

(52) U.S. Cl.
CPC ........ *B01J 31/2438* (2013.01); *B01J 2231/20* (2013.01); *B01J 2531/62* (2013.01); *C07C 2531/14* (2013.01); *C07C 2531/24* (2013.01); *C08F 4/69* (2013.01); *C08F 4/69068* (2013.01)

(56) References Cited

U.S. PATENT DOCUMENTS

| | | |
|---|---|---|
| 7,300,904 B2 | 11/2007 | Dixon |
| 7,361,623 B2 | 4/2008 | Dixon |
| 7,554,001 B2 | 6/2009 | Dixon |
| 7,994,363 B2 | 8/2011 | Gao |
| 8,252,956 B2 | 8/2012 | Gao |
| 8,680,003 B2 | 3/2014 | Sydora |
| 8,865,610 B2 | 10/2014 | Sydora |
| 10,414,699 B2 | 9/2019 | Bischof |
| 10,435,336 B2 | 10/2019 | Kreischer |
| 10,689,312 B2 | 6/2020 | Bischof |
| 11,267,909 B2 * | 3/2022 | Bischof ............... C08F 10/02 |
| 2010/0222622 A1 | 9/2010 | Overett |
| 2010/0274065 A1 | 10/2010 | Sydora |
| 2012/0309965 A1 | 12/2012 | Sydora |
| 2013/0331629 A1 | 12/2013 | Sydora |
| 2016/0375431 A1 | 12/2016 | Carney |
| 2017/0081257 A1 | 3/2017 | Kreischer |
| 2017/0341998 A1 | 11/2017 | Bischof |
| 2017/0341999 A1 | 11/2017 | Fern |
| 2017/0342000 A1 | 11/2017 | Bischof |
| 2017/0342001 A1 | 11/2017 | Fern |
| 2019/0092709 A1 | 3/2019 | Bischof |

OTHER PUBLICATIONS

Bollmann, et al. "Ethylene Tetramerization: A New Route to Produce 1-Octene in Exceptionally High Selectivities." J. Am. Chem. Soc. 2004, 126. pp. 14712-14713.

Carter, et al. "High activity ethylene trimerisation catalysts based on diphosphine ligands" Chemical Communications. 2002. pp. 858-859.

Kappler, et al. "Real-Time Monitoring of Ethene/1-Hexene Copolymerizations: Determination of Catalyst Activity, Copolymer Composition and Copolymerization Parameters." Polymer, 2003, 44, 6179-6186.

Sydora, et al. "Selective Ethylene Tri-/Tetramerization Catalysts." ACS Catalysis. 2012. 2. 2452.

International Search Report and Written Opinion for PCT/2021/041726 dated Jan. 20, 2022. pp. 1-9.

Rucklidge, Adam et al. "Ethylene Tetramerization with Cationic Chromium(I) Complexes." Organometallics. vol. 26, No. 10. May 1, 2007. pp. 2782-2787.

* cited by examiner

OLIGOMERIZATION CATALYST SYSTEM ACTIVATION AND RELATED ETHYLENE OLIGOMERIZATION PROCESSES AND REACTION SYSTEMS

REFERENCE TO RELATED APPLICATION

This application is a continuation application of co-pending U.S. patent application Ser. No. 16/929,204, filed on Jul. 15, 2020, now U.S. Pat. No. 11,267,909, the disclosure of which is incorporated herein by reference in its entirety.

FIELD OF THE INVENTION

This disclosure relates generally to ethylene oligomerization processes and related oligomerization reaction systems, and more particularly, relates to the use of an activation vessel to activate a chromium-based catalyst system prior to its introduction into an ethylene oligomerization reaction zone.

BACKGROUND OF THE INVENTION

Chromium-based catalyst systems often are used for the oligomerization of ethylene to produce hexenes and/or octenes. However, the preparation and treatment of the catalyst system before it enters an oligomerization reaction zone can lead to different catalyst productivities, overall catalyst usage rates, and/or active catalyst residence times. It would be beneficial to produce hexenes and/or octenes from ethylene using a process and reaction system in which the catalyst efficiency, catalyst productivity, and/or active catalyst residence times are improved. Accordingly, it is to these ends that the present disclosure is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Disclosed herein are ethylene oligomerization processes, and in one aspect, such processes can comprise a) forming a first mixture in an activation vessel, the first mixture comprising ethylene, a catalyst system comprising i) a heteroatomic ligand chromium compound complex and an organoaluminum compound, or ii) a heteroatomic ligand, a chromium compound, and an organoaluminum compound, optionally, a first organic reaction medium, and optionally, hydrogen; b) maintaining the first mixture in the activation vessel for an average residence time; c) introducing into a reaction zone: ethylene, the first mixture from step b), a second organic reaction medium, and optionally, hydrogen; and forming an oligomer product in the reaction zone.

Another process consistent with this disclosure can comprise a) forming a first mixture in an activation vessel, the first mixture comprising 1) a first catalyst system comprising i) a first heteroatomic ligand chromium compound complex and a first organoaluminum compound, or ii) a first heteroatomic ligand, a first chromium compound, and a first organoaluminum compound, 2) a first feed comprising ethylene, a second catalyst system comprising i) a second heteroatomic ligand chromium compound complex, and a second organoaluminum compound, or ii) a second heteroatomic ligand, a second chromium compound and a second organoaluminum compound, a second organic reaction medium, a second oligomer product, and optionally hydrogen, 3) optionally, a first organic reaction medium, and 4) optionally, hydrogen; b) maintaining the first mixture in the activation vessel for an average residence time; c) introducing into a reaction zone: ethylene, the first mixture from step b), the second organic reaction medium, and optionally, hydrogen; and d) forming an oligomer product in the reaction zone. A portion of a reaction zone effluent is fed to the activation vessel as the first feed.

Other aspects of this disclosure are directed to reaction systems, and such systems can comprise (a) an activation vessel configured to form a first mixture, wherein the activation vessel is further configured for an average residence time of the first mixture in the activation vessel; (b) one or more activation vessel inlets configured to introduce i) ethylene and a catalyst system mixture, or ii) ethylene and components of a catalyst system mixture, into the activation vessel; (c) an activation vessel outlet configured to withdraw the first mixture from the activation vessel; (d) a reaction zone configured to contact ethylene, the first mixture, a second organic reaction medium, and optionally hydrogen to form an oligomer product; (e) one or more reaction zone inlets configured to introduce ethylene, the second organic reaction medium, and the first mixture from the activation vessel outlet into the reaction zone; and (f) a reaction zone outlet configured to withdraw a reaction zone effluent stream containing the oligomer product from the reaction zone.

In these oligomerization processes and reaction systems, the average residence time of the first mixture in the activation vessel can be in a range from 10 sec up to a period of time sufficient to form an amount of a first oligomer product in the activation vessel equal to 5% of an amount of the oligomer product formed in the reaction zone; or a conversion of ethylene in the activation vessel can be less than or equal to 5 mol % of a total ethylene utilized in step a) and step c); or a catalyst system productivity in the activation vessel can be less than or equal to 5% of a catalyst system mixture productivity in the reaction zone; or a fouling rate in the activation vessel can be less than or equal to 0.065 mg/cm$^2$-hr; or an oligomer product discharge rate from the activation vessel can be less than or equal to 0.15 lb/gal/hr, and an oligomer product discharge rate from the reaction zone can be in a range from 0.75 to 6 lb/gal/hr; or a $\Delta$T from the inlet of the activation vessel to the outlet of the activation vessel can be less than or equal to 5° C.; or up to a maximum of 8 hr. In these oligomerization processes and reaction systems, an amount of ethylene introduced into the activation vessel can be less than 50% of an amount of ethylene introduced into the reaction zone; or step b) can be performed at an activation temperature and an activation pressure, and the first mixture in the activation vessel can be below the bubble point at the activation temperature and the activation pressure. In an aspect, the average residence time can be in any suitable range or any range disclosed herein, e.g., from 10 sec, 30 sec, 1 min, or 2 min to any period of time, or any combination of periods of time and these features disclosed herein.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURES

The accompanying drawings, which are incorporated in and constitute a part of this disclosure, illustrate various aspects of the present disclosure. In the drawings.

DEFINITIONS

Figure 1:
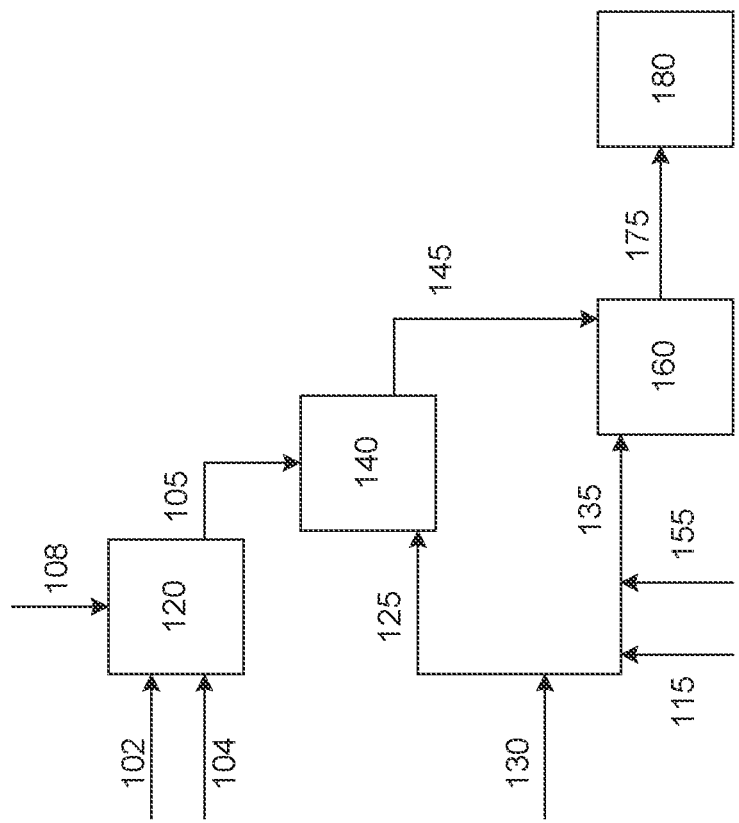
FIG. 1 illustrates an oligomerization reaction system consistent with an aspect of the present disclosure.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects and/or statements, a combination of different features can be envisioned. For each and every aspect, and/or statement, and/or feature disclosed herein, all combinations that do not detrimentally affect the systems, compositions, processes, and/or methods described herein are contemplated with or without explicit description of the particular combination. Additionally, unless explicitly recited otherwise, any aspect, and/or statement, and/or feature disclosed herein can be combined to describe conceived processes and systems consistent with the present disclosure.

The terms "a," "an," and "the" are intended to include plural alternatives, e.g., at least one, unless otherwise specified. For instance, the disclosure of "an organoaluminum compound" is meant to encompass one, or combinations of more than one, organoaluminum compound, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

A chemical "group" is described according to how that group is formally derived from a reference or "parent" compound, for example, by the number of hydrogen atoms formally removed from the parent compound to generate the group, even if that group is not literally synthesized in this manner By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout, the disclosure of a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. An "organyl group," "organylene group," or "organic group" can be aliphatic, (inclusive of being cyclic or acyclic, or linear or branched), or can be aromatic.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the processes described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group can be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), and/or sulfidyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl groups are derived by removal of a hydrogen atom from a primary, secondary, or tertiary carbon atom, respectively, of an alkane. The n-alkyl group can be derived by removal of a hydrogen atom from a terminal carbon atom of a linear alkane.

The term "substituted" when used to describe a compound or group, for example, when referring to a substituted analog of a particular compound or group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alkene" whenever used in this specification and claims refers to a linear or branched aliphatic hydrocarbon olefin that has one or more carbon-carbon double bonds. Alkenes having only one, only two, only three, etc., such multiple bonds can be identified by use of the term "mono," "di," "tri," etc., within the name. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atoms of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of other carbon-carbon double bonds unless explicitly indicated.

The term "normal alpha olefin" whenever used in this specification and claims refers to a linear aliphatic mono-olefin having a carbon-carbon double bond between the first and second carbon atoms. It is noted that "normal alpha olefin" is not synonymous with "linear alpha olefin" as the term "linear alpha olefin" can include linear olefinic compounds having a double bond between the first and second carbon atoms and additional double bonds.

The term "reaction zone effluent," and it derivatives (e.g., oligomerization reaction zone effluent, trimerization reaction zone effluent, tetramerization reaction zone effluent, or trimerization and tetramerization reaction zone effluent) generally refers to all the material which exits the reaction zone through a reaction zone outlet/discharge which discharges a reaction mixture and can include reaction zone feed(s) (e.g., olefin, catalyst system or catalyst system components, and/or solvent), and/or reaction product (e.g., oligomer product including oligomers and non-oligomers, trimerization product including trimer and non-trimer, tetramerization product including tetramer and non-tetramer, or trimerization and tetramerization product including trimer and tetramer and non-trimer and tetramer). The term "reaction zone effluent" and its derivatives can be qualified to refer to certain portions by use of additional qualifying terms. For example, while reaction zone effluent refers to all material which exits the reaction zone through the reaction zone outlet/discharge, a reaction zone oligomer product effluent refers to only the oligomer product within the reaction zone effluent.

The terms "room temperature" or "ambient temperature" are used herein to describe any temperature from 15° C. to 35° C. wherein no external heat or cooling source is directly applied to the reaction vessel. Accordingly, the terms "room temperature" and "ambient temperature" encompass the individual temperatures and any and all ranges, subranges, and combinations of subranges of temperatures from 15° C. to 35° C. wherein no external heating or cooling source is directly applied to the reaction vessel. The term "atmospheric pressure" is used herein to describe an earth air pressure wherein no external pressure modifying means is utilized. Generally, unless practiced at extreme earth altitudes, "atmospheric pressure" is about 1 atmosphere (alternatively, about 14.7 psi or about 101 kPa).

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Within this disclosure, the normal rules of organic nomenclature prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4-position and hydrogens located at the 2, 3, 5, and 6 positions. References to compounds or groups having substitutions at positions in addition to the indicated position can be referenced using comprising or some other alternative language. For example, a reference to a phenyl group comprising a substituent at the 4-position refers to a phenyl group having a non-hydrogen substituent at the 4-position and hydrogen or any non-hydrogen substituent at the 2, 3, 5, and 6 positions.

The terms "catalyst composition," "catalyst mixture," "catalyst system," and the like, do not depend upon the actual product or composition resulting from the contact or reaction of the initial components of the disclosed or claimed catalyst composition/mixture/system, the nature of the active catalytic site, or the fate of the organoaluminum compound and the heteroatomic ligand chromium compound complex after combining these components. Therefore, the terms "catalyst composition," "catalyst mixture," "catalyst system," and the like, encompass the initial starting components of the composition, as well as whatever product(s) may result from contacting these initial starting components. The terms "catalyst composition," "catalyst mixture," "catalyst system," and the like, may be used interchangeably throughout this disclosure.

The term oligomer refers to a product that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer).

The term "oligomerization," and its derivatives, refers to processes which produce an oligomer product comprising at least 20 wt. %, 35 wt. %, 50 wt. %, or 60 wt. % products comprising from 2 to 20 monomer units. In an example, an "oligomerization" process using ethylene as the monomer produces a mixture of products comprising at least 20 wt. %, 35 wt. %, 50 wt. %, or 60 wt. % oligomers having from 4 to 40 carbon atoms.

The term "trimerization," and its derivatives, refers to a process which produces a mixture of products comprising at least 20 wt. %, 35 wt. %, 50 wt. %, or 60 wt. % products comprising three and only three monomer units. A "trimer" is a product which comprises three and only three monomer units. A "trimerization product" includes all products made by the trimerization process including trimer and products which are not trimer (e.g., dimers or tetramers, solid polymer). In an example, a "trimerization" process using ethylene as the monomer produces a mixture of products comprising at least 20 wt. %, 35 wt. %, 50 wt. %, or 60 wt. % hexenes.

The term "tetramerization," and its derivatives, refers to a process which produces a mixture of products comprising at least 20 wt. %, 35 wt. %, 50 wt. %, or 60 wt. % products comprising four and only four monomer units. A "tetramer" is a product which comprises four and only four monomer units. A "tetramerization product" includes all products made by the tetramerization process including tetramer and products which are not tetramer (e.g., dimers or trimers, solid polymer). In an example, a "tetramerization" process using ethylene as the monomer produces a mixture of products comprising at least 20 wt. %, 35 wt. %, 50 wt. %, or 60 wt. % octenes.

The term "trimerization and tetramerization," and its derivatives, refers to a process which produces a mixture of products comprising at least 20 wt. %, 35 wt. %, 50 wt. %, or 60 wt. % products comprising three and/or four and only three and/or four monomer units. A "trimerization and tetramerization product" includes all products made by the "trimerization and tetramerization" process including trimer, tetramer, and products which are not trimer and tetramer (e.g., dimers, solid polymer). In an example, a "trimerization and tetramerization" process using ethylene as the monomer produces a mixture of products comprising at least 20 wt. %, 35 wt. %, 50 wt. %, or 60 wt. % hexenes and octenes.

Within this specification, the word "reactor" refers to a single piece of equipment, such as, for example, a vessel, in which a reaction takes place, but excludes any associated equipment such as piping, pumps, and the like which is external to the vessel. Examples of reactors include stirred tank reactors (e.g., a continuous stirred tank reactor), plug flow reactors, or any other type of reactor.

Within this specification, term "reaction zone" refers to the portion of a reaction system where all the necessary reaction components and reaction conditions are present such that the reaction can occur at a desired rate. That is to say that the reaction zone begins where the necessary reaction components and reaction conditions are present to maintain the reaction within 25 percent of the average reaction rate and the reaction system ends where the conditions do not maintain a reaction rate within 25 percent of the average reaction rate (based upon a volume average of the reaction rate of the reaction zone). For example, in terms of an ethylene oligomerization process, the reaction zone begins at the point where sufficient ethylene and active catalyst system is present under the sufficient reaction conditions (e.g., temperature and/or pressure, among others) to maintain oligomer product production at the desired rate and the reaction zone ends at a point where either the catalyst system is deactivated, sufficient ethylene is not present to sustain oligomer product production, or other reaction conditions (e.g., temperature and/or pressure, among others) are not sufficient to maintain the oligomer product production or the desired oligomer product production rate. Within this specification the "reaction zone" can comprise one or more reactors. The term "reaction zone" can be qualified to refer to more specific "reaction zones" by use of additional qualifying terms. For example, the use of the term "oligomerization reaction zone" indicates that the desired reaction within the "reaction zone" is an oligomerization.

The term "reaction system" refers to all of the equipment to produce a product. The term "reaction system" includes reactors, reaction zones, and all the associated equipment, associated process lines, and control equipment which can bring the necessary component(s) into and out of the reaction system and control the reaction. Within this specification the "reaction system" can comprise one or more reactor zones, one or more reactors, and associated equipment to produce a product. The term "reaction system" can be qualified to refer to more specific "reaction systems" by use of additional qualifying terms. For example, the use of the term "oligomerization reaction system" indicates that the "reaction system" relates to an oligomerization.

Catalyst system productivity is defined herein in units of kilograms of a normal alpha olefin product produced per gram of chromium of the heteroatomic ligand chromium compound complex (or chromium compound) utilized in the catalyst system per hour—kg NAO/g Cr/hr.

Although any methods and materials similar or equivalent to those described herein can be used in the practice or testing of the processes and reaction systems, the typical methods and materials are herein described.

All publications and patents mentioned herein are incorporated herein by reference for the purpose of describing and disclosing, for example, the constructs and methodologies that are described in the publications, which might be used in connection with the present disclosure.

DETAILED DESCRIPTION OF THE INVENTION

Disclosed herein are ethylene oligomerization reaction systems and ethylene oligomerization processes that utilize a homogeneous chromium-based catalyst system to produce various oligomer products, such as 1-hexene and/or 1-octene. In these oligomerization reaction systems and oligomerization processes, an activation vessel is employed to activate the catalyst system and to improve catalyst productivity and efficiency in the oligomerization reaction zone.

Incomplete catalyst activation can often lead to a variety of negative effects in the reaction zone, including the co-generation of by-products such as cyclopentane/cyclopentanes, mixed C10s, C12s, and C14s, and solid polyethylene/polymer. In particular, the formation of polymer leads to reactor wall fouling that can cause reduced run time, loss of heat transfer for cooling the exothermic reaction, and poor overall reactor performance. Therefore, reducing or eliminating the formation of polymer is important for any ethylene oligomerization process and oligomerization reaction system. This is even more important if reactor temperatures are below the melting temperature of the polymers and/or wax products that are being generated.

Catalyst system activation of many chromium-based complexes with an organoaluminum compound, such as MAO, is not instantaneous. While not being bound by theory, it is believed that there can be an induction period for the catalyst system, after contact with ethylene, and before the catalyst system reaches it full catalytic activity. This induction period can be very brief (e.g., less than 5 sec), or it can range from 1-5 min to 20-30 min, to 1-2 hr, to 4 hr, or more. It is further believed that activating the catalyst system directly in the oligomerization reactor in the presence of ethylene reduces overall catalyst system performance and leads to inefficient use of the catalyst system components.

As disclosed herein, activating the catalyst system in an activation vessel under a controlled set of conditions for a specified residence time that can eliminate some or all of the induction period in the oligomerization reaction zone can improve overall catalyst system performance and/or oligomer product discharge rate. Operating at a residence time that is substantially the same as the induction time of the particular catalyst system (and such that minimal to no ethylene oligomerization occurs in the activation vessel) can ensure that the catalyst system is at peak activity and efficiency (such as observed by oligomer product discharge rate) as it enters the oligomerization reaction zone. Thus, the total active catalytic species present in the oligomerization reaction zone is maximized, resulting in improved overall catalyst system productivity and improved catalyst system component usage (and reduced waste).

Catalyst Systems

The processes and reaction systems disclosed herein can utilize a catalyst system (or catalyst system mixture) comprising i) a heteroatomic ligand chromium compound complex and an organoaluminum compound or ii) a heteroatomic ligand, a chromium compound, and an organoaluminum compound; alternatively, a heteroatomic ligand chromium compound complex and an organoaluminum compound; or alternatively, a heteroatomic ligand, a chromium compound, and an organoaluminum compound. In an aspect, the catalyst system (or catalyst system mixture) can further comprise (optionally) a catalyst system organic medium. In some aspects, the catalyst system (or catalyst system mixture) comprising i) a heteroatomic ligand chromium compound complex and an organoaluminum compound or ii) a heteroatomic ligand, a chromium compound, and an organoaluminum compound) can be introduced into the reaction mixture within the reaction zone. In other aspects, at least one of i) a heteroatomic ligand chromium compound complex and an organoaluminum compound or ii) a heteroatomic ligand, a chromium compound, and an organoaluminum compound can be separately introduced into a mixture in an activation vessel from other components of the catalyst system (or catalyst system mixture). The heteroatomic ligand, the chromium compound, the heteroatomic ligand chromium compound complex, the heteroatomic ligand of the heteroatomic ligand chromium compound complex, the chromium compound of the heteroatomic ligand chromium compound, the organoaluminum compound, and the optional catalyst system organic medium are independent elements of the processes and reaction systems described herein and are independently described herein. These independently described catalyst system (or catalyst system mixture) elements can be utilized in any combination, and without limitation, to further describe the processes and reaction systems provided herein.

Non-limiting examples of suitable catalyst system organic mediums include hydrocarbons, such as aromatic hydrocarbons. Suitable aromatic hydrocarbons can include isolated refinery aromatic streams containing mixtures comprising aromatic hydrocarbons (e.g., aromatic streams comprising $C_8$ and $C_9$ aromatic hydrocarbons like Total Atosol 100, ExxonMobil A100, and Shell Solv100, or other streams containing xylenes, cumene, or ethylbenzene, among others). Alternatively, suitable aromatic hydrocarbons can include predominately single carbon number aromatic hydrocarbon compound streams (e.g., benzene, toluene, xylenes, cumene, or ethylbenzene). Aromatic hydrocarbons that can be utilized singly or in any combination include benzene, toluene, xylene (including ortho-xylene, meta-xylene, para-xylene, or mixtures thereof), cumene, and ethylbenzene, or combinations thereof; alternatively, benzene; alternatively, toluene; alternatively, xylene (including ortho-xylene, meta-xylene, para-xylene or mixtures thereof); alternatively, cumene; or alternatively, ethylbenzene. In a particular aspect of this disclosure, the catalyst system organic medium can comprise, or consist essentially of, or consist of, ethylbenzene.

Generally, the heteroatomic ligand or the heteroatomic ligand of the heteroatomic ligand chromium compound complex can be any heteroatomic ligand, which when utilized in the catalyst systems (or catalyst system mixtures) described herein for the processes and/or reaction systems described herein, can form an oligomer product in the reaction zone. In an aspect, the heteroatomic ligand or the heteroatomic ligand of the heteroatomic ligand chromium compound complex can be a neutral heteroatomic ligand or an anionic heteroatomic ligand; alternatively, a neutral heteroatomic ligand; or alternatively, an anionic heteroatomic ligand. In an aspect, the neutral heteroatomic ligand can comprise one or more heteroatomic complexing moieties; alternatively, two heteroatomic complexing; or alternatively, three heteroatomic complexing moieties. In an aspect, the anionic heteroatomic ligand can also comprise one or more neutral heteroatomic complexing moieties; alternatively, two heteroatomic complexing; or alternatively, three heteroatomic complexing moieties. In an aspect, the each neutral heteroatomic complexing moiety of the neutral ligand or the anionic ligand comprising a neutral heteroatomic complexing moiety independently can be an ether group, a sulfide group, an amine group, an imine group, a phosphine group, a phosphinite group, a phosphonite group, or a phosphite group; alternatively, an ether group, a sulfide group, an amine group, an imine group, or a phosphine group; alternatively, an ether group; alternatively, a sulfide group; alternatively, an amine group; alternatively, an imine group; or alternatively, a phosphine group. In an aspect, the anion atom of the anionic heteroatomic ligand (which forms a covalent or ionic bond with the chromium of the chromium compound) can be an anionic carbon atom, an anionic oxygen atom, or an anion nitrogen atom; alternatively, an anionic carbon atom; alternatively, an anionic oxygen atom; or alternatively, an anion nitrogen atom.

In any aspect, the heteroatomic ligand or the heteroatomic ligand of the heteroatomic ligand chromium compound complex can comprise, can consist essentially of, or can be, an $N^2$-phosphinyl formamidine, an $N^2$-phosphinyl amidine, an $N^2$-phosphinyl guanidine, a heterocyclic 2-[(phosphinyl) aminyl]imine, or any combination thereof; alternatively, an $N^2$-phosphinyl formamidine; alternatively, an $N^2$-phosphinyl amidine; alternatively, an $N^2$-phosphinyl guanidine; or alternatively, a heterocyclic 2-[(phosphinyl)aminyl]imine Generally, the an $N^2$-phosphinyl formamidine can have Structure NPF1, the $N^2$-phosphinyl amidine can have Structure NPA1, the $N^2$-phosphinyl guanidine can have Structure Gu1, Structure Gu2, Structure Gu3, Structure Gu4, or Structure Gu5, and the heterocyclic 2-[(phosphinyl)aminyl]imine can have structure HCPA1. In some aspects, the $N^2$-phosphinyl guanidine have Structure Gu2, Structure Gu3, or Structure Gu4; alternatively, Structure Gu1; alternatively, Structure Gu2; alternatively, Structure Gu3; alternatively, Structure Gu4; or alternatively Structure Gu5.

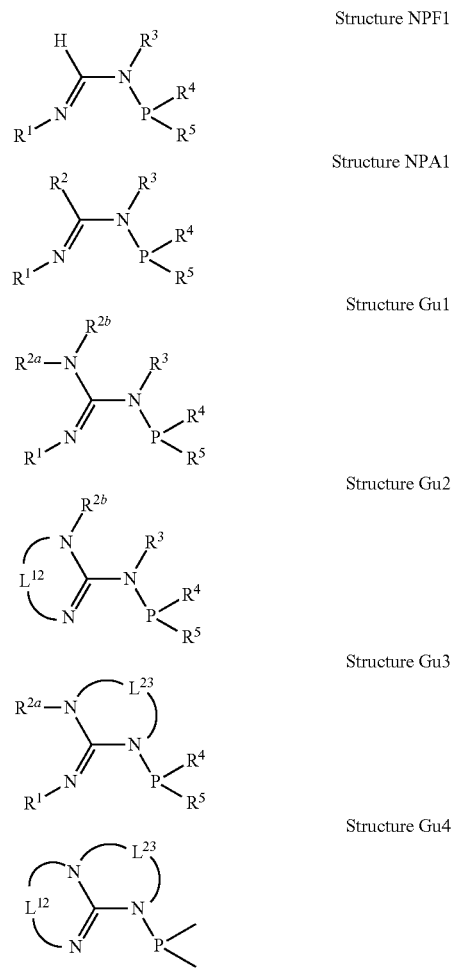

-continued

Structure Gu5
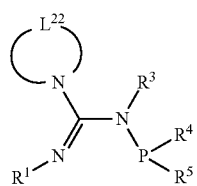

Structure HCPA1
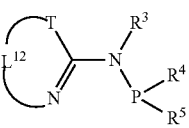

In any aspect, the heteroatomic ligand chromium compound complex can comprise, can consist essentially of, or can be, an $N^2$-phosphinyl formamidine chromium compound complex, an $N^2$-phosphinyl amidine chromium compound complex, an $N^2$-phosphinyl guanidine chromium compound complex, a heterocyclic 2-[(phosphinyl)aminyl]imine chromium compound complex, or any combination thereof; alternatively, an $N^2$-phosphinyl formamidine chromium compound complex; alternatively, an $N^2$-phosphinyl amidine chromium compound complex; alternatively, an $N^2$-phosphinyl guanidine chromium compound complex; alternatively, an $N^2$-phosphinyl guanidine chromium compound complex; or alternatively, a heterocyclic 2-[(phosphinyl)aminyl]imine chromium compound complex. Generally, the an $N^2$-phosphinyl formamidine chromium compound complex can have Structure NPFCr1, the $N^2$-phosphinyl amidine chromium compound complex can have Structure NPACr1, the $N^2$-phosphinyl guanidine chromium compound complex can have Structure GuCr1, Structure GuCr2, Structure GuCr3, Structure GuCr4, or Structure GuCr5, and the heterocyclic 2-[(phosphinyl)aminyl]imine chromium compound complex can have Structure HCPACr1. In some aspects, the $N^2$-phosphinyl guanidine chromium compound complex have Structure GuCr2, Structure GuCr3, or Structure GuCr4; alternatively, Structure GuCr1; alternatively, Structure GuCr2; alternatively, Structure GuCr3; alternatively, Structure GuCr4; or alternatively Structure GuCr5.

Structure NPFCr1
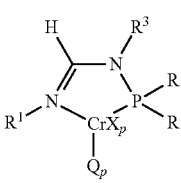

Structure NPACr1
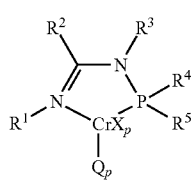

Structure GuCr1
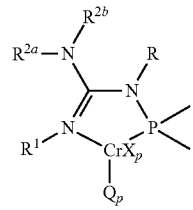

Structure GuCr2
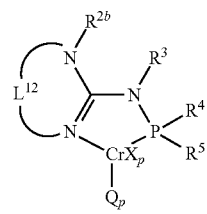

Structure GuCr3
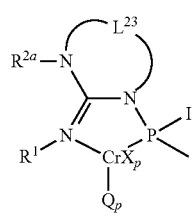

Structure GuCr4
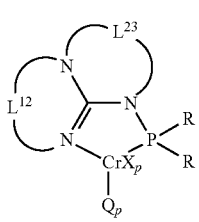

Structure GuCr5
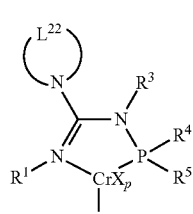

Structure HCPACr2
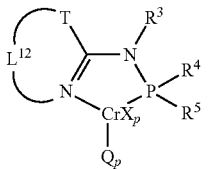

Within the $N^2$-phosphinyl formamidines, the $N^2$-phosphinyl formamidine chromium compound complexes, the $N^2$-phosphinyl amidines, the $N^2$-phosphinyl amidine chromium compound complexes, and the heterocyclic 2-[(phosphinyl)aminyl]imine chromium compound complexes the nitrogen participating in a double bond with the central carbon atom is referred to as the $N^1$ nitrogen and the nitrogen atom participating in a single bond with the central carbon atom is referred to as the $N^2$ nitrogen. Similarly, within the $N^2$-phosphinyl guanidines and the $N^2$-phosphinyl guanidine chromium compound complexes, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that the guanidine group of the guanidine in the $N^2$-phosphinyl guanidines and the $N^2$-phosphinyl guanidine chromium complexes can be a portion of a larger group which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an guanidine group) since it contains the defined general structure of the guanidine compound.

$R^1$, $R^3$, $R^4$, and $R^5$ within the $N^2$-phosphinyl formamidine structures and the $N^2$-phosphinyl formamidine chromium compound complex structures, $R^1$, $R^2$, $R^3$, $R^4$, and $R^5$ within the $N^2$-phosphinyl amidine structures and the $N^2$-phosphinyl amidine chromium compound complex structures, $R^1$, $R^{2a}$, $R^{2b}$, $R^3$, $R^4$, $R^5$, $L^{12}$, $L^{22}$, and $L^{23}$ within the $N^2$-phosphinyl guanidine structures and the $N^2$-phosphinyl guanidine chromium compound complex structures, and $L^{12}$, T, $R^3$, $R^4$, and $R^5$ within the heterocyclic 2-[(phosphinyl)aminyl]imine structures and heterocyclic 2-[(phosphinyl)aminyl]imine chromium compound complex structures are independently described herein and can be utilized in any combination and without limitation to further describe the $N^2$-phosphinyl formamidine structures, the $N^2$-phosphinyl formamidine chromium compound complex structures, the $N^2$-phosphinyl amidine structures, the $N^2$-phosphinyl amidine chromium compound complex structures, the $N^2$-phosphinyl guanidine structures, the $N^2$-phosphinyl guanidine chromium compound complex structures, the heterocyclic 2-[(phosphinyl)aminyl]imine structures, and the heterocyclic 2-[(phosphinyl)aminyl]imine chromium compound complex structures disclosed herein. $X_p$, Q, and q of the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures are independently described herein and can be utilized in any combination, and without limitation, to further describe the $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures contemplated herein. Additionally, the independent descriptions of $X_p$, Q, and q can be combined, without limitation, with the independently described $R^1$, $R^2$, $R^{2a}$, $R^{2b}$, $R^3$, $R^4$, $R^5$, $L^{12}$, $L^{22}$, and $L^{23}$ to further describe the appropriate $N^2$-phosphinyl formamidine chromium compound complex structures, the $N^2$-phosphinyl amidine chromium compound complex structures, the $N^2$-phosphinyl guanidine chromium compound complex structures, and the heterocyclic 2-[(phosphinyl)aminyl]imine chromium compound complex structures contemplated herein.

Generally, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an organyl group; alternatively, an organyl group consisting of inert functional groups; or alternatively, a hydrocarbyl group. In an aspect, the $R^1$ organyl group can be a $C_1$ to $C_{20}$, a $C_1$ to $C_{15}$, a $C_1$ to $C_{10}$, or a $C_1$ to $C_5$ organyl group. In an aspect, the $R^1$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^1$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^1$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes which have an $R^1$ group can be an alkyl group, a substituted alkyl group, a cycloalkyl group, a substituted cycloalkyl group, an aryl group, a substituted aryl group, an aralkyl group, or a substituted aralkyl group; alternatively an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^1$ alkyl group can be a $C_1$ to $C_{20}$, a $C_1$ to $C_{10}$, or a $C_1$ to $C_5$ alkyl group. In any aspect disclosed herein, the $R^1$ substituted alkyl group can be a $C_1$ to $C_{20}$, a $C_1$ to $C_{10}$, or a $C_1$ to $C_5$ substituted alkyl group. In any aspect disclosed herein, the $R^1$ cycloalkyl group can be a $C_4$ to $C_{20}$, a $C_4$ to $C_{15}$, or a $C_4$ to $C_{10}$ cycloalkyl group. In any aspect disclosed herein, the $R^1$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^1$ aryl group can be a $C_6$ to $C_{20}$, a $C_6$ to $C_{15}$, or a $C_6$ to $C_{10}$ aryl group. In any aspect disclosed herein, the $R^1$ substituted aryl group can be a $C_6$ to $C_{20}$, a $C_6$ to $C_{15}$, or a $C_6$ to $C_{10}$ substituted aryl group. In any aspect disclosed herein, the $R^1$ aralkyl group can be a $C_7$ to $C_{20}$, a $C_7$ to $C_{15}$, or a $C_7$ to $C_{10}$ aralkyl group. In any aspect disclosed herein, the $R^1$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted $R^1$ group.

In an aspect, $R^1$ can be a methyl group, an ethyl group, a propyl group, a butyl group, a pentyl group, a hexyl group, a heptyl group, or an octyl group; or alternatively, a methyl group, an ethyl group, a n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^1$ can be substituted. Each substituent of a substituted alkyl group (general or specific) independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group which can be utilized as $R^1$.

In an aspect, $R^1$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^1$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^1$ can be the same or different; alternatively, all the substituents of a multi-substituted cycloalkyl group can be the same; or alternatively, all the substituents of a multi-substituted cycloalkyl group can be different. Each substituent of a substituted cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy (general and specific) groups are independently disclosed herein. These substituent halogens, substituent hydrocarbyl groups, and substituent hydrocarboxy groups can be utilized without limitation to further describe a substituted cycloalkyl group (general or specific) which can be utilized as $R^1$.

In a non-limiting aspect, $R^1$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general and specific), dialkylcyclohexyl groups (general and specific), alkylcyclopentyl groups (general or specific), and/or dialkylcyclopentyl groups (general and specific) which can be utilized as $R^1$. Generally, the alkyl substituents of a dialkylcyclohexyl group or a dialkylcyclopentyl group can be the same; or alternatively, the alkyl substituents of a dialkylcyclohexyl group or a dialkylcyclopentyl group can be different. In some non-limiting aspects, $R^1$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^1$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^1$ can be a phenyl group, a substituted phenyl group; alternatively, a phenyl group; or alternatively, a substituted phenyl group. In an aspect, the substituted phenyl group, which can be utilized as $R^1$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^1$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^1$.

In a non-limiting aspect, $R^1$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as R. Generally, the alkyl substituents of a dialkylphenyl group (general or specific) or a trialkylphenyl group (general or specific) can be the same; or alternatively, the alkyl substituents of a dialkylphenyl group or trialkylphenyl group can be different. In some non-limiting aspects, $R^1$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In an aspect, $R^1$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^1$.

Generally, $R^2$ of the $N^2$-phosphinyl amidines and/or the $N^2$-phosphinyl amidine chromium compound complexes can be an organyl group; alternatively, an organyl group consisting of inert functional groups; or alternatively, a hydrocarbyl group. In an aspect, the $R^2$ organyl group can be a $C_1$ to $C_{20}$, a $C_1$ to $C_{15}$, a $C_1$ to $C_{10}$, or a $C_1$ to $C_5$ organyl group. In an aspect, $R^2$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, $R^2$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^2$ of the $N^2$-phosphinyl amidines and/or the $N^2$-phosphinyl amidine chromium compound complexes can be an acyl group or a substituted acyl group; an acyl group; or alternatively, a substituted acyl group. In an aspect, the acyl group can be a $C_1$ to $C_{20}$, a $C_1$ to $C_{15}$, a $C_1$ to $C_{10}$, or a $C_1$ to $C_5$ acyl group. In an aspect, the substituted acyl group can be a $C_1$ to $C_{20}$, a $C_1$ to $C_{15}$, a $C_1$ to $C_{10}$, or a $C_1$ to $C_5$ a substituted acyl group. In some aspects, $R^2$ of the $N^2$-phosphinyl amidines and/or the $N^2$-phosphinyl amidine chromium compound complexes can be an alkanoyl group, a substituted alkanoyl group, a benzoyl group, or a substituted benzoyl group; alternatively, an alkanoyl group or a substituted alkanoyl group; alternatively, a benzoyl group, or a substituted benzoyl group; alternatively, an alkanoyl group; alternatively, a substituted alkanoyl group; alternatively, a benzoyl group; or alternatively, a substituted benzoyl group. In any aspect disclosed herein, the $R^2$ alkanoyl group can be a $C_1$ to $C_{20}$, a $C_1$ to $C_{10}$, or a $C_1$ to $C_5$ alkanoyl group. In any aspect disclosed herein, the $R^2$ substituted alkanoyl group can be a $C_1$ to $C_{20}$, a $C_1$ to $C_{10}$, or a $C_1$ to $C_5$ substituted $R^2$ alkanoyl group. In any aspect disclosed herein, the $R^2$ benzoyl group can be a $C_7$ to $C_{20}$, a $C_7$ to $C_{15}$, or a $C_7$ to $C_{10}$ benzoyl group. In any aspect disclosed herein, the $R^2$ substituted benzoyl group can be a $C_7$ to $C_{20}$, a $C_1$ to $C_{15}$, or a $C_1$ to $C_{10}$ substituted $R^2$ benzoyl group. Each substituent of a substituted alkanoyl group (general or specific), and/or substituted benzoyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe substituted alkanoyl groups and/or substituted benzoyl group which can be utilized as $R^2$.

In an aspect, $R^2$ of the $N^2$-phosphinyl amidines and/or the $N^2$-phosphinyl amidine chromium compound complexes can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^2$ of the $N^2$-phosphinyl amidine and/or the $N^2$-phosphinyl amidine chromium compound complexes can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^2$ alkyl group can be a $C_1$ to $C_{20}$, a $C_1$ to $C_{10}$, or a $C_1$ to $C_5$ alkyl group. In any aspect disclosed herein, the $R^2$ substituted alkyl group can be a $C_1$ to $C_{20}$, a $C_1$ to $C_{10}$, or a $C_1$ to $C_5$ substituted alkyl group. In any aspect disclosed herein, the $R^2$ cycloalkyl group can be a $C_4$ to $C_{20}$, a $C_4$ to $C_{15}$, or a $C_4$ to $C_{10}$ cycloalkyl group. In any aspect disclosed herein, the $R^2$ substituted cycloalkyl group can be a $C_4$ to $C_{20}$, a $C_4$ to $C_{15}$, or a $C_4$ to $C_{10}$ substituted cycloalkyl group. In any aspect disclosed herein, the $R^2$ aryl group can be a $C_6$ to $C_{20}$, a $C_6$ to $C_{15}$, or a $C_6$ to $C_{10}$ aryl group. In any aspect disclosed herein, the $R^2$ substituted aryl group can be a $C_6$ to $C_{20}$, a $C_6$ to $C_{15}$, or a $C_6$ to $C_{10}$ substituted aryl group. In any aspect disclosed herein, the $R^2$ aralkyl group can be a $C_7$ to $C_{20}$, a $C_7$ to $C_{15}$, or a $C_7$ to $C_{10}$ aralkyl group. In any aspect disclosed herein, the $R^2$ substituted aryl group can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^2$.

In an aspect, $R^2$ can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a tert-butyl (2-methyl-2-propyl) group, or a neopentyl (2,2-dimethyl-1-propyl) group. In some aspects, the alkyl groups which can be utilized as $R^2$ can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^2$.

In an aspect, $R^2$ can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized as $R^2$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^2$ can be the same or different; alternatively, all the substituents of a multi-substituted cycloalkyl group can be the same; or alternatively, all the substituents of a multi-substituted cycloalkyl group can be different. Each substituent of a cycloalkyl group having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^2$.

In a non-limiting aspect, $R^2$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^2$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^2$ can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^2$ can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^2$ can be a phenyl group, a substituted phenyl group; alternatively, a phenyl group; or alternatively, a substituted phenyl group. In an aspect, the substituted phenyl group, which can be utilized as $R^2$ can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^2$ can be the same or different; alternatively, all the substituents of a multi-substituted cycloalkyl group can be the same; or alternatively, all the substituents of a multi-substituted cycloalkyl group can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^2$.

In a non-limiting aspect, $R^2$ can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^2$. Generally, the alkyl substituents of a dialkylphenyl group (general or specific) or trialkylphenyl group (general or specific) can be the same; or alternatively, the alkyl substituents of a dialkylphenyl group or trialkylphenyl group can be different. In some non-limiting aspects, $R^2$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^2$ can be a phenyl group, a 2-alkoxyphenyl group, or a 4-alkoxyphenyl group. In some non-limiting aspects, $R^2$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In another non-limiting aspect, $R^2$ can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^2$ can be a phenyl group, a 2-fluorophenyl group, a 4-fluorophenyl group, or a 2,6-difluorophenyl group.

In an aspect, $R^2$ can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group which can be utilized as $R^2$.

In further aspects, $R^1$ and $R^2$ can be joined to form a ring or a ring system containing the carbon-nitrogen double bond of the $N^2$-phosphinyl amidines and/or the $N^2$-phosphinyl amidine chromium compound complexes. The joining of $R^1$ and $R^2$ can be designated as $L^{12r}$ and can be an organylene group; alternatively, an organylene group consisting of inert functional groups; alternatively, a hydrocarbylene group; or alternatively, an alkylene group. In an aspect, the $L^{12r}$ organylene group, when present, can be a $C_3$ to $C_{30}$, a $C_3$ to $C_{20}$, a $C_3$ to $C_{15}$, or a $C_3$ to $C_{10}$ organylene group. In some aspects, the $L^{12r}$ organylene group consisting of inert functional groups, when present, can be a $C_3$ to $C_{30}$, a $C_3$ to $C_{20}$, a $C_3$ to $C_{15}$, or a $C_3$ to $C_{10}$ organylene group consisting of inert functional groups. In other aspects, the $L^{12r}$ hydrocarbyl group, when present, independently can be a $C_3$ to $C_{30}$, a $C_3$ to $C_{20}$, a $C_3$ to $C_{15}$, or a $C_3$ to $C_{10}$ hydrocarbylene group. In a further aspect, the $L^{12r}$ alkylene group, when present, independently ca n be a $C_3$ to $C_{30}$, a $C_3$ to $C_{20}$, a $C_3$ to $C_{15}$, or a $C_3$ to $C_{10}$ alkylene group. In an aspect, $L^{12}$, can be prop-1,3-ylene group, a propen-1,3-ylene group (—$CH_2CH$=$CH$—), a but-1,3-ylene group, a but-1-en-1,3-ylene group (—$CH$=$CHCH(CH_3)$—), a but-1-en-1,3-ylene group (—$CH_2CH$=$C(CH_3)$—), a 3-methylbut-1,3-ylene group (—$CH_2CH_2C(CH_3)_2$—), a 2-methylbut-1,3-ylene group (—$CH_2CH(CH_3)CH(CH_3)$—), a 3-methylbut-1-en-1,3-ylene group (—$CH$=$CHC(CH_3)_2$—), a 2-methylbut-1,3-ylene group (—$CH_2C(CH_3)$=$C(CH_3)$—) a but-1,4-ylene group a but-1-en-1,4-ylene group (—$CH$=$CHCH_2CH_2$)—), a but-2-en-1,4-ylene group (—$CH_2CH$=$CHCH_2$—), or a 1,4-pent-1,4-ylene group.

Generally, T of the heterocyclic 2-[(phosphinyl)aminyl] imines and/or the heterocyclic 2-[(phosphinyl)aminyl]imine chromium compound complexes can be oxygen or sulfur. In and aspect, T of the heterocyclic 2-[(phosphinyl)aminyl] imines and/or the heterocyclic 2-[(phosphinyl)aminyl]imine chromium compound complexes can be oxygen; or alternatively, sulfur.

Generally, $R^{2a}$ and/or $R^{2b}$, of the $N^2$-phosphinyl guanidines and/or the $N^2$-phosphinyl guanidine chromium compound complexes which have an $R^{2a}$ and/or $R^{2b}$ group, independently can be hydrogen or an organyl group; alternatively, hydrogen or an organyl group consisting of inert functional groups; alternatively, hydrogen or a hydrocarbyl group; alternatively, hydrogen; alternatively, an organyl group; alternatively, an organyl group consisting of inert functional groups; or alternatively, a hydrocarbyl group. In an aspect, the $R^{2a}$ and/or $R^{2b}$ organyl groups independently can be a $C_1$ to $C_{20}$, a $C_1$ to $C_{15}$, a $C_1$ to $C_{10}$, or a $C_1$ to $C_5$ organyl group. In some aspects, the $R^{2a}$ and/or $R^{2b}$ organyl groups consisting of inert functional groups independently can be a $C_1$ to $C_{20}$, a $C_1$ to $C_{15}$, a $C_1$ to $C_{10}$, or a $C_1$ to $C_5$ organyl group consisting of inert functional groups. In other aspects, the $R^{2a}$ and/or $R^{2b}$ hydrocarbyl groups independently can be a $C_1$ to $C_{20}$, a $C_1$ to $C_{15}$, a $C_1$ to $C_{10}$, or a $C_1$ to $C_5$ hydrocarbyl group.

In an aspect, $R^{2a}$ and $R^{2b}$, of the $N^2$-phosphinyl guanidines and/or the $N^2$-phosphinyl guanidine chromium compound complexes which have an $R^{2a}$ and/or $R^{2b}$ organyl group, independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{2a}$ and/or $R^{2b}$ alkyl group independently can be $C_1$ to $C_{20}$, a $C_1$ to $C_{10}$, or a $C_1$ to $C_5$ alkyl group. In any aspect disclosed herein, the $R^{2a}$ and/or $R^{2b}$ cycloalkyl group independently can be a $C_4$ to $C_{20}$, a $C_4$ to $C_{15}$, or a $C_4$ to $C_{10}$ cycloalkyl group. In any aspect disclosed herein, the $R^{2a}$ and/or $R^{2b}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, the $R^{2a}$ and/or $R^{2b}$ aryl group independently can be a $C_6$ to $C_{20}$, a $C_6$ to $C_{15}$, or a $C_6$ to $C_{10}$ aryl group. In any aspect disclosed herein, the $R^{2a}$ and/or $R^{2b}$ substituted aryl group independently can be a $C_6$ to $C_{20}$, a $C_6$ to $C_{15}$, or a $C_6$ to $C_{10}$ substituted aryl group. Each substituent of a substituted cycloalkyl group (general or specific) and/or a substituted aryl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^{2a}$ and/or $R^{2b}$.

In an aspect, $R^1$ and $R^{2a}$ of the $N^2$-phosphinyl guanidines and/or the $N^2$-phosphinyl guanidine chromium compound complexes can be joined to form a group, $L^{12}$, wherein $L^{12}$, the $N^1$ nitrogen atom, and the $N^3$ nitrogen atom form a ring or a ring system. In another aspect, $R^3$ and $R^{2b}$ of the $N^2$-phosphinyl guanidines and/or the $N^2$-phosphinyl guanidine chromium compound complexes can be joined to form a group, $L^{23}$, wherein $L^{23}$, the $N^2$ nitrogen atom, and the $N^3$ nitrogen atom form a ring or a ring system. In an aspect, $L^{12}$ and/or $L^{23}$, of the $N^2$-phosphinyl guanidines and/or the $N^2$-phosphinyl guanidine chromium compound complexes which have an $L^2$ group and/or an $L^{23}$ group, independently can be an organylene group; alternatively, an organylene group consisting of inert functional groups; or alternatively, a hydrocarbylene group. The $L^{12}$ and/or $L^{23}$ organylene groups independently can be a $C_2$ to $C_{20}$, a $C_2$ to $C_{15}$, a $C_2$ to $C_{10}$, or a $C_2$ to $C_5$ organylene group. The $L^{12}$ and/or $L^{23}$ organylene groups consisting of inert functional groups independently can be a $C_2$ to $C_{20}$, a $C_2$ to $C_{15}$, a $C_2$ to $C_{10}$, or a $C_2$ to $C_5$ organylene group consisting of inert functional groups. The $L^{12}$ and/or $L^{23}$ hydrocarbylene groups independently can be a $C_2$ to $C_{20}$, a $C_2$ to $C_{15}$, a $C_2$ to $C_{10}$, or a $C_2$ to $C_5$ hydrocarbylene group.

In an aspect, $L^{12}$ of the $N^2$-phosphinyl guanidines, the $N^2$-phosphinyl guanidine chromium compound complexes, the heterocyclic 2-[(phosphinyl)aminyl]imines and/or the heterocyclic 2-[(phosphinyl)aminyl]imine chromium compound complexes which have an $L^{12}$, and $L^{23}$ of the $N^2$-phosphinyl guanidines and/or the $N^2$-phosphinyl guanidine chromium compound complexes which have an $L^{23}$, can have any structure provided in Table 1. In some aspects, $L^{12}$ and/or $L^{23}$ can have Structure 1L, Structure 2L, Structure 3L, Structure 4L or Structure 5L. In some aspects, $L^{12}$ and/or $L^{23}$ can have Structure 2L or Structure 3L; alternatively, Structure 4L or Structure 5L. In other aspects, $L^{12}$ and/or $L^{23}$ can have Structure 1L; alternatively, Structure 2L; alternatively, Structure 3L; alternatively, Structure 4L; or alternatively, Structure 5L. In some $N^2$-phosphinyl guanidine and $N^2$-phosphinyl guanidine chromium compound complex aspects, $L^{12}$ and/or $L^{23}$ can have Structure 6L. It should be noted that when $L^{12}$ or $L^{23}$ has Structure 6L the corresponding $R^{2b}$ or $R^{2a}$ is null because of the double bond link with the $N^3$ nitrogen atom of the $N^2$-phosphinyl guanidine and/or the $N^2$-phosphinyl guanidine chromium compound complex.

TABLE 1

Structures for Linking Groups $L^{12}$ and/or $L^{23}$.

| | |
|---|---|
| $—(CR^{L1}R^{L2})_m—$ | Structure 1L |
| $—CR^{L3}R^{L4}—CR^{L5}R^{L6}—$ | Structure 2L |
| $—CR^{L3}R^{L4}—CR^{L7}R^{L8}—CR^{L5}R^{L6}—$ | Structure 3L |
| $—CR^{L11}=CR^{L12}—$ | Structure 4L |
| 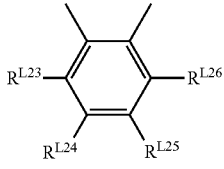 | Structure 5L |
| $=CR^{L27}—CR^{L28}=CR^{L29}—$ | Structure 6L |

Within the structures of Table 1, the undesignated valences of $L^{12}$ and/or $L^{23}$ represent the points at which $L^{12}$ and/or $L^{23}$, when present, attach to the respective nitrogen atoms of the $N^2$-phosphinyl guanidine and the $N^2$-phosphinyl guanidine chromium compound complex. Additionally, with the structures of Table 1, the undesignated valences of $L^{12}$ represent the points at which $L^{12}$ attach to T and the respective nitrogen atom of the heterocyclic 2-[(phosphinyl) aminyl]imine and/or the heterocyclic 2-[(phosphinyl)aminyl]imine chromium compound complex. Generally, m can be an integer ranging from 2 to 5. In further aspects, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group; or alternatively, hydrogen. Non-hydrogen substituent groups (general and specific) are independently disclosed herein and can be utilized without limitation to further describe the linking group having Structure 1L, Structure 2L, Structure 3L, Structure 4L, Structure 5L, and/or Structure 6L. In an aspect, $L^{12}$ and/or $L^{23}$ independently can be an eth-1,2-ylene group ($—CH_2CH_2—$), an ethen-1,2-ylene group ($—CH=CH—$), a prop-1,3-ylene group ($—CH_2CH_2CH_2—$), a propen-1,2-ylene group ($—C(CH_3)=CH—$), a propen-1,3-ylene group ($—CH=CHCH_2—$), a but-1,3-ylene group ($—CH_2CH_2CH(CH_3)—$), a 3-methylbut-1,3-ylene group ($—CH_2CH_2C(CH_3)_2—$), or a phen-1,2-ylene group. In some non-limiting aspects, $L^{12}$ and/or $L^{23}$ be an eth-1,2-ylene group ($—CH_2CH_2—$), a prop-1,3-ylene group ($—CH_2CH_2CH_2—$), a propen-1,2-ylene group ($—C(CH_3)=CH—$), a propen-1,3-ylene group ($—CH=CHCH_2—$), a but-1,3-ylene group ($—CH_2CH_2CH(CH_3)—$), or a 3-methylbut-1,3-ylene group ($—CH_2CH_2C(CH_3)_2—$); alternatively, an eth-1,2-ylene group ($—CH_2CH_2—$), an ethen-1,2-ylene group ($—CH=CH—$), a prop-1,3-ylene group ($—CH_2CH_2CH_2—$), or a phen-1,2-ylene group; alternatively, an eth-1,2-ylene group ($—CH_2CH_2—$) or a prop-1,3-ylene group ($—CH_2CH_2CH_2—$); alternatively, an ethen-1,2-ylene group ($—CH=CH—$) or a phen-1,2-ylene group; alternatively, an eth-1,2-ylene group ($—CH_2CH_2—$); alternatively, a prop-1,3-ylene group ($—CH_2CH_2CH_2—$); alternatively, a propen-1,2-ylene group ($—C(CH_3)=CH—$); alternatively, a propen-1,3-ylene group ($—CH=CHCH_2—$); or alternatively, a phen-1,2-ylene group.

In an aspect, $L^{12}$ can have a structure that can comprise at least one substituent located on the carbon atom attached to the $N^1$ nitrogen atom of the $N^2$-phosphinyl guanidine and/or the $N^2$-phosphinyl guanidine chromium compound complex; alternatively, can comprise only one substituent located on the carbon atom attached to the $N^1$ nitrogen atom of the $N^2$-phosphinyl guanidine and/or the $N^2$-phosphinyl guanidine chromium compound complex; or alternatively, can comprise two substituents located on the carbon atom attached to the $N^1$ nitrogen atom of the $N^2$-phosphinyl guanidine and/or the $N^2$-phosphinyl guanidine chromium compound complex. In another aspect, $L^{12}$ can have a structure that can consist of one substituent located on the carbon atom attached to the $N^1$ nitrogen atom the $N^2$-phosphinyl guanidine and/or the $N^2$-phosphinyl guanidine chromium compound complex; or alternatively, can consist of two substituents located on the carbon atom attached to the $N^1$ nitrogen atom of the $N^2$-phosphinyl guanidine and/or the $N^2$-phosphinyl guanidine chromium compound complex.

In an aspect, $R^{2a}$ and $R^{2b}$ of the $N^2$-phosphinyl guanidines and/or the $N^2$-phosphinyl guanidine chromium compound complexes can be joined to form a group, $L^{22}$, wherein $R^{2a}$, $R^{2b}$, and the $N^3$ nitrogen (or $L^{22}$ and the $N^3$ nitrogen) form a ring or ring system. In an aspect, $L^{22}$ of the $N^2$-phosphinyl guanidines and/or the $N^2$-phosphinyl guanidine chromium compound complexes having an $L^2$ group can be an organylene group; alternatively, an organylene group consisting of inert functional groups; or alternatively, a hydrocarbylene group. The $L^{22}$ organylene group can be a $C_3$ to $C_{20}$, a $C_3$ to $C_{15}$, or a $C_3$ to $C_{10}$ organylene group. The $L^{22}$ organylene group consisting of inert functional groups can be a $C_3$ to $C_{20}$, a $C_3$ to $C_{15}$, or a $C_3$ to $C_{10}$ organylene group consisting of inert functional groups. The $L^{22}$ hydrocarbylene group can be a $C_4$ to $C_{20}$, a $C_4$ to $C_{15}$, or a $C_4$ to $C_{10}$ hydrocarbylene group.

In an aspect, $L^{22}$ can have any structure provided in Table 2. In some aspects, $L^{22}$ can have Structure 11L, Structure 12L, Structure 13L, Structure 14L, Structure 15L, or Structure 16L. In other aspects, $L^{22}$ can have Structure 11L; alternatively, Structure 12L; alternatively, Structure 13L; alternatively, Structure 14L; or alternatively, Structure 15L.

TABLE 2

Structures for Linking Groups $L^{22}$.

| | |
|---|---|
| —$(CR^{L31}R^{L32})_n$— | —$CR^{L41}R^{L42}$—$CR^{L45}R^{L46}CR^{L47}R^{L48}CR^{L43}R^{L44}$— |
| Structure 11L | Structure 12L |
| —$CR^{L41}R^{L42}$—$CR^{L45}R^{L46}$—$CR^{L49}R^{L50}$—$CR^{L47}R^{L48}$—$CR^{L43}R^{L44}$— | |
| Structure 13L | |
| —$CR^{L41}R^{L42}$—$CR^{L45}R^{L46}$—O—$CR^{L47}R^{L48}$—$CR^{L43}R^{L44}$— | —$CR^{L51}$=$CR^{L53}$—$CR^{L54}$=$CR^{L52}$— |
| Structure 14L | Structure 15L |

Within the structures of Table 2, the undesignated valences represent the points at which $L^{22}$ of the $N^2$-phosphinyl guanidine and/or the $N^2$-phosphinyl guanidine chromium compound complex, when present, attach to the $N^3$ nitrogen atom of the $N^2$-phosphinyl guanidine and/or the $N^2$-phosphinyl guanidine chromium compound complex. Generally, n can be an integer ranging from 4 to 7. In further aspects, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L4}1$, $R^{L42}$, $R^{L43}$, $R^{L44}$, $R^{L45}$, $R^{L46}$, $R^{L47}$, and $R^{L48}$ of the linking group having Structure 14L, and $R^{L41}$, $R^{L42}$, $R^{L43}$, $R^{L44}$, $R^{L45}$, $R^{L46}$, $R^{L47}$, and $R^{L48}$ of the linking group having Structure 15L independently can be a hydrogen or a non-hydrogen substituent group; alternatively, hydrogen. Non-hydrogen substituent groups are independently disclosed herein and can be utilized without limitation to further describe the linking group having Structure 11L, Structure 12L, Structure 13L, Structure 14L, and/or Structure 15L. In an aspect, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; or alternatively, a but-1,4-ylene group, a pent-1,5-ylene group, or a bis(eth-2-yl)ether group.

Generally, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl] imines, and/or the heterocyclic 2-[(phosphinyl)aminyl] imine chromium compound complexes which have an $R^3$ group can be hydrogen or an organyl group; hydrogen or an organyl group consisting of inert functional group; alternatively, hydrogen or a hydrocarbyl group; alternatively, hydrogen; alternatively, an organyl group; alternatively, an organyl group consisting of inert functional group; or alternatively, a hydrocarbyl group. In an aspect, the $R^3$ organyl group can be a $C_1$ to $C_{20}$, a $C_1$ to $C_{15}$, a $C_1$ to $C_{10}$, or a $C_1$ to $C_5$ organyl group. In an aspect, the $R^3$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^3$ hydrocarbyl group can be a $C_1$ to $C_{20}$, a $C_1$ to $C_{15}$, a $C_1$ to $C_{10}$, or a $C_1$ to $C_5$ hydrocarbyl group. In other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes which have an $R^3$ group can be a $C_1$ to $C_{30}$, a $C_1$ to $C_{20}$, a $C_1$ to $C_{15}$, a $C_1$ to $C_{10}$, or a $C_1$ to $C_5$ alkyl group. In yet other aspects, $R^3$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl] imines, and/or the heterocyclic 2-[(phosphinyl)aminyl] imine chromium compound complexes can be a phenyl group or a $C_6$ to $C_{20}$ substituted phenyl group; alternatively, a phenyl group or a $C_6$ to $C_{15}$ substituted phenyl group; or alternatively, a phenyl group or a $C_6$ to $C_{10}$ substituted phenyl group. Substituent groups (general and specific) are provided herein and these substituent groups can be utilized to further describe the substituted phenyl groups which can be utilized as $R^3$ the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, and/or the $N^2$-phosphinyl guanidine chromium compound complexes having a non-hydrogen $R^3$ group.

Generally, $R^4$ and/or $R^5$ of the $N^2$-phosphinyl formamidines, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl] imine chromium compound complexes independently can be an organyl group; alternatively, an organyl group consisting of inert functional groups; or alternatively, a hydrocarbyl group. In an aspect, the $R^4$ and/or $R^5$ organyl groups can be a $C_1$ to $C_{20}$, a $C_1$ to $C_{15}$, a $C_1$ to $C_{10}$, or a $C_1$ to $C_5$ organyl group. In an aspect, the $R^4$ and/or $R^5$ organyl groups consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^4$ and/or $R^5$ hydrocarbyl groups can be a $C_1$ to $C_{20}$, a $C_1$ to $C_{15}$, a $C_1$ to $C_{10}$, or a $C_1$ to $C_5$ hydrocarbyl group. In an aspect, $R^4$ and/or $R^5$ of the $N^2$-phosphinyl formamidine, the $N^2$-phosphinyl formamidine chromium compound complexes, the $N^2$-phosphinyl amidines, the $N^2$-phosphinyl amidine chromium compound complexes, the $N^2$-phosphinyl guanidines, the $N^2$-phosphinyl guanidine chromium compound complexes, the heterocyclic 2-[(phosphinyl)aminyl]imines, and/or the heterocyclic 2-[(phosphinyl)aminyl]imine chromium compound complexes independently can be an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; alternatively, an alkyl group, a cycloalkyl group, an aryl group, or an aralkyl group; alternatively, an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, the $R^4$ and/or $R^5$ alkyl groups independently can be a $C_1$ to $C_{20}$, a $C_1$ to $C_{10}$, or a $C_1$ to $C_5$ alkyl group. In any aspect disclosed herein, the $R^4$ and/or $R^5$ substituted alkyl groups independently can be a $C_1$ to $C_{20}$, a $C_1$ to $C_{10}$, or $C_1$ to $C_5$ substituted alkyl group. In any aspect disclosed herein, the $R^4$ and/or $R^5$ cycloalkyl groups independently can be a $C_4$ to $C_{20}$, a $C_4$ to $C_{15}$, or a $C_4$ to $C_{10}$ cycloalkyl group. In any aspect disclosed herein, the $R^4$ and/or $R^5$ substituted cycloalkyl groups independently can be a $C_4$ to $C_{20}$, a $C_4$ to $C_{15}$, or a $C_4$ to $C_{10}$ substituted cycloalkyl group. In any aspect disclosed herein, the $R^4$ and/or $R^5$ aryl groups independently can be a $C_6$ to $C_{20}$, a $C_6$ to $C_{15}$, or a $C_6$ to $C_{10}$ aryl group. In any aspect disclosed herein, the $R^4$ and/or $R^5$ substituted aryl group independently can be a $C_6$ to $C_{20}$, a $C_6$ to $C_{15}$, or a $C_6$ to $C_{10}$ substituted aryl group. In any aspect disclosed herein, the $R^4$ and/or $R^5$ aralkyl groups independently can be a $C_7$ to $C_{20}$, a $C_7$ to $C_{15}$, or a $C_7$ to $C_{10}$ aralkyl group. In any aspect disclosed herein, the $R^4$ and/or $R^5$ substituted aryl groups independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe $R^4$ and/or $R^5$.

In an aspect, $R^4$ and $R^5$ independently can be a methyl group, an ethyl group, a propyl group, a butyl group, a pentyl group, a hexyl group, a heptyl group, or an octyl group; or alternatively, a methyl group, an ethyl group, an n-propyl (1-propyl) group, an iso-propyl (2-propyl) group, a 2-methyl-1-propyl group, a tert-butyl (2-methyl-2-propyl) group, or a neopentyl (2,2-dimethyl-1-propyl) group. In some aspects, the alkyl groups which can be utilized as $R^4$ and/or $R^5$ can be substituted. Each substituent of a substituted alkyl group independently can be a halogen or a hydrocarboxy group; alternatively, a halogen; or alternatively, a hydrocarboxy group. Substituent halogens and substituent hydrocarboxy (general and specific) groups are independently disclosed herein. These substituent halogens and substituent hydrocarboxy groups can be utilized without limitation to further describe a substituted alkyl group which can be utilized as $R^4$ and/or $R^5$.

In an aspect, $R^4$ and $R^5$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group. In an aspect, the substituted cycloalkyl group, which can be utilized for $R^4$ and/or $R^5$, can be a 2-substituted cyclohexyl group, a 2,6-disubstituted cyclohexyl group, a 2-substituted cyclopentyl group, or a 2,5-disubstituted cyclopentyl group; alternatively, a 2-substituted cyclohexyl group or a 2,6-disubstituted cyclohexyl group; alternatively, a 2-substituted cyclopentyl group or a 2,5-disubstituted cyclopentyl group; alternatively, a 2-substituted cyclohexyl group or a 2-substituted cyclopentyl group; or alternatively, a 2,6-disubstituted cyclohexyl group or a 2,5-disubstituted cyclopentyl group. In an aspect where the substituted cycloalkyl group (general or specific) has more the one substituent, the substituents can be the same or different; alternatively, the same; or alternatively, different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^4$ and/or $R^5$.

In a non-limiting aspect, $R^4$ and $R^5$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further described alkylcyclohexyl groups (general or specific), dialkylcyclohexyl groups (general or specific), alkylcyclopentyl groups (general or specific), and/or dialkylcyclopentyl groups (general or specific) which can be utilized as $R^4$ and/or $R^5$. Generally, the alkyl substituents of a disubstituted cyclohexyl or cyclopentyl group can be the same; or alternatively, the alkyl substituents of a dialkyl cyclohexyl or cyclopentyl group can be different. In some non-limiting aspects, $R^4$ and $R^5$ independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^4$ and $R^5$ independently can be, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, $R^4$ and $R^5$ independently can be a phenyl group, a substituted phenyl group; alternatively, a phenyl group; or alternatively, a substituted phenyl group. In an aspect, the substituted phenyl group, which can be utilized for $R^4$ and/or $R^5$, can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; or alternatively, a 2,4,6-trisubstituted phenyl group. In an aspect, one or more substituents of a multi-substituted phenyl group utilized as $R^4$ and/or $R^5$ can be the same or different; alternatively, all the substituents of a multi-substituted cycloalkyl group can be the same; or alternatively, all the substituents of a multi-substituted cycloalkyl group different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted phenyl group (general or specific) which can be utilized as $R^4$ and/or $R^5$.

In a non-limiting aspect, $R^4$ and $R^5$ independently can be a phenyl group, a 2-alkylphenyl group, a 3-alkylphenyl group, a 4-alkylphenyl group, a 2,4-dialkylphenyl group a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^4$ and/or $R^5$. Generally, the alkyl substituents of a dialkylphenyl group (general or specific) or a trialkylphenyl group (general or specific) can be the same; or alternatively, the alkyl substituents of a dialkylphenyl group (general or specific) or a trialkyl phenyl group (general or specific) can be different. In some non-limiting aspects, $R^4$ and $R^5$ independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, phenyl group, a 2-methylphenyl group, a 2-ethylphenyl group, a 2-n-propylphenyl group, a 2-isopropylphenyl group, or a 2-tert-butylphenyl group; alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, $R^4$ and $R^5$ can be a phenyl group, a 2-alkoxyphenyl group, or a 4-alkoxyphenyl group. In some non-limiting aspects, $R^4$ and/or $R^5$ can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, $R^4$ and $R^5$ independently can be a phenyl group, a 2-halophenyl group, a 4-halophenyl group, or a 2,6-dihalophenylgroup. Generally, the halides of a dihalophenyl group can be the same; or alternatively, the halides of a dihalophenyl group can be different. In some aspects, $R^4$ and $R^5$ independently can be a phenyl group, a 2-fluorophenyl group, a 4-fluorophenyl group, or a 2,6-difluorophenyl group.

In an aspect, $R^4$ and $R^5$ independently can be a benzyl group or a substituted benzyl group; alternatively, a benzyl group; or alternatively, a substituted benzyl group. Each substituent of a substituted benzyl group independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl which can be utilized as $R^4$ and/or $R^5$.

In further aspects, $R^4$ and $R^5$ can be joined to form a ring or a ring system containing the phosphorus atom. The joining of $R^4$ and $R^5$ can be designated as $L^{45}$ and can be an organylene group; alternatively, an organylene group consisting of inert functional groups; alternatively, a hydrocarbylene group; or alternatively, an alkylene group. In an aspect, the $L^{45}$ organylene group, when present, can be a $C_4$ to $C_{30}$, a $C_4$ to $C_{20}$, a $C_4$ to $C_{15}$, or a $C_4$ to $C_{10}$ organylene group. In an aspect, the $L^{45}$ organylene group consisting of inert functional groups, when present, can be a $C_4$ to $C_{30}$, a $C_4$ to $C_{20}$, a $C_4$ to $C_{15}$, or a $C_4$ to $C_{10}$ organylene group consisting of inert functional groups. In an aspect, the $L^{45}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{45}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{45}$ can be a but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl) dipheylene group, or a 2,2'-(1,2-ethandiyl)diphenylene group.

In an aspect, the heteroatomic ligand or the heteroatomic ligand of the heteroatomic ligand chromium compound complex can have the formula $(R^{1s})_m X^{1s}(L^{1s}) X^{2s}(R^{2s})_n$ while the heteroatomic ligand chromium compound complex can have the formula:

In some aspects, the heteroatomic ligand or the heteroatomic ligand of the heteroatomic ligand chromium compound complex can have two groups capable of being described by the formula $(R^{1s})_m X^{1s}(L^{1s}) X^{2s}(R^{2s})_n$. In instances wherein the heteroatomic ligand can have two groups capable of being described by the formula $(R^{1s})_m X^{1s}(L^{1s}) X^{2s}(R^{2s})_n$, the two $L^{1s}$ groups are linked and the heteroatomic ligand and the heteroatomic ligand chromium compound complex can have the formulas:

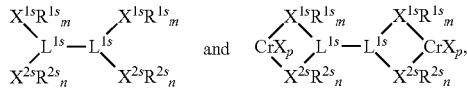

respectively.

In the heteroatomic ligand or the heteroatomic ligand of the heteroatomic ligand chromium compound complex having formula $(R^{1s})_m X^{1s}(L^{1s}) X^{2s}(R^{2s})_n$ or having two linked $(R^{1s})_m X^{1s}(L^{1s}) X^{2s}(R^{2s})_n$ groups, each $X^{1s}$ and each $X^{2s}$ independently can be selected from the group consisting of N, P, O, and S; each $L^{1s}$ can be an independent linking group between the respective $X^{1s}$s and $X^{2s}$s; each m and each n independently can be 1 or 2; and each $R^{1s}$ and each $R^{2s}$ independently can be a hydrogen, an organyl group (or alternatively, an organyl group consisting of inert functional group; or alternatively, a hydrocarbyl group), or a heterohydrocarbyl group, where when there are two or more $R^{1s}$s and/or two $R^{2s}$s, each $R^{1s}$ can be the same or different (alternatively, the same; or alternatively, different) and/or each $R^{2s}$ can be the same or different (alternatively, the same; or alternatively, different). $L^{1s}$, $X^{1s}$, $X^{2s}$, $R^{1s}$, $R^{2s}$, m, and n are independent elements of any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n and are independently described herein. These independent descriptions of $L^{is}$, $X^{1s}$, $X^{2s}$, $R^{1s}$, $R^{2s}$, m, and n can be utilized without limitation, and in any combination, to further describe any heteroatomic ligand or any heteroatomic ligand of the heteroatomic ligand chromium compound complex which have an $L^{1s}$, $X^{1s}$, $X^{2s}$, $R^{1s}$, $R^{2s}$, m, and/or n. Additionally, $CrX_p$ is an independent element of the heteroatomic ligand chromium compound complex, and is independently described herein, and can be utilized without limitation, and in any combination with $L^{1s}$, $X^{1s}$, $X^{2s}$, $R^{1s}$, $R^{2s}$, m, and n of the heteroatomic ligand to further describe the heteroatomic ligand chromium compound complexes contemplated herein.

In an aspect, each $X^{1s}$ and each $X^{2s}$ of any heteroatomic ligand or any heteroatomic ligand of any heteroatomic ligand chromium compound complex described herein having an $X^{1s}$ and/or $X^{2s}$ can be independently selected from N, P, O, and S; alternatively, independently selected from N and P; or alternatively, independently selected from O and S. In some aspects, each $X^{1s}$ and each $X^{2s}$ can be N; alternatively, P; alternatively, O; or alternatively, S. Each m and each n of any heteroatomic ligand or any heteroatomic ligand of any heteroatomic ligand chromium compound complex described herein having an m and/or n can be independently selected from 1 or 2; alternatively, 1; or alternatively, 2. Is some particular aspects, each m and/or each n can be 1 when $X^{1s}$ and/or $X^{2s}$, respectively, is O or S; alternatively, O; or alternatively, S. In some other particular aspects, each m and/or each n can be 2 when $X^{1s}$ and/or $X^{2s}$, respectively, is N or P; alternatively, N; or alternatively, P.

In a non-limiting aspect, the heteroatomic ligand can have the formula $R^{1s}S(L^{1s})SR^{2s}$, $(R^{1s})_2P(L^{1s})P(R^{2s})_2$ or $(R^{1s})_2N(L^{1s})N(R^{2s})_2$; alternatively, $R^{1s}S(L^{1s})SR^{2s}$; alternatively, $(R^{1s})_2P(L^{1s})P(R^{2s})_2$; or alternatively, $(R^{1s})_2N(L^{1s})N(R^{2s})_2$ while the heteroatomic ligand chromium compound complex can have any one of the formulas

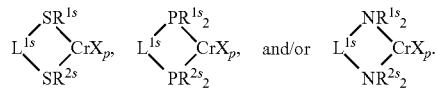

In non-limiting aspects where the heteroatomic ligand or the heteroatomic ligand of the heteroatomic ligand chromium compound complex has two linked heteroatomic groups, the heteroatomic ligand can have the formula selected from one or more of

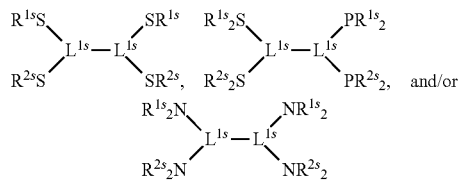

while the heteroatomic ligand chromium compound complex can have any one of the formulas

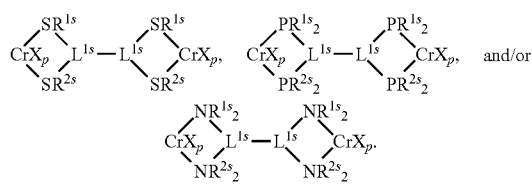

In an aspect, each $L^{1s}$ of any heteroatomic ligand or any heteroatomic ligand of the heteroatomic ligand chromium compound complex described herein independently can be any group capable of linking group $X^{1s}$ and $X^{2s}$ (and other $L^{1s}$ group when the heteroatomic ligand or heteroatomic ligand of the heteroatomic ligand chromium compound complex when there are more than one $L^{1s}$ group). In some aspects, each $L^{1s}$ independently can be an organylene group, an amin-di-yl group, or a phosphin-di-yl group; alternatively, an organylene group consisting of inert functional groups, an amin-di-yl group, or a phosphin-di-yl group; alternatively, a hydrocarbylene group, an amin-di-yl group, or a phosphin-di-yl group; alternatively an amin-di-yl group or a phosphin-di-yl group; alternatively, an organylene group; alternatively, an organylene group consisting of inert functional groups; alternatively, a hydrocarbylene group; alternatively, an amin-di-yl group; or alternatively, a phosphin-di-yl group. When there is more than one $L^{1s}$ group in the heteroatomic ligand or heteroatomic ligand of the heteroatomic ligand chromium compound complex each $L^{1s}$ independently can be an organic, an amine group, or a phosphine group; alternatively, an organic group consisting of inert functional groups, an amine group, or a phosphine group; alternatively, a hydrocarbon group, an amine group, or a phosphine group; alternatively an amine group or a phosphine group; alternatively, an organic group; alternatively, an organic group consisting of inert functional groups; alternatively, a hydrocarbon group; alternatively, an amine group; or alternatively, a phosphine group. In an aspect, the $L^{1s}$ organylene group or organic group can be a $C_1$ to $C_{20}$, a $C_1$ to $C_{15}$, a $C_1$ to $C_{10}$, or, a $C_1$ to $C_5$ organylene or organic group. In an aspect, the $L^{1s}$ organylene group consisting of inert functional groups can be a $C_1$ to $C_{20}$, a $C_1$ to $C_{15}$, a $C_1$ to $C_{10}$, or, a $C_1$ to $C_5$ organylene or organic group consisting of inert functional groups. In an aspect, the $L^{1s}$ hydrocarbylene group can be a $C_1$ to $C_{20}$, a $C_1$ to $C_{15}$, a $C_1$ to $C_{10}$, or a $C_1$ to $C_5$ hydrocarbylene or hydrocarbon group. In an aspect, the amin-di-yl or amine group can be a $C_1$ to $C_{30}$, a $C_1$ to $C_{20}$, a $C_1$ to $C_{15}$, or a $C_1$ to $C_{10}$ amin-di-yl or amine group. In an aspect, the phosphin-di-yl or phosphine group can be a $C_1$ to $C_{30}$, a $C_1$ to $C_{20}$, a $C_1$ to $C_{15}$, or a $C_1$ to $C_{10}$ phosphin-di-yl or phosphine group.

In an aspect, each $L^{1s}$ organylene or organic group can have the formula -($L^{3s}$)$NR^{5s}$($L^{4s}$)- or -($L^{3s}$)$PR^{5s}$($L^{4s}$)-; alternatively, -($L^{3s}$)$NR^{5s}$($L^{4s}$)-; or alternatively, -($L^{3s}$)$PR^{5s}$($L^{4s}$)-. In an aspect, the each amin-di-yl group can have the formula —$N(R^{5s})$—. In an aspect, each phosphin-di-yl group can have the formula —$P(R^{5s})$—. In these $L^{1s}$ group formulas, the dashes represent the undesignated valance to which the $X^{1s}$ and $X^{2s}$ of the heteroatomic ligand or the heteroatomic ligand of the heteroatomic ligand of the heteroatomic ligand chromium compound complex described herein attach. When there is more than one $L^{1s}$ group in the heteroatomic ligand or heteroatomic ligand of the heteroatomic ligand chromium compound complex, the $R^{5s}$ of each $L^{1s}$ group can be combined into a linking group designated as $L^{2s}$. In some non-limiting aspects, the heteroatomic ligand can have Structure PNP1, Structure PNP2, Structure NRNRN, Structure PRPRP, Structure SRNRS, Structure PRNRP, and Structure NRPRN; alternatively, Structure PNP1 or Structure PNP2; alternatively, Structure PRPRP, Structure SRNRS, or Structure PRNRP; alternatively, Structure PNP1; alternatively, Structure PNP2; alternatively, Structure NRNRN; alternatively, Structure PRPRP; alternatively, Structure SRNRS; alternatively, Structure PRNRP; or alternatively, Structure NRPRN. In some non-limiting aspects, the heteroatomic ligand chromium compound complex having a heteroatomic ligand $(R^{1s})_m X^{1s}(L^{1s})X^{2s}(R^{2s})_n$ which can be utilized in catalyst systems described herein can have Structure PNCr1, Structure PNPCr2, Structure NRNRNCr, Structure PRPRPCr, Structure SRNRSCr, Structure PRNRPCr, and Structure NRPRNCr; alternatively, Structure PNPCr1 or Structure PNPCr2; alternatively, Structure PRPRPCr, Structure SRNRSCr, or Structure PRNRPCr; alternatively, Structure PNPCr1; alternatively, Structure PNPCr2; alternatively, Structure NRNRNCr; alternatively, Structure PRPRPCr; alternatively, Structure SRNRSCr; alternatively, Structure PRNRPCr; or alternatively, Structure NRPRNCr.

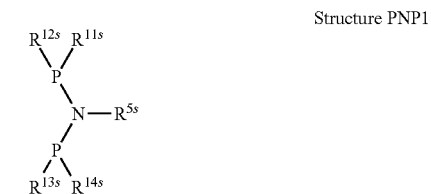

Structure PNP1

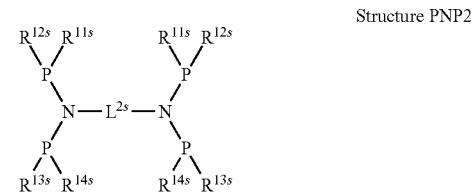

Structure PNP2

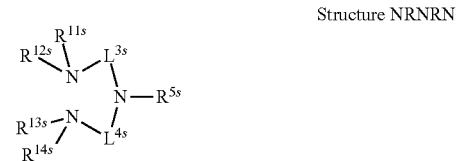

Structure NRNRN

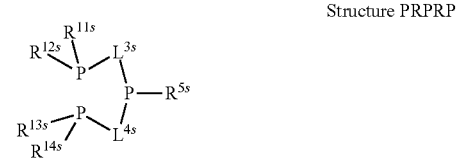

Structure PRPRP

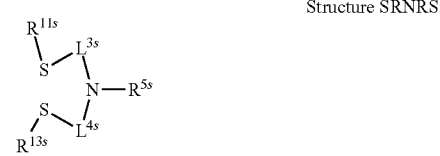

Structure SRNRS

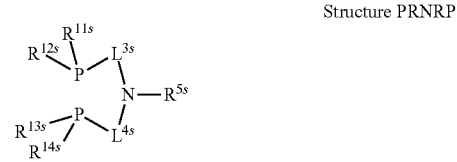

Structure PRNRP

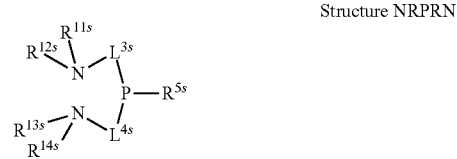

Structure NRPRN

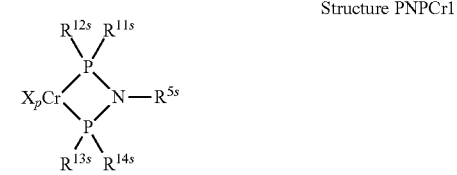

Structure PNPCr1

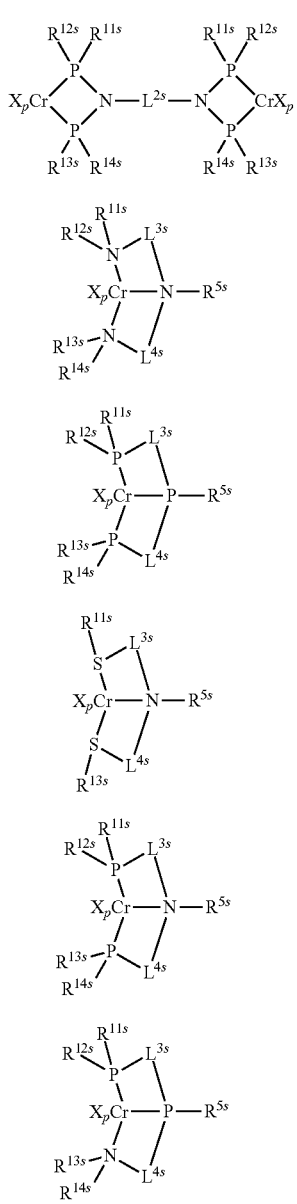

Structure PNPCr2

Structure NRNRNCr

Structure PRPRPCr

Structure SRNRSCr

Structure PRNRPCr

Structure NRPRNCr

The $R^{5s}$, $L^{2s}$, $L^{3s}$, $L^{4s}$, $R^{11s}$, $R^{12s}$, $R^{13s}$, and $R^{14s}$ are each independent elements of the heteroatomic ligands having Structure PNP1, Structure PNP2, Structure NRNRN, Structure PRPRP, Structure SRNRS, Structure PRNRP, or Structure NRPRN, and/or the heteroatomic ligand of the heteroatomic ligand chromium compound complexes having Structure PNPCr1, Structure PNPCr2, Structure NRNRNCr, Structure PRPRPCr, Structure SRNRSCr, Structure PRNRPCr, and Structure NRPRNCr in which they occur and are independently described herein. The independent descriptions of $R^{5s}$, $L^{2s}$, $L^{3s}$, $L^{4s}$, $R^{11s}$, $R^{12s}$, $R^{13s}$, and $R^{14s}$ can be utilized without limitation, and in any combination, to further describe the heteroatomic ligand structures and/or the heteroatomic ligand chromium compound complex structure in which they occur. Similarly, X and p are independent elements of the heteroatomic ligand chromium compound complexes having Structure PNCr1, Structure PNPCr2, Structure NRNCRNr, Structure PRPRPCr, Structure SRNRSCr, Structure PRNRPCr, and Structure NRPRNCr and are independently described herein. The independent description of X and p can be utilized without limitation, and in any combination, with the independently described $R^{5s}$, $L^{2s}$, $L^{3s}$, $L^{4s}$, $R^{11s}$, $R^{12s}$, $R^{13s}$, and $R^{14s}$ provided herein to further describe any heteroatomic ligand chromium compound complex having Structure PNPCr1, Structure PNPCr2, Structure NRNRNCr, Structure PRPRPCr, Structure SRNRSCr, Structure PRNRPCr, and/or Structure NRPRNCr.

Generally, $R^{1s}$, $R^{2s}$, $R^{11s}$, $R^{12s}$, $R^{13s}$, and/or $R^{14s}$, of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group, independently can be an organyl group; alternatively, an organyl group consisting of inert functional groups; or alternatively, a hydrocarbyl group. In an aspect, the organyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group. In an aspect, the organyl group consisting of inert functional groups which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ organyl group consisting of inert functional groups. In an aspect, the hydrocarbyl group which can be utilized as $R^{1s}$, $R^{2s}$, $R^{11s}$, $R^{12s}$, $R^{13s}$, and/or $R^{14s}$ independently can be a $C_1$ to $C_{20}$, a $C_1$ to $C_{15}$, a $C_1$ to $C_{10}$, or a $C_1$ to $C_5$ hydrocarbyl group.

In an aspect, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can an alkyl group, a substituted alkyl group, a cycloalkyl group, a substituted cycloalkyl group, an aryl group, a substituted aryl group, an aralkyl group, or a substituted aralkyl group; alternatively, an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, each $R^{1s}$, $R^{2s}$, $R^{11s}$, $R^{12s}$, $R^{13s}$, and/or $R^{14s}$ of any heteroatomic ligand structure depicted herein and/or any heteroatomic ligand chromium compound complex depicted herein having an $R^{1s}$, $R^{2s}$, $R^{11s}$, $R^{12s}$, $R^{13s}$, and/or $R^{14s}$ group independently can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group.

In any aspect disclosed herein, each $R^{1s}$, $R^{2s}$, $R^{11s}$, $R^{12s}$, $R^{13s}$, and/or $R^{14s}$ alkyl group independently can be a $C_1$ to $C_{20}$, a $C_1$ to $C_{10}$, or a $C_1$ to $C_5$ alkyl group. In any aspect disclosed herein, each $R^{1s}$, $R^{2s}$, $R^{11s}$, $R^{12s}$, $R^{13s}$, and/or $R^{14s}$ substituted alkyl group independently can be a $C_1$ to $C_{20}$, a $C_1$ to $C_{10}$, or a $C_1$ to $C_5$ substituted alkyl group. In any aspect disclosed herein, each $R^{1s}$, $R^{2s}$, $R^{11s}$, $R^{12s}$, $R^{13s}$, and/or $R^{14s}$ cycloalkyl group independently can be a $C_4$ to $C_{20}$, a $C_4$ to $C_{15}$, or a $C_4$ to $C_{10}$ cycloalkyl group. In any aspect disclosed herein, each $R^{1s}$, $R^{2s}$, $R^{11s}$, $R^{12s}$, $R^{13s}$, and/or $R^{14s}$ substituted cycloalkyl group independently can be a $C_4$ to $C_{20}$, a $C_4$ to $C_{15}$, or a $C_4$ to $C_{10}$ substituted cycloalkyl group. In any aspect disclosed herein, each $R^{1s}$, $R^{2s}$, $R^{11s}$, $R^{12s}$, $R^{13s}$, and/or $R^{14s}$ aryl group independently can be a $C_6$ to $C_{20}$, a $C_6$ to $C_{15}$, or a $C_6$ to $C_{10}$ aryl group. In any aspect disclosed herein, each $R^{1s}$, $R^{2s}$, $R^{11s}$, $R^{12s}$, $R^{13s}$, and/or $R^{14s}$ substituted aryl group independently can be a $C_6$ to $C_{20}$, a $C_6$ to $C_{15}$, or a $C_6$ to $C_{10}$ substituted aryl group. In any aspect disclosed herein, each $R^{1s}$, $R^{2s}$, $R^{11s}$, $R^{12s}$, $R^{13s}$, and/or $R^{14s}$ aralkyl group independently can be a $C_7$ to $C_{20}$, a $C_7$ to $C_{15}$, or a $C_7$ to $C_{10}$ aralkyl group. In any aspect disclosed herein, each $R^{1s}$, $R^{2s}$, $R^{11s}$, $R^{12s}$, $R^{13s}$, and/or $R^{14s}$ substituted aralkyl group independently can be a $C_7$ to $C_{20}$, a $C_7$ to $C_{15}$, or a $C_7$ to $C_{10}$ substituted aralkyl group. Each substituent of a substituted alkyl group (general or specific), a substituted cycloalkyl group (general or specific), a substituted aryl group (general or specific), and/or substituted aralkyl group (general or specific) can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarboxy groups, and substituent hydrocarboxy groups can be utilized without limitation to further describe a substituted group (general or specific) which can be utilized $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a methyl group, an ethyl group, a propyl group, a butyl group, a pentyl group, a hexyl group, a heptyl group, or an octyl group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the alkyl groups which can be utilized as each $R^{1s}$, $R^{2s}$, $R^{11s}$, $R^{12s}$, $R^{13s}$, and/or $R^{14s}$ independently can be substituted. Each substituent of a substituted alkyl group independently can be a halogen or a hydrocarboxy group; alternatively, a halogen; or alternatively, a hydrocarboxy group. Substituent halogens and substituent hydrocarboxy groups (general and specific) are independently disclosed herein. These substituent halogens and substituent hydrocarboxy groups can be utilized without limitation to further describe a substituted alkyl group (general or specific) which can be utilized as $R^{1s}$, $R^{2s}$, $R^{11s}$, $R^{12s}$, $R^{13s}$, and/or $R^{14s}$.

In an aspect, each $R^{1s}$, $R^{2s}$, $R^{11s}$, $R^{12s}$, $R^{13s}$, and/or $R^{14s}$ independently can be a cyclopentyl group, a substituted cyclopentyl group, a cyclohexyl group, or a substituted cyclohexyl group; alternatively, a cyclopentyl group or a substituted cyclopentyl group; or alternatively, a cyclohexyl group or a substituted cyclohexyl group; alternatively, a cyclopentyl group; alternatively, a substituted cyclopentyl group; alternatively, a cyclohexyl group; or alternatively, a substituted cyclohexyl group. In an aspect, the substituted cycloalkyl group, which can be utilized for any of $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted cyclohexyl group, a 2,6-disubstituted cyclohexyl group, a 2-subsituted cyclopentyl group, or a 2,5-disubstituted cyclopentyl group; alternatively, a 2-substituted cyclohexyl group or a 2,6-disubstituted cyclohexyl group; alternatively, a 2-subsituted cyclopentyl group or a 2,5-disubstituted cyclopentyl group; alternatively, a 2-substituted cyclohexyl group or a 2-subsituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{1s}$, $R^{2s}$, $R^{11s}$, $R^{12s}$, $R^{13s}$, and/or $R^{14s}$ can be the same or different; alternatively, all the substituents of a multi-substituted cycloalkyl group can be the same; or alternatively, all the substituents of a multi-substituted cycloalkyl group can be different. Each substituent of a substituted cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted cycloalkyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkyleyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{1s}$, $R^{2s}$, $R^{11s}$, $R^{12s}$, $R^{13s}$, and/or $R^{14}$. Generally, the alkyl substituents of a disubstituted cyclohexyl or cyclopentyl group can be the same, or alternatively, the alkyl substituents can be different. In some non-limiting aspects, each $R^{1s}$, $R^{2s}$, $R^{11s}$, $R^{12s}$, $R^{13s}$, and $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group.

In an aspect, each $R^{1s}$, $R^{2s}$, $R^{11s}$, $R^{12s}$, $R^{13s}$, and/or $R^{14s}$ independently can be a phenyl group or a substituted phenyl group; alternatively, a phenyl group; or alternatively, a substituted phenyl group. In an aspect, the substituted phenyl group which can be utilized for each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-subsituted phenyl group or a 3,5-disubstituted phenyl group; alternatively, a 2-substituted phenyl group or a 4-substituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. In an aspect, one or more substituents of a multi-substituted phenyl group utilized as $R^{1s}$, $R^{2s}$, $R^{11s}$, $R^{12s}$, $R^{13s}$, and/or $R^{14s}$ can be the same or different; alternatively, all the substituents can be the same; or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy group can be utilized without limitation to further describe a substituted phenyl group (general or specific) which can be utilized as $R^{1s}$, $R^{2s}$, $R^{11s}$, $R^{12s}$, $R^{13s}$, and/or $R^{14s}$.

In a non-limiting aspect, each $R^{1s}$, $R^{2s}$, $R^{11s}$, $R^{12s}$, $R^{13s}$, and/or $R^{14s}$ independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group or a 2,6-dialkylphenyl group; alternatively, a 3-alkylphenyl group or a 3,5-dialkylphenyl group; alternatively, a 2-alkylphenyl group or a 2,6-dialkylphenyl group; or alternatively, a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{1s}$, $R^{2s}$, $R^{11s}$, $R^{12s}$, $R^{13s}$, and/or $R^{14s}$. Generally, the alkyl substituents of dialkylphenyl groups (general or specific) or trialkylphenyl groups (general or specific) can be the same, or alternatively, the alkyl substituents can be different. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2-ethylphenyl group, a 2-n-propylphenyl group, a 2-isopropylphenyl group, or a 2-tert-butylphenyl group; or alternatively, a phenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group.

In a non-limiting aspect, each $R^{1s}$, $R^{2s}$, $R^{11s}$, $R^{12s}$, $R^{13s}$, and/or $R^{14s}$ independently can be a phenyl group, a 2-alkoxyphenyl group, or a 4-alkoxyphenyl group. In some non-limiting aspects, each $R^{1s}$, $R^{2s}$, $R^{11s}$, $R^{12s}$, $R^{13s}$, and/or $R^{14s}$, when present in any heteroatomic ligand described herein, any heteroatomic ligand of the heteroatomic ligand chromium compound complex described herein, any heteroatomic ligand formula or structure provided herein, and/or any heteroatomic ligand chromium compound complex structure provided herein, independently can be a phenyl group, a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; or alternatively, a 4-methoxyphenyl group, a 4-ethoxyphenyl group, a 4-isopropoxyphenyl group, or a 4-tert-butoxyphenyl group. In a non-limiting aspect, each $R^{1s}$, $R^{2s}$, $R^{11s}$, $R^{12s}$, $R^{13s}$, and/or $R^{14s}$ independently can be a phenyl group, a 2-halophenyl group, a 4-halophenyl group, or a 2,6-dihalophenylgroup. Generally, the halides of a dihalophenyl group can be the same, or alternatively, the halides can be different. In some aspects, each $R^{1s}$, $R^{2s}$, $R^{11s}$, $R^{12s}$, $R^{13s}$, and/or $R^{14s}$ independently can be a phenyl group, a 2-fluorophenyl group, a 4-fluorophenyl group, or a 2,6-difluorophenyl group.

In an aspect, each $R^{1s}$, $R^{2s}$, $R^{11s}$, $R^{12s}$, $R^{13s}$, and/or $R^{14s}$ independently can be a benzyl group or a substituted benzyl group; alternatively, a benzyl group; or alternatively, a substituted benzyl group. Each substituent of a substituted benzyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen, alternatively, a hydrocarbyl group; or alternatively, a hydrocarboxy group. Substituent halogens, substituent hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted benzyl group (general or specific) which can be utilized as $R^{1s}$, $R^{2s}$, $R^{11s}$, $R^{12s}$, $R^{13s}$, and/or $R^{14s}$.

In further aspects, two geminal $R^{1s}$s, two geminal $R^{2s}$s, geminal $R^{11s}$ and $R^{12s}$, and/or geminal $R^{13S}$ and $R^{14s}$ independently can be joined to form a ring or a ring system containing the heteroatom to which they are attached. The joining of two geminal $R^{1s}$s can be designated $L^{11s}$. The joining of two geminal $R^{2s}$s can be designated $L^{22s}$. The joining of geminal $R^{11s}$ and $R^{12s}$ can be designated $L^{12s}$. The joining of geminal $R^{13s}$ and $R^{14s}$ can be designated $L^{34s}$. In an aspect, $L^{11s}$, $L^{22s}$, $L^{12s}$, and/or $L^{34s}$ independently can be an organylene group; alternatively, an organylene group consisting of inert functional groups; alternatively, a hydrocarbylene group; or alternatively, an alkylene group. In an aspect, the $L^{11s}$, $L^{22s}$, $L^{12s}$, and/or $L^{34s}$ organylene group, when present, independently can be a $C_4$ to $C_{30}$, a $C_4$ to $C_{20}$, a $C_4$ to $C_{15}$, or a $C_4$ to $C_{10}$ organylene group. In some aspects, the $L^{11s}$, $L^{22s}$, $L^{12s}$, and/or $L^{34s}$ organylene group consisting of inert functional groups, when present, independently can be a $C_4$ to $C_{30}$, a $C_4$ to $C_{20}$, a $C_4$ to $C_{15}$, or a $C_4$ to $C_{10}$ organylene group consisting of inert functional groups. In other aspects, the $L^{11s}$, $L^{22s}$, $L^{12s}$, and/or $L^{34s}$ hydrocarbyl group, when present, independently can be a $C_4$ to $C_{30}$, a $C_4$ to $C_{20}$, a $C_4$ to $C_{15}$, or a $C_4$ to $C_{10}$ hydrocarbylene group. In a further aspect, the $L^{11s}$, $L^{22s}$, $L^{12s}$, and/or $L^{34s}$ alkylene group, when present, independently can be a $C_4$ to $C_{30}$, a $C_4$ to $C_{20}$, a $C_4$ to $C_{15}$, or a $C_4$ to $C_{10}$ alkylene group. In an aspect, $L^{11s}$, $L^{22s}$, $L^{12s}$, and/or $L^{34s}$, when present, independently can be a can be but-1,4-ylene group, a 1,4-diphenylbut-1,4-ylene group, a 1,4-di(2-methylphenyl)but-1,4-ylene group, 1,4-di(4-methylphenyl)but-1,4-ylene group, 1,4-di(4-t-butylphenyl)but-1,4-ylene group, a 1,4-di(3,5-dimethylphenyl)but-1,4-ylene group, a pent-1,4-ylene group, a 1-phenylpenta-1,4-ylene group, a 4-phenylpenta-1,4-ylene group, a hex-2,5-ylene group, a 2,2'-biphenylene group, a 2,2'-(methandiyl)dipheylene group, or a 2,2'-(1,2-ethandiyl)diphenylene group.

Generally, $R^{5s}$, of any heteroatomic ligand structure depicted herein and any heteroatomic ligand chromium compound complex depicted herein having an $R^{5s}$ group, can be an organyl group; alternatively, an organyl group consisting of inert functional groups; or alternatively, a hydrocarbyl group. In an aspect, the $R^{5s}$ organyl group can be a $C_1$ to $C_{20}$, a $C_1$ to $C_{15}$, a $C_1$ to $C_{10}$, or a $C_1$ to $C_5$ organyl group. In an aspect, the $R^{5s}$ organyl group consisting of inert functional groups can be a $C_1$ to $C_{20}$, a $C_1$ to $C_{15}$, a $C_1$ to $C_{10}$, or a $C_1$ to $C_5$ organyl group consisting of inert functional groups. In an aspect, the $R^{5s}$ hydrocarbyl group can be a $C_1$ to $C_{20}$, a $C_1$ to $C_{15}$, a $C_1$ to $C_{10}$, or a $C_1$ to $C_5$ hydrocarbyl group.

In an aspect, $R^{5s}$, of any heteroatomic ligand structure depicted herein and any heteroatomic ligand chromium compound complex depicted herein having an $R^{5s}$ group, can be an alkyl group, a substituted alkyl group, a cycloalkyl group, a substituted cycloalkyl group, an aryl group, a substituted aryl group, an aralkyl group, or a substituted aralkyl group; can be an alkyl group or a substituted alkyl group; alternatively, a cycloalkyl group or a substituted cycloalkyl group; alternatively, an aryl group or a substituted aryl group; alternatively, an aralkyl group or a substituted aralkyl group; or alternatively, an alkyl group, a cycloalkyl group, an aryl group, or an aralkyl group. In other aspects, $R^{5s}$ of any heteroatomic ligand structure depicted herein and any heteroatomic ligand chromium compound complex depicted herein having an $R^{5s}$ group, can be an alkyl group; alternatively, a substituted alkyl group, alternatively, a cycloalkyl group; alternatively, a substituted cycloalkyl group; alternatively, an aryl group; alternatively, a substituted aryl group; alternatively, an aralkyl group; or alternatively, a substituted aralkyl group. In any aspect disclosed herein, the $R^{5s}$ alkyl group can be a $C_1$ to $C_{20}$, a $C_1$ to $C_{15}$, or a $C_1$ to $C_{10}$ alkyl group. In any aspect disclosed herein, the $R^{5s}$ substituted alkyl group can be a $C_1$ to $C_{20}$, a $C_1$ to $C_{15}$, or a $C_1$ to $C_{10}$ substituted alkyl group. In any aspect disclosed herein, the $R^{5s}$ cycloalkyl group can be a $C_4$ to $C_{20}$, a $C_4$ to $C_{15}$, or a $C_4$ to $C_{10}$ cycloalkyl group. In any aspect disclosed herein, the $R^{5s}$ substituted cycloalkyl group can be a $C_4$ to $C_{20}$, a $C_4$ to, or a $C_4$ to $C_{10}$ substituted cycloalkyl group. In any aspect disclosed herein, the $R^{5s}$ aryl group can be a $C_6$ to $C_{20}$, a $C_6$ to $C_{15}$, or a $C_6$ to $C_{10}$ aryl group. In any aspect disclosed herein, the $R^{5s}$ substituted aryl group can be a $C_6$ to $C_{20}$, a $C_6$ to $C_{15}$, or a $C_6$ to $C_{10}$ substituted aryl group. In any aspect disclosed herein, the $R^{5s}$ aralkyl group can be a $C_7$ to $C_{20}$, a $C_7$ to $C_{15}$, or a $C_7$ to $C_{10}$ aralkyl group. In any aspect disclosed herein, the $R^{5s}$ substituted aralkyl group can be a $C_7$ to $C_{20}$, a $C_7$ to $C_{15}$, or a $C_7$ to $C_{10}$ substituted aralkyl group. Each substituent of a substituted alkyl group (general or specific), substituted cycloalkyl group (general or specific), substituted aryl group (general or specific), and/or substituted aralkyl group (general or specific) can be a halogen, hydrocarbyl group, or a hydrocarboxy group; alternatively, a halogen or a hydrocarbyl group; alternatively, a halogen or a hydrocarboxyl group; alternatively, a hydrocarbyl group or a hydrocarboxy group; alternatively, a halogen; alternatively, a hydrocarbyl group; or alternatively, a hydrocarboxy group. Substituent halogens, hydrocarbyl groups (general and specific), and substituent hydrocarboxy groups (general and specific) are independently disclosed herein. These substituent halogens, substituent hydrocarbyl groups, and substituent hydrocarboxy groups can be utilized without limitation to further describe a substituted group (general or specific) which can be utilized $R^{5s}$.

In an aspect, $R^{5s}$ can be a methyl group, an ethyl group, a propyl group, a butyl group, a pentyl group, a hexyl group, a heptyl group, or an octyl group; alternatively, a methyl group, an ethyl group, an n-propyl (1-propyl) group, an isopropyl (2-propyl) group, an n-butyl (1-butyl) group, a sec-butyl (2-butyl) group, an isobutyl (2-methyl-1-propyl) group, a tert-butyl (2-methyl-2-propyl) group, an n-pentyl (1-pentyl) group, a 2-pentyl group, a 3-pentyl group, a 2-methyl-1-butyl group, a tert-pentyl (2-methyl-2-butyl) group, a 3-methyl-1-butyl group, a 3-methyl-2-butyl group, or a neo-pentyl (2,2-dimethyl-1-propyl) group; or alternatively, a methyl group, an ethyl group, an iso-propyl (2-propyl) group, a tert-butyl (2-methyl-2-propyl) group, or a neopentyl (2,2-dimethyl-1-propyl) group. In some aspects, the $R^{5s}$ alkyl groups can be substituted. Each substituent of a $R^{5s}$ substituted alkyl group independently can be a halogen or a hydrocarboxy group; alternatively, a halogen; or alternatively, a hydrocarboxy group. Substituent halogens and substituent hydrocarboxy groups (general and specific) are independently described herein and these substituent groups can be utilized without limitation to further describe a substituted alkyl group (general or specific) which can be utilized as $R^{5s}$.

In an aspect, $R^{5s}$ can be a cyclopentyl group, a substituted cyclopentyl group, a cyclohexyl group, a substituted cyclohexyl group; alternatively, a cyclopentyl group or a substituted cyclopentyl group; or alternatively, a cyclohexyl group or a substituted cyclohexyl group. In further aspects, $R^{5s}$ can be a 2-substituted cyclohexyl group, a 2,6-disubstituted cyclohexyl group, a 2-subsituted cyclopentyl group, or a 2,5-disubstituted cyclopentyl group; alternatively, a 2-substituted cyclohexyl group or a 2,6-disubstituted cyclohexyl group; alternatively, a 2-substituted cyclohexyl group or a 2,6-disubstituted cyclohexyl group; alternatively, a 2-subsituted cyclopentyl group or a 2,5-disubstituted cyclopentyl group; alternatively, a 2-substituted cyclohexyl group or a 2-subsituted cyclopentyl group; or alternatively, a 2,6-disubstituted cyclohexyl group or a 2,5-disubstituted cyclopentyl group. In an aspect, one or more substituents of a multi-substituted cycloalkyl group utilized as $R^{5s}$ can be the same or different; alternatively, all the substituents of a multi-substituted cycloalkyl group can be the same; or alternatively, all the substituents of a multi-substituted cycloalkyl group can be different. Each substituent of a cycloalkyl group (general or specific) having a specified number of ring carbon atoms independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted cycloalkyl group (general or specific) which can be utilized as $R^{5s}$.

In a non-limiting aspect, $R^{5s}$ can be a cyclohexyl group, a 2-alkylcyclohexyl group, or a 2,6-dialkylcyclohexyl group; or alternatively, a cyclopentyl group, a 2-alkylcyclopentyl group, or a 2,5-dialkylcyclopentyl group. Alkyl substituent groups (general and specific) are independently described herein and these alkyl substituent groups can be utilized, without limitation, to further describe alkylcyclohexyl groups (general or specific), dialkylcyclohexyl groups (general or specific), alkylcyclopentyl groups (general or specific), and/or dialkylcyclopentyl groups (general or specific) which can be utilized as $R^{5s}$. Generally, the alkyl substituents of a disubstituted cyclohexyl or cyclopentyl group can be the same, or alternatively, the alkyl substituents can be different. In some non-limiting aspects, $R^{5s}$ heteroatomic ligand structure provided herein, and/or any heteroatomic ligand chromium compound complex structure provided herein can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group. In other non-limiting aspects, $R^{5s}$ can be a 2-methylcyclohexyl group, a 2-ethylcyclohexyl group, a 2-isopropylcyclohexyl group, or a 2-tert-butylcyclohexyl group; or alternatively, a 2,6-dimethylcyclohexyl group, a 2,6-diethylcyclohexyl group, a 2,6-diisopropylcyclohexyl group, or a 2,6-di-tert-butylcyclohexyl group. In an aspect, $R^{5s}$ heteroatomic ligand structure provided herein, and/or any heteroatomic ligand chromium compound complex structure provided herein can be a cyclopentyl group, a 2-methylcyclopentyl group, a cyclohexyl group, or a 2-methylcyclohexyl group; alternatively, a cyclopentyl group or a cyclohexyl group; or alternatively, a 2-methylcyclopentyl group or a 2-methylcyclohexyl group.

In an aspect, $R^{5s}$ can be a phenyl group or a substituted phenyl group; alternatively, a phenyl group; or alternatively, a substituted phenyl group. In some aspects, $R^{5s}$ can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,4-disubstituted phenyl group or a 2,6-disubstituted phenyl group; alternatively, a 2-substituted phenyl group; alternatively, a 4-substituted phenyl group; alternatively, a 2,4-disubstituted phenyl group; alternatively, a 2,6-disubstituted phenyl group; or alternatively, a 2,4,6-trisubstituted phenyl group. In an aspect, one or more substituents of a multi-substituted phenyl group utilized as $R^{5s}$ can be the same or different; alternatively, all the substituents can be the same, or alternatively, all the substituents can be different. Each substituent of a substituted phenyl group (general or specific) independently can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Substituent halogens, substituent hydrocarbyl groups (general and specific), and substituent hydrocarboxy groups (general and specific) are independently described herein and these substituent groups can be utilized without limitation to further describe a substituted phenyl group (general or specific) which can be utilized as $R^{5s}$.

In a non-limiting aspect, $R^{5s}$ can be a phenyl group, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group, a 2,4-dialkylphenyl group, a 2,6-dialkylphenyl group, or a 2,4,6-trialkylphenyl group. Alkyl substituent groups (general and specific) are independently described herein and these alkyl substituent groups can be utilized, without limitation, to further describe any alkyl substituted phenyl group which can be utilized as $R^{5s}$. Generally, the alkyl substituents of dialkylphenyl groups (general of specific) or trialkylphenyl groups (general or specific) can be the same, or alternatively, the alkyl substituents can be different. In some non-limiting aspects, $R^{5s}$ can be a phenyl group, a 2-methylphenyl group, a 2-ethylphenyl group, a 2-n-propylphenyl group, a 2-isopropylphenyl group, a 2-tert-butylphenyl group, a 2,6-dimethylphenyl group, a 2,6-diethylphenyl group, a 2,6-di-n-propylphenyl group, a 2,6-diisopropylphenyl group, a 2,6-di-tert-butylphenyl group, a 2-isopropyl-6-methylphenyl group, or a 2,4,6-trimethylphenyl group; alternatively, a phenyl group, a 2-methylphenyl group, a 2,6-dimethylphenyl group, or a 2,4,6-trimethylphenyl group.

Generally, $L^{2s}$, of any heteroatomic ligand and/or any heteroatomic ligand chromium compound complex having an $L^{2s}$ group, can be an organylene group; alternatively, an organylene group consisting of inert functional groups; alternatively, a hydrocarbylene group; or alternatively, an alkylene group. In an aspect, the $L^{2s}$ organylene group can be a $C_1$ to $C_{20}$, a $C_1$ to $C_{15}$, or a $C_1$ to $C_{10}$ organylene group. In an aspect, the $L^{2s}$ organylene group consisting of inert functional groups can be a $C_1$ to $C_{20}$, a $C_1$ to $C_{15}$, or a $C_1$ to $C_{10}$ organylene group consisting of inert functional groups. In an aspect, the $L^{2s}$ alkylene group can be a $C_1$ to $C_{20}$, $C_1$ to $C_{15}$, or a $C_1$ to $C_{10}$ alkylene group.

In an aspect, $L^{2s}$ of any heteroatomic ligand and/or any heteroatomic ligand chromium compound complex having an $L^{2s}$ group can be —$(CR^{P}R^{P'})_m$— where each $R^P$ and $R^{P'}$ can independently be hydrogen, methyl, ethyl, propyl, isopropyl, or butyl groups and m can be an integer from 1 to 12.

In some aspects, $L^{2s}$ of any heteroatomic ligand and/or any heteroatomic ligand chromium compound complex having an $L^{2s}$ group can be a methylene group (—$CH_2$—), an eth-1,2-ylene group (—$CH_2CH_2$—), a prop-1,3-ylene group (—$CH_2CH_2CH_2$—), a prop-1,2-ylene group (—$CH(CH_3)CH_2$—), a prop-2,2-ylene group (—$C(CH_3)_2$—), a but-1,4-ylene group (—$CH_2CH_2CH_2CH_2$—), or a 2-methylprop-1,3-ylene group (—$CH_2CH(CH_3)CH_2$—); or alternatively a methylene group (—$CH_2$—), an eth-1,2-ylene group (—$CH_2CH_2$—), or a prop-1,2-ylene group (—$CH(CH_3)CH_2$—).

In an aspect, $L^{2s}$ of any heteroatomic ligand and/or any heteroatomic ligand chromium compound complex having an $L^{2s}$ group, can be 1,2-cyclohexylene, a substituted 1,2-cyclohexylene, 1,3-cyclohexylene, a substituted 1,3-cyclohexylene, 1,4-cyclohexylene, a substituted 1,4-cyclohexylene, 3,3'-bicyclohexylene, a substituted 3,3'-bicyclohexylene, 4,4'-bicyclohexylene, a substituted 4,4'-bicyclohexylene, bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)ethane, 1,2-bis(4-cyclohexylene)ethane, a substituted 1,2-bis(4-cyclohexylene)ethane, 1,2-bis(3-cyclohexylene)-propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)propane, a substituted 2,2-bis(3-cyclohexylene)propane, 2,2-bis(4-cyclohexylene)propane, or a substituted 2,2-bis(4-cyclohexylene)propane. In some aspects, $L^{2s}$ of any heteroatomic ligand and/or any heteroatomic ligand chromium compound complex having an $L^{2s}$ group can be a substituted 1,2-cyclohexylene, a substituted 1,3-cyclohexylene, a substituted 1,4-cyclohexylene, a substituted 3,3'-bicyclohexylene, a substituted 4,4'-bicyclohexylene, a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane. In an aspect, each substituent of a substituted cyclohexylene, a substituted bis(cyclohexylene)methane, a substituted bis(cyclohexylene)ethane, or a substituted 1,2-bis(3-cyclohexylene)propane which can be utilized as $L^{2s}$ can be a hydrocarbyl group. Substituent groups (general and specific) are independently disclosed herein and can be utilized without limitation to further describe a substituted cyclohexylene (general or specific), a substituted bis(cyclohexylene)methane (general or specific), a substituted bis(cyclohexylene)ethane (general or specific), or a substituted 1,2-bis(3-cyclohexylene)propane (general or specific) which can be utilized as $L^{2s}$.

In an aspect, $L^{2s}$ of any heteroatomic ligand and/or any heteroatomic ligand chromium compound complex having an $L^{2s}$ group can be 1,2-phenylene, a substituted 1,2-phenylene, 1,3-phenylene, a substituted 1,3-phenylene, 1,4-phenylene, a substituted 1,4-phenylene, 3,3'-biphenylene, a substituted 3,3'-biphenylene, 4,4'-biphenylene, a substituted 4,4'-biphenylene, bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some aspects, $L^{2s}$ of any heteroatomic ligand and/or any heteroatomic ligand chromium compound complex having an $L^{2s}$ group can be a substituted 1,2-phenylene, a substituted 1,3-phenylene, a substituted 1,4-phenylene, a substituted 3,3'-biphenylene, a substituted 4,4'-biphenylene, a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane. In an aspect, each substituent of a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$ can be a hydrocarbyl group. Substituent hydrocarbyl groups (general and specific) are independently disclosed herein and can be utilized without limitation to further describe a substituted phenylene (general or specific), a substituted biphenylene (general or specific), a substituted bis(phenylene)methane (general or specific), a substituted bis(phenylene)ethane (general or specific), and/or a substituted bis(phenylene)propane (general or specific) which can be utilized as $L^{2s}$.

Generally, $L^{3s}$ and/or $L^{4s}$, of any heteroatomic ligand and/or any heteroatomic ligand chromium compound complex having an $L^{3s}$ and/or $L^{4s}$ group, independently can be an organylene group; alternatively, an organylene group consisting of inert functional groups; alternatively, a hydrocarbylene group; alternatively, an alkylene group. In an aspect, the $L^{3s}$ and/or $L^{4s}$ organylene group independently can be a $C_1$ to $C_{20}$, a $C_1$ to $C_{15}$, or a $C_1$ to $C_{10}$ organylene group. In an aspect, the $L^{3S}$ and/or $L^{4s}$ organylene group consisting of inert functional groups independently can be a $C_1$ to $C_{20}$, a $C_1$ to $C_{15}$, or a $C_1$ to $C_{10}$ organylene group consisting of inert functional groups. In an aspect, the $L^{3s}$ and/or $L^{4s}$ hydrocarbylene group independently can be a $C_1$ to $C_{20}$, a $C_1$ to $C_{15}$, or a $C_1$ to $C_{10}$ hydrocarbylene group. In an aspect, the $L^{3s}$ and/or $L^{4s}$ alkylene group independently can be a $C_1$ to $C_{20}$, $C_1$ to $C_{15}$, or a $C_1$ to $C_{10}$ alkylene group.

In an aspect, $L^{3s}$ and/or $L^{4s}$ of any heteroatomic ligand structure and/or any heteroatomic ligand chromium compound complex having an $L^{3s}$ and/or $L^{4s}$ group independently can be $-(CR^PR^{P'})_m-$ where each $R^P$ and $R^{P'}$ can independently be hydrogen, methyl, ethyl, propyl, isopropyl, or butyl groups and m can be an integer from 1 to 12. In some aspects, $L^{3s}$ and/or $L^{4s}$ of any heteroatomic ligand structure and/or any heteroatomic ligand chromium compound complex having an $L^{3s}$ and/or $L^{4s}$ group independently can be a methylene group ($-CH_2-$), an eth-1,2-ylene group ($-CH_2CH_2-$), an ethen-1,2-ylene group ($-CH=CH-$), a prop-1,3-ylene group ($-CH_2CH_2CH_2-$), a prop-1,2-ylene group ($-CH(CH_3)CH_2-$), a prop-2,2-ylene group ($-C(CH_3)_2-$), a 1-methylethen-1,2-ylene group ($-C(CH_3)=CH-$), a but-1,4-ylene group ($-CH_2CH_2CH_2-CH_2-$), a but-1,3-ylene group ($-CH_2CH_2CH(CH_3)-$), a but-2,3-ylene group ($-CH(CH_3)CH(CH_3)-$), a but-2-en-2,3-ylene group ($-C(CH_3)C(CH_3)-$), a 3-methylbut-1,3-ylene group ($-CH_2CH_2C(CH_3)_2-$), a 1,2-cyclopentylene group, a 1,2-cyclohexylene group, or a phen-1,2-ylene group; alternatively, a methylene group ($-CH_2-$), an eth-1,2-ylene group ($-CH_2CH_2-$), a prop-1,3-ylene group ($-CH_2CH_2CH_2-$), a prop-1,2-ylene group ($-CH(CH_3)CH_2-$), a prop-2,2-ylene group ($-C(CH_3)_2-$), a but-1,4-ylene group ($-CH_2CH_2CH_2-CH_2-$), a but-1,3-ylene group ($-CH_2CH_2CH(CH_3)-$), a but-2,3-ylene group ($-CH(CH_3)CH(CH_3)-$), a 1,2-cyclopentylene group, a 1,2-cyclohexylene group, or a phen-1,2-ylene group; or alternatively, an eth-1,2-ylene group ($-CH_2CH_2-$), a prop-1,3-ylene group ($-CH_2CH_2CH_2-$), a prop-1,2-ylene group ($-CH(CH_3)CH_2-$), a but-1,3-ylene group ($-CH_2CH_2CH(CH_3)-$), a but-2,3-ylene group ($-CH(CH_3)CH(CH_3)-$), a 1,2-cyclopentylene group, a 1,2-cyclohexylene group, or a phen-1,2-ylene group.

Various aspects described herein refer to non-hydrogen substituents such as halogen (or halo, halide), hydrocarbyl, hydrocarboxy, alkyl, and/or alkoxy substituents. In an aspect, each non-hydrogen substituent of any aspect calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. Each hydrocarbyl substituent independently can be a $C_1$ to $C_{10}$ hydrocarbyl group; or alternatively, a $C_1$ to $C_5$ hydrocarbyl group. Each hydrocarboxy substituent independently can be a $C_1$ to $C_{10}$ hydrocarboxy group; or alternatively, a $C_1$ to $C_5$ hydrocarboxy group. Each halide substituent independently can be a fluoride, chloride, bromide, or iodide; alternatively, a fluoride or chloride; alternatively, a fluoride; alternatively, a chloride; alternatively, a bromide; or alternatively, an iodide.

In an aspect, any hydrocarbyl substituent independently can be an alkyl group, an aryl group, or an aralkyl group; alternatively, an alkyl group; alternatively, an aryl group; or alternatively, an aralkyl group. In an aspect, any alkyl substituent independently can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an aspect, any aryl substituent independently can be phenyl group, a tolyl group, a xylyl group, or a 2,4,6-trimethylphenyl group; alternatively, a phenyl group; alternatively, a tolyl group; alternatively, a xylyl group; or alternatively, a 2,4,6-trimethylphenyl group. In an aspect, any aralkyl substituent independently can be benzyl group or an ethylphenyl group (2-phenyleth-1-yl or 1-phenyleth-1-yl); alternatively, a benzyl group; alternatively, an ethylphenyl group; alternatively, a 2-phenyleth-1-yl group; or alternatively, a 1-phenyleth-1-yl group.

In an aspect, any hydrocarboxy substituent independently can be an alkoxy group, an aryloxy group, or an aralkoxy group; alternatively, an alkoxy group; alternatively, an aryloxy group, or an aralkoxy group. In an aspect, any alkoxy substituent independently can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an aspect, any aryloxy substituent independently can be phenoxy group, a toloxy group, a xyloxy group, or a 2,4,6-trimethylphenoxy group; alternatively, a phenoxy group; alternatively, a toloxy group; alternatively, a xyloxy group; or alternatively, a 2,4,6-trimethylphenoxy group. In an aspect, any aralkoxy substituent independently can be benzoxy group.

Generally, the chromium compound or the chromium compound of the heteroatomic ligand chromium compound complexes described herein can have formula $CrX_p$ where X represents a monoanionic ligand, and p represents the number of monoanionic ligands (and the oxidation state of the chromium in the chromium compound). The monoanionic ligand (X) and p are independent elements of the chromium compound or the chromium compound of the heteroatomic ligand chromium compound complexes described herein and are independently described herein. The independent descriptions of the monoanionic ligand (X) and p can be utilized without limitation, and in any combination, to further describe the chromium compound or the chromium compound of the heteroatomic ligand chromium compound complexes described herein.

Generally, the chromium atom of the chromium compound ($CrX_p$) can have any positive oxidation state available to a chromium atom. In an aspect, the chromium atom can have an oxidation state of from +2 to +6; alternatively, from +2 to +4; or alternatively, from +2 to +3. In some aspects, the chromium atom of the chromium compound ($CrX_p$) can have an oxidation state of +1; alternatively, +2; alternatively, +3; or alternatively, +4.

The monoanion (X) of the chromium compound can be any monoanion. In an aspect, the monoanion (X) can be a halide, a carboxylate, a β-diketonate, a hydrocarboxide, a nitrate, or a chlorate. In some aspects, the monoanion (X) can be a halide, a carboxylate, a β-diketonate, or a hydrocarboxide. In any aspect, the hydrocarboxide can be an alkoxide, an aryloxide, or an aralkoxide. Generally, hydrocarboxide (and subdivisions of hydrocarboxide) are the anion analogues of the hydrocarboxy group. In other aspects, the monoanion (X) can be a halide, a carboxylate, a β-diketonate, or an alkoxide; or alternatively, a halide or a β-diketonate. In other aspects, the monoanion (X) can be a halide; alternatively, a carboxylate; alternatively, a β-diketonate; alternatively, a hydrocarboxide; alternatively, an alkoxide; or alternatively, an aryloxide. Generally, when the heteroatomic ligand of the heteroatomic ligand chromium compound complex is a neutral heteroatomic ligand the number of monoanions (p) can equal the oxidation state of the chromium atom. When the heteroatomic ligand of the heteroatomic ligand chromium compound complex is an anionic heteroatomic ligand the number of monoanions (p) can equal one less than the oxidation state of the chromium atom. In an aspect, the number of monoanions can be from 2 to 6; alternatively, from 2 to 4; alternatively, from 2 to 3; alternatively, 1; alternatively, 2; alternatively, 3; or alternatively, 4.

Generally, each halide of the chromium compound independently can be fluorine, chlorine, bromine, or iodine; or alternatively, chlorine, bromine, or iodine. In an aspect, each halide monoanion of the chromium compound can be chlorine; alternatively, bromine; or alternatively, iodine.

Generally, each carboxylate of the chromium compound independently can be a $C_1$ to $C_{20}$ carboxylate; or alternatively, a $C_1$ to $C_{10}$ carboxylate. In an aspect, each carboxylate of the chromium compound independently can be acetate, a propionate, a butyrate, a pentanoate, a hexanoate, a heptanoate, an octanoate, a nonanoate, a decanoate, an undecanoate, or a dodecanoate; or alternatively, a pentanoate, a hexanoate, a heptanoate, an octanoate, a nonanoate, a decanoate, an undecanoate, or a dodecanoate. In some aspects, each carboxylate of the chromium compound independently can be acetate, propionate, n-butyrate, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, valerate (n-pentanoate), neo-pentanoate, capronate (n-hexanoate), n-heptanoate, caprylate (n-octanoate), 2-ethylhexanoate, n-nonanoate, caprate (n-decanoate), n-undecanoate, or laurate (n-dodecanoate); alternatively, capronate (n-hexanoate); alternatively, n-heptanoate; alternatively, caprylate (n-octanoate);

or alternatively, 2-ethylhexanoate. In some aspects, the carboxylate of the chromium compound can be triflate (trifluoroacetate).

Generally, each β-diketonate of the chromium compound independently can be any $C_1$ to $C_{20}$ a β-diketonate; or alternatively, any $C_1$ to $C_{10}$ β-diketonate. In an aspect, each β-diketonate of the chromium compound independently can be acetylacetonate (i.e., 2,4-pentanedionate), hexafluoroacetylacetonate (i.e., 1,1,1,5,5,5-hexafluoro-2,4-pentanedionate), or benzoylacetonate; alternatively, acetylacetonate; alternatively, hexafluoroacetylacetonate; or alternatively, benzoylacetonate.

Generally, each hydrocarboxide of the chromium compound independently can be any $C_1$ to $C_{20}$ hydrocarboxide; or alternatively, any $C_1$ to $C_{10}$ hydrocarboxide. In an aspect, each hydrocarboxide of the chromium compound independently can be a $C_1$ to $C_{20}$ alkoxide; alternatively, a $C_1$ to $C_{10}$ alkoxide; alternatively, a $C_6$ to $C_{20}$ aryloxide; or alternatively, a $C_6$ to $C_{10}$ aryloxide. In an aspect, each alkoxide of the chromium compound independently can be methoxide, ethoxide, a propoxide, or a butoxide; alternatively, methoxide, ethoxide, isopropoxide, or tert-butoxide; alternatively, methoxide; alternatively, an ethoxide; alternatively, an isopropoxide; or alternatively, a tert-butoxide. In an aspect, the aryloxide can be phenoxide.

In some non-limiting aspects, the chromium compound and/or the chromium compound of the heteroatomic ligand chromium compound complex can comprise, can consist essentially of, or consist of, a chromium(II) halide, a chromium(II) carboxylate, or a chromium(II) β-diketonate; or alternatively, a chromium(III) halide, a chromium(III) carboxylate, or a chromium(III) β-diketonate. In other non-limiting aspects, the chromium compound and/or the chromium compound of the heteroatomic ligand chromium compound complex can comprise, can consist essentially of, or consist of, a chromium(II) halide; alternatively, a chromium(III) halide; alternatively, a chromium (II) carboxylate; alternatively, a chromium(III) carboxylate; alternatively, a chromium(II) β-diketonate; or alternatively, a chromium(III) β-diketonate. Halides, carboxylates, β-diketonates are independently described herein and these halides, carboxylates, β-diketonate and these independently described halides, carboxylates, β-diketonates can be utilized without limitation and in any combination to further described the chromium compound and/or the chromium compound of the heteroatomic ligand chromium compound complex. In further non-limiting aspects, the chromium compound and/or the chromium compound of the heteroatomic ligand chromium compound complex can comprise, can consist essentially of, or consist of, chromium(II) chloride, chromium(III) chloride, chromium(II) fluoride, chromium(III) fluoride, chromium(II) bromide, chromium(III) bromide, chromium (II) iodide, chromium(III) iodide, chromium(II) acetate, chromium(III) acetate, chromium(II) 2-ethylhexanoate, chromium(III) 2-ethylhexanoate, chromium(II) triflate, chromium(III) triflate, chromium(II) nitrate, chromium(III) nitrate, chromium(II) acetylacetonate, chromium(III) acetylacetonate, chromium(II) hexafluoracetylacetonate, chromium(III) hexafluoracetylacetonate, chromium(III) benzoylacetonate, or chromium(III) benzoylacetonate; alternatively, chromium(III) chloride, chromium(III) fluoride, chromium(III) bromide, chromium(III) iodide, chromium(III) chloride (THF) complex, chromium(III) acetate, chromium(III) 2-ethylhexanoate, chromium(III) triflate, chromium(III) nitrate, chromium(III) acetylacetonate, chromium(III) hexafluoracetylacetonate, or chromium(III) benzoylacetonate; alternatively, chromium(III) chloride, or chromium(III) acetylacetonate; alternatively, chromium(III) chloride; or alternatively, chromium(III) acetylacetonate.

In a non-limiting aspect, the heteroatomic ligand chromium compound complex can be selected from any one or more of a heteroatomic ligand chromium compound complex having i) Structure NPFCr1 where $R^1$ is 2,6-dimethylphenyl, $R^3$ is H, $R^4$ and $R^5$ are isopropyl, and X is chlorine; $R^1$ is 2,6-dimethylphenyl, $R^3$ is H, $R^4$ and $R^5$ are phenyl, and X is chlorine; $R^1$ is 2,6-dimethylphenyl, $R^3$ is H, $R^4$ and $R^5$ are 4-methoxyphenyl, and X is chlorine; $R^1$ is 2,4,6-trimethylphenyl, $R^3$ is H, $R^4$ and $R^5$ are isopropyl, and X is chlorine; $R^1$ is 2,4,6-trimethylphenyl, $R^3$ is H, $R^4$ and $R^5$ are phenyl, and X is chlorine; and $R^1$ is 2,4,6-trimethylphenyl, $R^3$ is H, $R^4$ and $R^5$ are 4-methoxyphenyl, and X is chlorine: ii) Structure NPACr1 where $R^1$ is 2,6-dimethylphenyl, $R^2$ is phenyl, $R^3$ is H, $R^4$ and $R^5$ are isopropyl, and X is chlorine; $R^1$ is 2,4,6-trimethylphenyl, $R^2$ is phenyl, $R^3$ is H, $R^4$ and $R^5$ are isopropyl, and X is chlorine; $R^1$ is 2,6-dimethylphenyl, $R^2$ is phenyl, $R^3$ is H, $R^4$ and $R^5$ are phenyl, and X is chlorine; $R^1$ is 2,4,6-trimethylphenyl, $R^2$ is phenyl, $R^3$ is H, $R^4$ and $R^5$ are phenyl, and X is chlorine; $R^1$ is 2,6-dimethylphenyl, $R^2$ is 4-methylbenzyl, $R^3$ is H, $R^4$ and $R^5$ are phenyl, and X is chlorine; $R^1$ is 2,6-dimethylphenyl, $R^2$ is phenyl, $R^3$ is H, $R^4$ and $R^5$ are 4-methoxyphenyl, and X is chlorine; $R^1$ is 2,6-dimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-t-butylphenyl, $R^3$ is H, $R^4$ and $R^5$ are methyl, and X is chlorine; $R^1$ is 2,4,6-trimethylphenyl, $R^2$ is 4-methylbenzyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are phenyl, and X is chlorine; $R^1$ is 3,5-dimethylphenyl, $R^2$ is phenyl, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are 4-methoxyphenyl, and X is chlorine; $R^1$ is 2,4,6-trimethylphenyl, $R^2$ is 4-methylbenzyl, $R^3$ is H, $R^4$ is t-butyl, $R^5$ is phenyl, and X is chlorine; $R^1$ is 2,4,6-trimethylphenyl, $R^2$ is 4-methylbenzyl, $R^3$ is H, $R^4$ is methyl, $R^5$ is phenyl, and X is chlorine; $R^1$ and $R^2$ are joined to form a prop-1,3-ylene group, $R^3$ is H, $R^4$ and $R^5$ are isopropyl, and X is chlorine; $R^1$ and $R^2$ are joined to form a but-1,4-ylene group, $R^3$ is H, $R^4$ and $R^5$ are isopropyl, and X is chlorine; $R^1$ is 2,4,6-trimethylphenyl, $R^2$ is 4-methylbenzyl, $R^3$ is H, $R^4$ and $R^5$ are joined to form a but-1,4-ylene group, and X is chlorine; $R^1$ is 2,4,6-trimethylphenyl, $R^2$ is 4-methylbenzyl, $R^3$ is H, $R^4$ and $R^5$ are joined to form a 2,2'-dimethylbiphenylene group, and X is chlorine: iii) Structure GUCr1 where $R^1$ is 2-methylphenyl, $R^{2a}$ is 2-methylphenyl, $R^{2b}$ is H, $R^3$ is H, $R^4$ and $R^5$ are isopropyl, and X is chlorine; $R^1$ is 2,6-dimethylphenyl, $R^{2a}$ is phenyl, $R^{2b}$ is H, $R^3$ is H, $R^4$ and $R^5$ are isopropyl, and X is chlorine; $R^1$ is 2,6-dimethylphenyl, $R^{2a}$ is phenyl, $R^{2b}$ is H, $R^3$ is H, $R^4$ and $R^5$ are phenyl, and X is chlorine; $R^1$ is 2,6-dimethylphenyl, $R^{2a}$ and $R^{2b}$ are phenyl, $R^3$ is H, $R^4$ and $R^5$ are isopropyl, and X is chlorine: iv) Structure GUCr4 where $L^{12}$ is prop-1,3-ylene, $L^{23}$ is prop-1, 3-ylene, $R^4$ and $R^5$ are isopropyl, and X is chlorine; $L^{12}$ is prop-1,3-ylene, $L^{23}$ is prop-1,3-ylene, $R^4$ and $R^5$ are cyclopentyl, and X is chlorine; $L^{12}$ is prop-1,3-ylene, $L^{23}$ is prop-1,3-ylene, $R^4$ and $R^5$ are cyclohexyl, and X is chlorine; $L^{12}$ is prop-1,3-ylene, $L^{23}$ is prop-1,3-ylene, $R^4$ and $R^5$ are phenyl, and X is chlorine; $L^{12}$ is but-1,3-ylene, $L^{23}$ is prop-1,3-ylene, $R^4$ and $R^5$ are isopropyl, and X is chlorine; $L^{12}$ is but-1,3-ylene, $L^{23}$ is prop-1,3-ylene, $R^4$ and $R^5$ are cyclopentyl, and X is chlorine; $L^{12}$ is but-1,3-ylene, $L^{23}$ is but-1,3-ylene, $R^4$ and $R^5$ are isopropyl, and X is chlorine; $L^{12}$ is but-1,3-ylene, $L^{23}$ is but-1,3-ylene, $R^4$ and $R^5$ are phenyl, and X is chlorine; $L^{12}$ is ethen-1,2-ylene, $L^{23}$ is prop-1,3-ylene, $R^4$ and $R^5$ are isopropyl, and X is chlorine; $L^{12}$ is ethen-1,2-ylene, $L^{23}$ is prop-1,3-ylene, $R^4$ and $R^5$ are cyclopentyl, and X is chlorine; $L^{12}$ is ethen-1,2-ylene, $L^{23}$ is prop-1,3-ylene, $R^4$ and $R^5$ are cyclohexyl, and X is chlorine; $L^{12}$ is phen-1,2-ylene, $L^{23}$ is eth-1,2-ylene, $R^4$ and $R^5$ are isopropyl, and X is chlorine: and v) Structure HCPACr2 where T is sulfur, $L^{12}$ is ethen-1,2-ylene, $R^3$ is H, $R^4$ and $R^5$ are isopropyl, and X is chlorine; and T is sulfur, $L^{12}$ is phen-1,2-ylene, $R^3$ is H, $R^4$ and $R^5$ are isopropyl, and X is chlorine.

In a non-limiting aspect, the heteroatomic ligand can be any one or more of HL 1, HL 2, HL 3, HL 4. HL 5, HL 6, HL 7, HL 7, and HL 9. In some non-limiting aspects, the diphosphino amine chromium compound complex can be a chromium compound complex of any one or more of HLCr 1, HLCr 2, HLCr 3, HLCr 4, HLCr 5, HLCr 6, HLCr 7, HLCr 8, and HLCr 9. In other non-limiting aspects, the diphosphino amine chromium compound complex can be a chromium(III) chloride or chromium(III) acetylacetonate complex of any one or more of HLCr 1, HLCr 2, HLCr 3, HLCr 4, HLCr 5, HLCr 6, HLCr 7, HLCr 8, and HLCr 9.

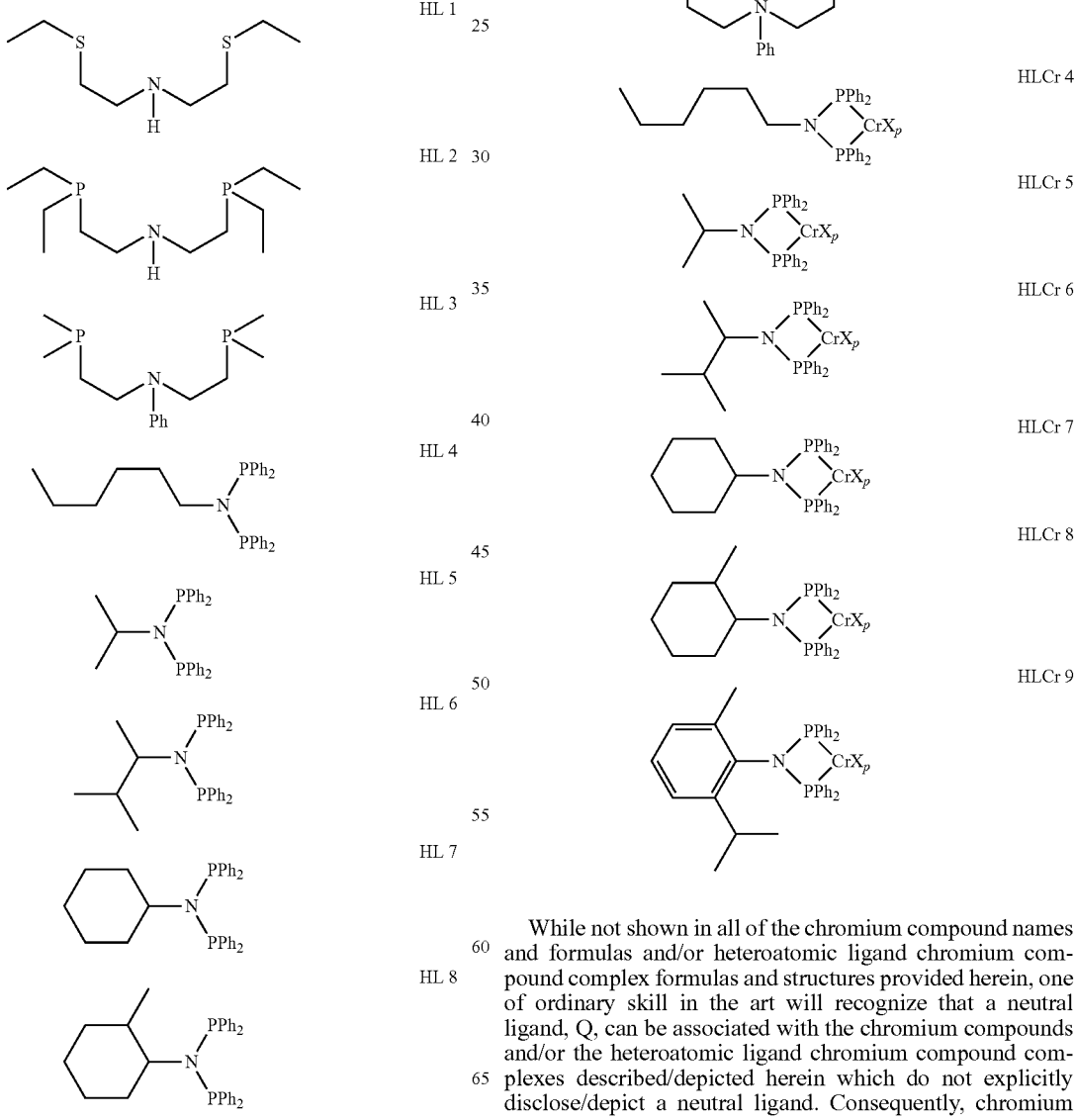

While not shown in all of the chromium compound names and formulas and/or heteroatomic ligand chromium compound complex formulas and structures provided herein, one of ordinary skill in the art will recognize that a neutral ligand, Q, can be associated with the chromium compounds and/or the heteroatomic ligand chromium compound complexes described/depicted herein which do not explicitly disclose/depict a neutral ligand. Consequently, chromium compounds and/or heteroatomic ligand chromium compound complexes having a neutral ligand, Q, can be considered as equivalent to the chromium compounds and/or heteroatomic ligand chromium compound complexes depicted herein not having the neutral ligand, Q. Additionally, it should be understood that while some of the chromium compounds and/or heteroatomic ligand chromium compound complexes described/depicted/provided herein do not formally show the presence of a neutral ligand, the chromium compounds and/or heteroatomic ligand chromium compound complexes having neutral ligands (e.g., nitriles and ethers, among others) are fully contemplated and encompassed herein as potential chromium compounds and/or heteroatomic ligand chromium compound complexes that can be utilized in the catalyst system used in aspects of the present disclosure.

Generally, the neutral ligand of any chromium compound and/or heteroatomic ligand chromium compound complex, when present, independently can be any neutral ligand that forms an isolatable compound with the chromium compound and/or heteroatomic ligand chromium compound complex. In an aspect, each neutral ligand independently can be a nitrile or an ether; alternatively, a nitrile; or alternatively, an ether. The number of neutral ligands, q, can be any number that forms an isolatable compound with the chromium compound, and/or heteroatomic ligand chromium compound complex. In an aspect, the number of neutral ligands can be from 0 to 6; alternatively, 0 to 3; alternatively, 0; alternatively, 1; alternatively, 2; alternatively, 3; or alternatively, 4.

Generally, each nitrile ligand independently can be a $C_2$ to $C_{20}$ nitrile; or alternatively, a $C_2$ to $C_{10}$ nitrile. In an aspect, each nitrile ligand independently can be a $C_2$ to $C_{20}$ aliphatic nitrile, a $C_7$ to $C_{20}$ aromatic nitrile, a $C_8$ to $C_{20}$ aralkane nitrile, or any combination thereof; alternatively, a $C_2$ to $C_{20}$ aliphatic nitrile; alternatively, a $C_7$ to $C_{20}$ aromatic nitrile; or alternatively, a $C_8$ to $C_{20}$ aralkane nitrile. In some aspects, each nitrile ligand independently can be a $C_2$ to $C_{10}$ aliphatic nitrile, a $C_7$ to $C_{10}$ aromatic nitrile, a $C_8$ to $C_{10}$ aralkane nitrile, or any combination thereof; alternatively, a $C_1$ to $C_{10}$ aliphatic nitrile; alternatively, a $C_7$ to $C_{10}$ aromatic nitrile; or alternatively, a $C_8$ to $C_{10}$ aralkane nitrile. In an aspect, each aliphatic nitrile independently can be acetonitrile, propionitrile, a butyronitrile, benzonitrile, or any combination thereof; alternatively, acetonitrile; alternatively, propionitrile; alternatively, a butyronitrile; or alternatively, benzonitrile.

Generally, each ether ligand independently can be a $C_2$ to $C_{40}$ ether; alternatively, a $C_2$ to $C_{30}$ ether; or alternatively, a $C_2$ to $C_{20}$ ether. In an aspect, each ether ligand independently can be a $C_2$ to $C_{40}$ aliphatic ether, a $C_3$ to $C_{40}$ aliphatic cyclic ether, a $C_4$ to $C_{40}$ aromatic cyclic ether; alternatively, a $C_2$ to $C_{40}$ aliphatic acyclic ether or a $C_3$ to $C_{40}$ aliphatic cyclic ether; alternatively, a $C_2$ to $C_{40}$ aliphatic acyclic ether; alternatively, a $C_3$ to $C_{40}$ aliphatic cyclic ether; or alternatively, a $C_4$ to $C_{40}$ aromatic cyclic ether. In some aspects, each ether ligand independently can be a $C_2$ to $C_{30}$ aliphatic ether, a $C_3$ to $C_{30}$ aliphatic cyclic ether, a $C_4$ to $C_{30}$ aromatic cyclic ether; alternatively, a $C_2$ to $C_{30}$ aliphatic acyclic ether or a $C_3$ to $C_{30}$ aliphatic cyclic ether; alternatively, a $C_2$ to $C_{30}$ aliphatic acyclic ether; alternatively, a $C_3$ to $C_{30}$ aliphatic cyclic ether; or alternatively, a $C_4$ to $C_{30}$ aromatic cyclic ether. In other aspects, each ether ligand independently can be a $C_2$ to $C_{20}$ aliphatic ether, a $C_3$ to $C_{20}$ aliphatic cyclic ether, a $C_4$ to $C_{20}$ aromatic cyclic ether; alternatively, a $C_2$ to $C_{20}$ aliphatic acyclic ether or a $C_3$ to $C_{20}$ aliphatic cyclic ether; alternatively, a $C_2$ to $C_{20}$ aliphatic acyclic ether; alternatively, a $C_3$ to $C_{20}$ aliphatic cyclic ether; or alternatively, a $C_4$ to $C_{20}$ aromatic cyclic ether. In some aspects, each ether ligand independently can be dimethyl ether, diethyl ether, a dipropyl ether, a dibutyl ether, methyl ethyl ether, a methyl propyl ether, a methyl butyl ether, tetrahydrofuran, a dihydrofuran, 1,3-dioxolane, tetrahydropyran, a dihydropyran, a pyran, a dioxane, furan, benzofuran, isobenzofuran, dibenzofuran, diphenyl ether, a ditolyl ether, or any combination thereof; alternatively, dimethyl ether, diethyl ether, a dipropyl ether, a dibutyl ether, methyl ethyl ether, a methyl propyl ether, a methyl butyl ether, or any combination thereof; tetrahydrofuran, a dihydrofuran, 1,3-dioxolane, tetrahydropyran, a dihydropyran, a pyran, a dioxane, or any combination thereof; furan, benzofuran, isobenzofuran, dibenzofuran, or any combination thereof; diphenyl ether, a ditolyl ether, or any combination thereof; alternatively, dimethyl ether; alternatively, diethyl ether; alternatively, a dipropyl ether; alternatively, a dibutyl ether; alternatively, methyl ethyl ether; alternatively, a methyl propyl ether; alternatively, a methyl butyl ether; alternatively, tetrahydrofuran; alternatively, a dihydrofuran; alternatively, 1,3-dioxolane; alternatively, tetrahydropyran; alternatively, a dihydropyran; alternatively, a pyran; alternatively, a dioxane; alternatively, furan; alternatively, benzofuran; alternatively, isobenzofuran; alternatively, dibenzofuran; alternatively, diphenyl ether; or alternatively, a ditolyl ether.

While the heteroatomic ligand chromium compound complex formulas and structures provided herein are shown as neutral complexes, one of ordinary skill in the art will recognize that heteroatomic ligand chromium compound complexes can comprise or can exist as "ate" complexes comprising a negatively charged heteroatomic ligand chromium compound complex and an associated positively charged metal or metal complex cation. Additionally, it should be understood that while the heteroatomic ligand chromium compound complexes described/depicted/provided herein are shown as neutral complexes, the "ate" complexes comprising a negatively charged heteroatomic ligand chromium compound complex and an associated positively charged metal or metal complex cation are implicitly and fully contemplated as potential heteroatomic ligand chromium compound complexes that can be utilized in the catalyst system used in aspects of the present disclosure.

Generally, the organoaluminum compound utilized in the catalyst systems disclosed herein can be any organoaluminum compound which in conjunction with the heteroatomic ligand chromium compound complex (or the chromium compound and heteroatomic ligand) can catalyze the formation of an oligomer product. In an aspect, the organoaluminum compound can comprise, can consist essentially of, or can be, an aluminoxane, an alkylaluminum compound, or any combination thereof; alternatively, an aluminoxane; or alternatively, an alkylaluminum compound. In an aspect, the alkylaluminum compound can comprise, can consist essentially of, or can be, a trialkylaluminum, an alkylaluminum halide, an alkylaluminum alkoxide, or any combination thereof. In some aspects, the alkylaluminum compound can comprise, can consist essentially of, or can be, a trialkylaluminum, an alkylaluminum halide, or any combination thereof; alternatively, a trialkylaluminum, an alkylaluminum alkoxide, or any combination thereof; or alternatively, a trialkylaluminum. In other aspects, the alkylaluminum compound can be a trialkylaluminum; alternatively, an alkylaluminum halide; or alternatively, an alkylaluminum alkoxide. In an aspect, the aluminoxane utilized in the catalyst systems which are utilized in the processes and systems can comprise, can consist essentially of, or can be, any aluminoxane which in conjunction with the heteroatomic ligand chromium compound complex (or the chromium compound and heteroatomic ligand) can catalyze the formation of an oligomer product. In a non-limiting aspect, the aluminoxane can have a repeating unit characterized by the Formula I:

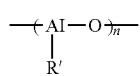

Formula I wherein R' is a linear or branched alkyl group. Alkyl groups of the aluminoxanes and alkylaluminum compounds are independently described herein and can be utilized without limitation to further describe the aluminoxanes having Formula I and/or the alkylaluminum compounds. Generally, n of Formula I can be greater than 1; or alternatively, greater than 2. In an aspect, n can range from 2 to 15; or alternatively, range from 3 to 10.

In an aspect, each halide of any alkylaluminum halide disclosed herein can independently be fluoride, chloride, bromide, or iodide; or alternatively, chloride, bromide, or iodide. In an aspect, each halide of any alkylaluminum halide disclosed herein can be fluoride; alternatively, chloride; alternatively, bromide; or alternatively, iodide.

In an aspect, each alkyl group of an aluminoxane and/or alkylaluminum compound independently can be a $C_1$ to $C_{20}$ alkyl group; alternatively, a $C_1$ to $C_{10}$ alkyl group; or alternatively, a $C_1$ to $C_6$ alkyl group. In an aspect, each alkyl group of an aluminoxane and/or alkylaluminum compound a methyl group, an ethyl group, a propyl group, a butyl group, a pentyl group, a hexyl group, a heptyl group, or an octyl group; alternatively, a methyl group, a ethyl group, a butyl group, a hexyl group, or an octyl group. In some aspects, each alkyl group of an aluminoxane and/or alkylaluminum compound can be a methyl group, an ethyl group, an n-propyl group, an n-butyl group, an iso-butyl group, an n-hexyl group, or an n-octyl group; alternatively, a methyl group, an ethyl group, an n-butyl group, or an iso-butyl group; alternatively, a methyl group; alternatively, an ethyl group; alternatively, an n-propyl group; alternatively, an n-butyl group; alternatively, an iso-butyl group; alternatively, an n-hexyl group; or alternatively, an n-octyl group.

In an aspect, each alkoxide group of any alkylaluminum alkoxide disclosed herein independently can be a $C_1$ to $C_{20}$ alkoxy group, a $C_1$ to $C_{10}$ alkoxy group, or a $C_1$ to $C_6$ alkoxy group. In an aspect, each alkoxide group of any alkylaluminum alkoxide disclosed herein independently can be a methoxy group, an ethoxy group, a propoxy group, a butoxy group, a pentoxy group, a hexoxy group, a heptoxy group, or an octoxy group; alternatively, a methoxy group, an ethoxy group, a butoxy group, a hexoxy group, or an octoxy group. In some aspects, each alkoxide group of any alkylaluminum alkoxide disclosed herein independently can be a methoxy group, an ethoxy group, an n-propoxy group, an n-butoxy group, an iso-butoxy group, an n-hexoxy group, or an n-octoxy group; alternatively, a methoxy group, an ethoxy group, an n-butoxy group, or an iso-butoxy group; alternatively, a methoxy group; alternatively, an ethoxy group; alternatively, an n-propoxy group; alternatively, an n-butoxy group; alternatively, an iso-butoxy group; alternatively, an n-hexoxy group; or alternatively, an n-octoxy group.

In a non-limiting aspect, useful trialkylaluminum compounds can include trimethylaluminum, triethylaluminum, tripropylaluminum, tributylaluminum, trihexylaluminum, trioctylaluminum, or mixtures thereof. In some non-limiting aspects, useful trialkylaluminum compounds can include trimethylaluminum, triethylaluminum, tripropylaluminum, tri-n-butylaluminum, tri-isobutylaluminum, trihexylaluminum, tri-n-octylaluminum, or mixtures thereof; alternatively, triethylaluminum, tri-n-butylaluminum, tri-isobutylaluminum, trihexylaluminum, tri-n-octylaluminum, or mixtures thereof; alternatively, triethylaluminum, tri-n-butylaluminum, trihexylaluminum, tri-n-octylaluminum, or mixtures thereof. In other non-limiting aspects, useful trialkylaluminum compounds can include trimethylaluminum; alternatively, triethylaluminum; alternatively, tripropylaluminum; alternatively, tri-n-butylaluminum; alternatively, tri-isobutylaluminum; alternatively, trihexylaluminum; or alternatively, tri-n-octylaluminum.

In a non-limiting aspect, useful alkylaluminum halides can include diethylaluminum chloride, diethylaluminum bromide, ethylaluminum dichloride, ethylaluminum sesquichloride, and mixtures thereof. In some non-limiting aspects, useful alkylaluminum halides can include diethylaluminum chloride, ethylaluminum dichloride, ethylaluminum sesquichloride, and mixtures thereof. In other non-limiting aspects, useful alkylaluminum halides can include diethylaluminum chloride; alternatively, diethylaluminum bromide; alternatively, ethylaluminum dichloride; or alternatively, ethylaluminum sesquichloride.

In a non-limiting aspect, the aluminoxane can be, comprise, or consist essentially of, methylaluminoxane (MAO), ethylaluminoxane, modified methylaluminoxane (MMAO), n-propylaluminoxane, iso-propyl-aluminoxane, n-butylaluminoxane, sec-butylaluminoxane, iso-butylaluminoxane, t-butylaluminoxane, 1-pentylaluminoxane, 2-entylaluminoxane, 3-pentyl-aluminoxane, iso-pentyl-aluminoxane, neopentylaluminoxane, or mixtures thereof. In some non-limiting aspects, the aluminoxane can be, comprise, or consist essentially of, methylaluminoxane (MAO), modified methylaluminoxane (MMAO), isobutyl aluminoxane, t-butyl aluminoxane, or mixtures thereof. In other non-limiting aspects, the aluminoxane can be, comprise, or consist essentially of, methylaluminoxane (MAO); alternatively, ethylaluminoxane; alternatively, modified methylaluminoxane (MMAO); alternatively, n-propylaluminoxane; alternatively, iso-propyl-aluminoxane; alternatively, n-butylaluminoxane; alternatively, sec-butylaluminoxane; alternatively, iso-butylaluminoxane; alternatively, t-butyl aluminoxane; alternatively, 1-pentyl-aluminoxane; alternatively, 2-pentylaluminoxane; alternatively, 3-pentyl-aluminoxane; alternatively, iso-pentyl-aluminoxane; or alternatively, neopentylaluminoxane.

The components of the catalyst system can be combined in any order, in any manner, and for any length of time (e.g., aging) to prepare the catalyst system. The catalyst system mixture can be aged for any suitable period of time (e.g., 5 sec to 48 hr, from 10 sec to 36 hr, from 30 sec to 24 hr, from 1 min to 18 hr, from 5 min to 6 hr, from 10 min to 4 hr, or from 20 min to 2 hr) in the substantial absence of ethylene prior to introducing the catalyst system mixture into the activation vessel. Herein, the substantial absence of ethylene means that the catalyst system mixture contains less than 1 wt. % ethylene, based on the total weight of the catalyst system mixture. In some instance, less than 0.5 wt. %, less than 0.1 wt. %, or less than 0.05 wt. % ethylene, based upon the total weight of the catalyst system mixture, is present in the catalyst system mixture prior to the activation vessel.

While not limited thereto, the catalyst system can be formed at a minimum temperature or −40° C., −20° C., 0° C., 10° C., 15° C., or 20° C.; alternatively or additionally, at a maximum temperature of 100° C., 75° C., 60° C., or 40°

C. Generally, the catalyst system can be formed at a temperature in a range from any minimum temperature disclosed herein to any maximum temperature disclosed herein. Accordingly, suitable non-limiting temperatures for forming the catalyst system can be in a range from −40° C. to 100° C., from −20° C. to 100° C., from 0° C. to 100° C., from 10° C. to 75° C., from 15° C. to 60° C., or from 20° C. to 40° C. In these and other aspects, these temperature ranges also are meant to encompass circumstances where the catalyst system is formed at a series of different temperatures, instead of at a single fixed temperature, falling within the respective ranges.

The Al to Cr molar ratio of the catalyst system (or in which the oligomer product is formed) can be in a range of 10:1 to 5,000:1, from 50:1 to 3,000:1, from 50:1 to 3,000:1, from 75:1 to 2,000:1, from 100:1 to 2,000:1, or from 100:1 to 1,000:1. If more than one complex and/or more than one organoaluminum are employed, the Al to Cr ratio is based on the total moles of chromium and/or aluminum.

Oligomerization Processes

Aspects of this disclosure are directed to ethylene oligomerization processes and the formation of an oligomer product. A first process can comprise (or consist essentially of, or consist of) a) forming a first mixture in an activation vessel, the first mixture comprising ethylene, a catalyst system comprising i) a heteroatomic ligand chromium compound complex and an organoaluminum compound, or ii) a heteroatomic ligand, a chromium compound, and an organoaluminum compound, optionally, a first organic reaction medium, and optionally, hydrogen; b) maintaining the first mixture in the activation vessel for an average residence time; c) introducing into a reaction zone: ethylene, the first mixture from step b), a second organic reaction medium, and optionally, hydrogen; and forming an oligomer product in the reaction zone. A second process consistent with this disclosure can comprise a) forming a first mixture in an activation vessel, the first mixture comprising 1) a first catalyst system comprising i) a first heteroatomic ligand chromium compound complex and a first organoaluminum compound, or ii) a first heteroatomic ligand, a first chromium compound, and a first organoaluminum compound, 2) a first feed comprising ethylene, a second catalyst system comprising i) a second heteroatomic ligand chromium compound complex and a second organoaluminum compound, or ii) a second heteroatomic ligand, a second chromium compound, and a second organoaluminum compound, a second organic reaction medium, a second oligomer product, and optionally hydrogen, 3) optionally, a first organic reaction medium, and 4) optionally, hydrogen; b) maintaining the first mixture in the activation vessel for an average residence time; c) introducing into a reaction zone: ethylene, the first mixture from step b), the second organic reaction medium, and optionally, hydrogen; and d) forming an oligomer product in the reaction zone. In an aspect, the process can further comprise discharging a reaction zone effluent comprising the oligomer product (or the second oligomer product); or alternatively, ethylene, a catalyst system (or a second catalyst system), an organic reaction medium (or a second organic reaction medium), an oligomer product (or a second oligomer product), and optionally hydrogen. In an aspect, a portion of a reaction zone effluent is fed to the activation vessel as the first feed.

In these first and second processes, the average residence time of the first mixture in the activation vessel can be in a range from 10 sec up to i) a period of time sufficient to form an amount of a first oligomer product in the activation vessel equal to 5%, 4%, 3%, 2%, or 1% of an amount of the oligomer product formed in the reaction zone; or ii) a conversion of ethylene in the activation vessel of 5 mol %, 4 mol %, 3 mol %, 2 mol %, 1 mol %, or 0.5 mol % of a total ethylene utilized in step a) and step c); or iii) a catalyst system productivity in the activation vessel of 5%, 4%, 3%, 2%, or 1% of a catalyst system productivity in the reaction zone; or iv) a fouling rate in the activation vessel of 0.065 mg/cm$^2$-hr, 0.06 mg/cm$^2$-hr, 0.055 mg/cm$^2$-hr, 0.05 mg/cm$^2$-hr, 0.045 mg/cm$^2$-hr, or 0.04 mg/cm$^2$-hr; or v) an oligomer product discharge rate from the activation vessel of 0.15 lb/gal/hr, 0.125 lb/gal/hr, 0.1 lb/gal/hr, or 0.075 lb/gal/hr, and an oligomer product discharge rate in the reaction zone can be in a range from 0.75 to 6 lb/gal/hr, 1 to 6 lb/gal/hr, 1.2 to 5.5 lb/gal/hr, 1.4 to 5 lb/gal/hr, 1.5 to 4.5 lb/gal/hr, or 1.6 to 4.25 lb/gal/hr; or vi) a ΔT from the inlet of the activation vessel to the outlet of the activation vessel of 5° C., 4° C., 3° C., 2° C., or 1° C.; or vii) a maximum time of 8 hr, 6 hr, 4 hr, 2 hr, 1 hr, 45 min, 30 min, 20 min, or 15 min. In these first and second processes, an amount of ethylene introduced into the activation vessel can be less than 50%, 40%, 30%, or 20% of an amount of ethylene introduced into the reaction zone; or step b) can be performed at an activation temperature and an activation pressure, and the first mixture in the activation vessel can be below the bubble point at the activation temperature and the activation pressure.

Generally, the features of the first process and the second process (e.g., the catalyst system, the organic reaction medium, the first mixture and its average residence time in the activation vessel, the oligomerization conditions under which the oligomer product is formed, and the reaction zone, among others) are independently described herein, and these features can be combined without limitation, and in any combination, to further describe the first process and the second process. Moreover, additional process steps can be performed before, during, and/or after any of the steps of any of the processes disclosed herein, unless stated otherwise.

Referring first to step a) of the first process, which is directed to forming a first mixture in an activation vessel, the first mixture can comprise ethylene, a catalyst system comprising i) a heteroatomic ligand chromium compound complex and an organoaluminum compound, or ii) a heteroatomic ligand, a chromium compound, and an organoaluminum compound, optionally, a first organic reaction medium, and optionally, hydrogen. Suitable heteroatomic ligand chromium compound complexes, heteroatomic ligands, chromium compounds, and organoaluminum compounds are disclosed herein and can be used without limitation in the first process. While not required, the catalyst system can further comprise a suitable catalyst system organic medium, such as an aromatic hydrocarbon (e.g., benzene, toluene, xylene (including orthoxylene, meta-xylene, para-xylene, or mixtures thereof), cumene, and ethylbenzene, or a $C_8$ and/or $C_9$ aromatic stream (Total Atosol 100, ExxonMobil A100, and Shell Solv100, or other streams containing xylenes, cumene, or ethylbenzene, among others), among other aromatic hydrocarbons).

While also not required, a first organic reaction medium often can be combined with ethylene and the catalyst system to form the first mixture in the activation vessel. When employed, any suitable organic reaction medium can be used as the first organic reaction medium, such as a hydrocarbon. Hydrocarbons can include, for example, aliphatic hydrocarbons, aromatic hydrocarbons, petroleum distillates, or combinations thereof; alternatively, aliphatic hydrocarbons; or alternatively, aromatic hydrocarbons. Aliphatic hydrocarbons which can be used as the first organic reaction medium include $C_3$ to $C_{20}$ aliphatic hydrocarbons; alternatively, $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. In some aspects, the aliphatic hydrocarbon which can be utilized as the first organic reaction medium can be a hydrocarbon olefin (linear or branched, or terminal or internal). Non-limiting examples of suitable acyclic aliphatic hydrocarbon reaction medium that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or a mixture of linear and branched $C_6$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), heptane (n-heptane or a mixture of linear and branched $C_7$ acyclic aliphatic hydrocarbons), octane (n-octane or a mixture of linear and branched $C_8$ acyclic aliphatic hydrocarbons), or combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or a mixture of linear and branched $C_6$ acyclic aliphatic hydrocarbons); alternatively, heptane (n-heptane or a mixture of linear and branched $C_7$ acyclic aliphatic hydrocarbons); or alternatively, octane (n-octane or a mixture of linear and branched $C_8$ acyclic aliphatic hydrocarbons). In other aspects, the acyclic aliphatic reaction medium can be a product of the oligomerization (e.g., 1-hexene and/or 1-octene). Non-limiting examples of suitable cyclic aliphatic hydrocarbon reaction medium include cyclohexane and methyl cyclohexane; alternatively, cyclohexane; or alternatively, methylcyclohexane. Aromatic hydrocarbons which can be useful as an organic reaction medium include $C_6$ to $C_{20}$ aromatic hydrocarbons, or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), cumene, and ethylbenzene, or combinations thereof; alternatively, benzene; alternatively, toluene; alternatively, xylene (including ortho-xylene, meta-xylene, para-xylene or mixtures thereof); alternatively, cumene; or alternatively, ethylbenzene. In a particular aspect of this disclosure, the first organic reaction medium can comprise, or consist essentially of, or consist of, cyclohexane.

Ethylene, the catalyst system components, and the first organic reaction medium can be combined in any order. Thus, the first organic reaction medium can be introduced into the activation vessel with any one of the ethylene, the catalyst system organic medium (if used), the heteroatomic ligand chromium compound complex, and the organoaluminum compound (or the heteroatomic ligand, the chromium compound, and the organoaluminum compound), or in any combination. For instance, in one aspect, a first feed stream comprising ethylene and at least a portion of the first organic reaction medium can be introduced into the activation vessel separate from a catalyst system mixture comprising the catalyst system. The catalyst system mixture also can contain a portion of the first organic reaction medium.

In some aspects, the heteroatomic ligand chromium compound complex and the organoaluminum compound are separately introduced into the activation vessel, or at least one of the heteroatomic ligand, the chromium compound, and the organoaluminum compound is separately introduced into the activation vessel. In an aspect, the heteroatomic ligand and the chromium compound are separately introduced into the activation vessel; this technique is generally referred to as in-situ formation of the heteroatomic ligand chromium compound complex in the activation vessel. In other aspects, a catalyst system mixture comprising the heteroatomic ligand chromium compound complex and the organoaluminum compound (or the heteroatomic ligand, the chromium compound, and the organoaluminum compound), and optionally at least a portion of the first organic reaction medium, can be formed and then introduced into the activation vessel. The catalyst system mixture can further contain a catalyst system organic medium. Catalyst system organic medium are independently described herein and can utilized without limitation to further describe the processes described herein (e.g., ethylbenzene or other suitable aromatic hydrocarbons described herein). Thus, the catalyst system mixture can be formed prior to entering the activation vessel. The catalyst system mixture can be aged for any suitable period of time (e.g., 5 sec to 48 hr, from 10 sec to 36 hr, from 30 sec to 24 hr, from 1 min to 18 hr, from 5 min to 6 hr, from 10 min to 4 hr, or from 20 min to 2 hr) in the substantial absence of ethylene prior to introducing the catalyst system mixture into the activation vessel.

While not required, hydrogen can be combined with ethylene—and the optional first organic reaction medium—to form the first mixture in the activation vessel. Thus, in one aspect of the disclosure, hydrogen is present in step a) of the first process, while in another aspect, hydrogen is not present.

In an aspect, step b) of the first process (or the second process) maintains the first mixture of the first process (or the second process) in the activation vessel for an average residence time. Generally, the average residence time can range from a minimum average residence time to a maximum average residence time. Generally, the minimum average residence time can be 10 sec, 30 sec, 1 min, or 2 min. The maximum average residence time for the average residence time range can be based upon any one or more of several parameters including time, a period of time sufficient to form an amount of a first oligomer product in the activation vessel, a conversion of ethylene in the activation vessel compared to the total ethylene utilized in step a) and step c), a catalyst system productivity in the activation vessel compared to a catalyst system productivity in the reaction zone, a fouling rate in the activation vessel, an oligomer product discharge rate from the activation vessel, or a ΔT from the inlet of the activation vessel to the outlet of the activation vessel. Alternatively or additionally, the activation step b) of the first process (or the second process) can be performed using an amount of ethylene introduced into the activation vessel that is a percentage of the amount of the ethylene introduced into the reaction zone and/or can be performed at an activation temperature and an activation pressure such that the first mixture in the activation vessel can be below the bubble point at the activation temperature and the activation pressure. These features are independently described and can be utilized singly or in any combination to further describe the processes described herein.

The appropriate residence time in the activation vessel can vary depending upon the identity of the heteroatomic ligand chromium compound complex (or heteroatomic ligand and chromium compound), the organoaluminum compound, and/or operating conditions in the activation vessel, but often can be on the order of the induction time for the particular catalyst system under oligomerization reaction conditions. Additionally, the components of the catalyst system can be various energetic states which at any given time or temperature lead the catalyst system having a distribution of molecules in various stages of activation. In an ideal situation, the average residence time would exactly match the induction time, such that the first mixture contains fully activated catalyst, but no oligomerization of ethylene has yet to occur. However, one of ordinary skill in the art would recognize, the average residence time can include catalyst system residence times which are greater than the induction time. Thus, some oligomer product can be formed in the activation vessel and the maximum average residence time may be described using parameters which could include features which indicate that a small amount of ethylene oligomerization is occurring in the activation vessel.

In an aspect, step b) of the first process (or the second process), the first mixture can be maintained in the activation vessel for an average residence time. In one aspect, the minimum average residence time can be 10 sec, 30 sec, 1 min, or 2 min; additionally or alternatively, the maximum average residence time can be 8 hr, 6 hr, 4 hr, 2 hr, 45 min, 30 min, 20 min, or 15 min. Generally, the average residence time can be in a range from any minimum time disclosed herein to any maximum time disclosed herein. Accordingly, suitable non-limiting ranges for the average residence time can include the following: from 10 sec to 45 min, from 10 sec to 30 min, from 30 sec to 30 min, from 30 sec to 20 min, from 1 min to 45 min, from 1 min to 30 min, or from 2 min to 15 min. Other appropriate ranges for the average residence time are readily apparent from this disclosure.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be a period of time sufficient to form an amount of a first oligomer product in the activation vessel equal to 5% (or 4%, or 3%, or 2%, or 1%) of an amount of the oligomer product formed in the reaction zone. Generally, the average residence time can be in a range from any minimum time disclosed herein to any maximum time, defined by the amount of the first oligomer product formed in the activation vessel, disclosed herein. Accordingly, suitable non-limiting ranges for the average residence time can include the following: from 10 sec to 5%, from 10 sec to 1%, from 30 sec to 4%, from 30 sec to 1%, from 1 min to 3%, or from 2 min to 2% (the upper limit of 1-5% is based on the amount of the first oligomer product formed in the activation vessel divided by the amount of the oligomer product formed in the reaction zone). The appropriate maximum average residence time in the activation vessel can vary. Other appropriate ranges for the average residence time are readily apparent from this disclosure. Once the induction time of the catalyst system has been reached, oligomerization of ethylene can commence. Beneficially, no substantial oligomerization occurs in the activation vessel, but generally, a very small amount (typically less than or equal to 5% of the amount of oligomer product formed in the reaction zone, and lesser amounts such as 4%, 3%, 2%, 1%, and so forth) is permissible. The respective amounts of the first oligomer product formed in the activation vessel and the oligomer product formed in the reaction zone can be quantified using a gas chromatography (GC) analytical technique, or other suitable techniques.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be characterized by a conversion of ethylene in the activation vessel that is less than or equal to 5 mol % (or 4 mol %, or 3 mol %, or 2 mol %, or 1 mol %, or 0.5 mol %) of a total ethylene utilized in step a) and step c) of the first and second processes. Generally, the average residence time can be in a range from any minimum time disclosed herein to any maximum time, defined by the conversion of ethylene in the activation vessel, disclosed herein. Accordingly, suitable non-limiting ranges for the average residence time can include the following: from 10 sec to 5 mol %, from 10 sec to 1 mol %, from 30 sec to 4 mol %, from 30 sec to 1 mol %, from 1 min to 3 mol %, or from 2 min to 2 mol % (the upper limit of 0.5-5 mol % is based on the conversion of ethylene in the activation vessel divided by the total ethylene utilized in step a) and step c) of the first process (or the second process)). Thus, it is anticipated that either a very small amount, or effectively none, of the ethylene feed will be converted (e.g., to an oligomer) in the activation vessel. Other appropriate ranges for the average residence time are readily apparent from this disclosure. The amount of ethylene conversion can be quantified using an on-line Raman spectroscopy analytical technique, or other suitable techniques.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be characterized by a catalyst system productivity in the activation vessel that is equal to 5%, 4%, 3%, 2%, or 1% of a catalyst system productivity in the reaction zone (in units of kg of normal alpha olefin produced per gram of chromium per hour, kg NAO/g Cr per hr). Generally, the average residence time can be in a range from any minimum time disclosed herein to any maximum time, defined by the catalyst system productivity in the reaction zone, disclosed herein. Accordingly, suitable non-limiting ranges for the average residence time can include the following: from 10 sec to 5%, from 10 sec to 1%, from 30 sec to 4%, from 30 sec to 1%, from 1 min to 3%, or from 2 min to 2% (the upper limit of 1-5% is based on the catalyst system productivity in the activation vessel divided by the catalyst system productivity in the reaction zone). The appropriate maximum average residence time in the activation vessel can vary. Once the induction time of the catalyst system has been reached, oligomerization of ethylene can commence, and the catalyst system productivity can begin to increase. Other appropriate ranges for the average residence time are readily apparent from this disclosure. In some instances, the productivity in the activation vessel can be equal to zero—no normal alpha olefin has been produced.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be characterized by a fouling rate in the activation vessel of equal to 0.065 mg/cm$^2$-hr, 0.06 mg/cm$^2$-hr, 0.055 mg/cm$^2$-hr, 0.05 mg/cm$^2$-hr, 0.045 mg/cm$^2$-hr, or 0.04 mg/cm$^2$-hr. Generally, the average residence time can be in a range from any minimum time disclosed herein to any maximum time, defined by the fouling rate in the activation vessel, disclosed herein. Accordingly, suitable non-limiting ranges for the average residence time can include the following: from 10 sec to an activation vessel fouling rate of 0.065 mg/cm$^2$-hr, from 10 sec to an activation vessel fouling rate of 0.04 mg/cm$^2$-hr, from 30 sec to an activation vessel fouling rate of 0.055 mg/cm$^2$-hr, from 30 sec to an activation vessel fouling rate of 0.045 mg/cm$^2$-hr, from 1 min to an activation vessel fouling rate of 0.05 mg/cm$^2$-hr, or from 2 min to an activation vessel fouling rate of 0.045 mg/cm$^2$-hr. The appropriate maximum fouling rate in the activation vessel can vary. Once the induction time of the catalyst system has been reached, oligomerization of ethylene can commence. Other appropriate ranges for the average residence time are readily apparent from this disclosure. In circumstances where substantially no oligomerization takes place in the activation vessel—only activation of the catalyst in the presence of ethylene—it is expected that the fouling rate will be negligible.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be characterized by an oligomer product discharge rate from the activation vessel that is equal to 0.15 lb/gal/hr, 0.125 lb/gal/hr, 0.1 lb/gal/hr, or 0.075 lb/gal/hr, whereas the oligomer product discharge rate from the reaction zone often can be in a range from 0.75 to 6 lb/gal/hr, from 1 to 6 lb/gal/hr, 1.2 to 5.5 lb/gal/hr, 1.4 to 5 lb/gal/hr, 1.5 to 4.5 lb/gal/hr, or 1.6 to 4.25 lb/gal/hr. Generally, the average residence time can be in a range from any minimum time disclosed herein to any maximum time, defined by the oligomer product discharge rate from the activation vessel, disclosed herein. Accordingly, suitable non-limiting ranges for the average residence time can include the following: from 10 sec to an activation vessel oligomer product discharge rate equal to 0.15 lb/gal/hr, from 10 sec to an activation vessel oligomer product discharge rate equal to 0.075 lb/gal/hr, from 30 sec to an activation vessel oligomer product discharge rate equal to 0.075 lb/gal/hr, from 1 min to an activation vessel oligomer product discharge rate equal to 0.125 lb/gal/hr, or from 2 min to an activation vessel oligomer product discharge rate equal to 0.1 lb/gal/hr, and where the oligomer product discharge rate from the reaction zone often can be in a range from 0.75 to 6 lb/gal/hr, from 1 to 6 lb/gal/hr, from 1.2 to 5.5 lb/gal/hr, from 1.4 to 5 lb/gal/hr, from 1.5 to 4.5 lb/gal/hr, or from 1.6 to 4.25 lb/gal/hr. Stated another way, the oligomer product discharge rate from the activation vessel can be less than or equal to 7.5% of the oligomer product discharge rate from the reaction zone, such as less than or equal to 5%, less than or equal to 3%, less than or equal to 2%, or less than or equal to 1%. The oligomer product discharge rate from the activation vessel can be effectively zero if no measurable oligomerization occurs in the activation vessel. Other appropriate ranges for the average residence time are readily apparent from this disclosure.

In an aspect, the first mixture in the first process (or the second process) can be maintained in the activation vessel for an average residence time in which the minimum average residence time can be 10 sec, 30 sec, 1 min, or 2 min; alternatively or additionally, the maximum average residence time can be characterized by a $\Delta T$ from the inlet of the activation vessel to the outlet of the activation vessel of equal to 5° C., 4° C., 3° C., 2° C., or 1° C. (due to the exothermic ethylene oligomerization reaction). Generally, the average residence time can be in a range from any minimum time disclosed herein to any maximum time, defined by the heat generated in the activation vessel, disclosed herein. Accordingly, suitable non-limiting ranges for the average residence time can include the following: from 10 sec to a $\Delta T$ from the inlet of the activation vessel to the outlet of the activation vessel of 5° C., from 10 sec to a $\Delta T$ of 2° C., from 30 sec to a $\Delta T$ of 2° C., from 30 sec to a $\Delta T$ of 1° C., from 1 min to a $\Delta T$ of 3° C., or from 2 min to a $\Delta T$ of 3° C. (the $\Delta T$ is measured from the inlet of the activation vessel to the outlet of the activation vessel). The $\Delta T$ is based upon the heat generated in the activation vessel without any external cooling being applied to the activation vessel. Thus, it is anticipated that either a very small amount of heat is generated, or effectively no heat is generated (particularly, if no substantial oligomerization of ethylene occurs), in the activation vessel. Other appropriate ranges for the average residence time are readily apparent from this disclosure.

In an aspect, the first mixture in the first process (or the second process) can have an amount of ethylene introduced into the activation vessel that is less than 50%, less than or equal to 40%, less than or equal to 30%, less than or equal to 25%, less than or equal to 20%, less than or equal to 15%, less than or equal to 10%, or less than or equal to 5% of an amount of ethylene introduced into the reaction zone. Although it is possible to have a majority of the ethylene feed, or even all of the ethylene feed, introduced into the activation vessel, only a minor fraction of ethylene fed to the activation vessel is needed to activate the catalyst system for oligomerization.

In an aspect, step b) of the first process (or the second process) can be performed at an activation temperature and an activation pressure such that the first mixture in the activation vessel can be below the bubble point at the activation temperature and the activation pressure. In an aspect, the activation temperature can be any oligomerization temperature suitable for the formation of the oligomer product in step d) of the first process (or the second process). Often, the oligomer product can be formed at (and/or the activation temperature independently can be) a minimum temperature of 0° C., 20° C., 30° C., 40° C., 45° C., or 50° C.; additionally or alternatively, at a maximum temperature of 165° C., 160° C., 150° C., 140° C., 130° C., 115° C., 100° C., or 90° C. Generally, the oligomerization temperature at which the oligomer product is formed (or the activation temperature independently) can be in a range from any minimum temperature disclosed herein to any maximum temperature disclosed herein. Accordingly, suitable non-limiting ranges for the oligomerization temperature and/or activation temperature independently can include the following: from 0° C. to 165° C., from 20° C. to 160° C., from 20° C. to 115° C., from 40° C. to 160° C., from 40° C. to 140° C., from 50° C. to 150° C., from 50° C. to 140° C., from 50° C. to 130° C., from 50° C. to 100° C., from 60° C. to 115° C., from 70° C. to 100° C., or from 75° C. to 95° C. Other appropriate activation and oligomerization temperatures and temperature ranges are readily apparent from this disclosure.

The activation pressure can be any oligomerization pressure suitable for the formation of the oligomer product in step d) of the first process (or the second process). For example, the oligomer product can be formed at (or the activation pressure, or activation ethylene partial pressure, independently can be) a minimum pressure (or ethylene partial pressure) of 50 psig (344 kPa), 100 psig (689 kPa), 200 psig (1.4 MPa), or 250 psig (1.5 MPa); additionally or alternatively, at a maximum pressure (or ethylene partial pressure) of 4,000 psig (27.6 MPa), 3,000 psig (20.9 MPa), 2,000 psig (13.8 MPa), or 1,500 psig (10.3 MPa). Generally, the oligomerization pressure (or ethylene partial pressure) at which the oligomer product is formed (or the activation pressure, or activation ethylene partial pressure, independently) can be in a range from any minimum pressure disclosed herein to any maximum pressure disclosed herein. Accordingly, suitable non-limiting oligomerization pressures (or ethylene partial pressures) and/or activation pressures (or activation ethylene partial pressures) ranges independently can include the following: from 50 psig (344 kPa) to 4.000 psig (27.6 MPa), from 100 psig (689 kPa) to 3,000 psig (20.9 MPa), from 100 psig (689 kPa) to 2.000 psig (13.8 MPa), from 200 psig (1.4 MPa) to 2,000 psig (13.8 MPa), from 200 psig (1.4 MPa) to 1,500 psig (10.3 MPa), or from 250 psig (1.5 MPa) to 1,500 psig (10.3 MPa). Other appropriate oligomerization pressures (or ethylene partial pressures) and/or activation pressures (or activation ethylene partial pressures) are readily apparent from this disclosure.

Referring now to step c) of the first process (or the second process), ethylene, the first mixture from step b) of the first process (or the second process), a second organic reaction medium, and optionally hydrogen can be introduced into a reaction zone. Thus, in one aspect of the disclosure, hydrogen is present in step c) of the first process (or the second process), while in another aspect, hydrogen is not present. When used, hydrogen can be fed directly to the reaction zone, however, in an aspect, hydrogen can be combined with the ethylene and or second organic reaction medium feed prior to introduction into the reaction zone. In the reaction zone, the hydrogen partial pressure can be at least 1 psig (6.9 kPa), 5 psig (34 kPa), 10 psig (69 kPa), 25 psig (172 kPa), or 50 psig (345 kPa); additionally or alternatively, a maximum hydrogen partial pressure of 2000 psig (13.8 MPa), 1750 psig (12.1 MPa), 1500 psig (10.3 MPa), 1250 psig (8.6 MPa), 1000 psig (6.9 MPa), 750 psig (5.2 MPa), 500 psig (3.4 MPa), or 400 psig (2.8 MPa). Generally, the hydrogen partial pressure can range from any minimum hydrogen partial pressure disclosed herein to any maximum hydrogen partial pressure disclosed herein. Therefore, suitable non-limiting ranges for the hydrogen partial pressure can include the following ranges: from 1 psig (6.9 kPa) to 2000 psig (13.8 MPa), from 1 psig (6.9 kPa) to 1750 psig (12.1 MPa), from 5 psig (34 kPa) to 1500 psig (10.3 MPa), from 5 psig (34 kPa) to 1250 psig (8.6 MPa), from 10 psig (69 kPa) to 1000 psig (6.9 MPa), from 10 psig (69 kPa) to 750 psig (5.2 MPa), from 10 psig (69 kPa) to 500 psig (3.5 MPa), from 25 psig (172 kPa) to 750 psig (5.2 MPa), from 25 psig (172 kPa) to 500 psig (3.4 MPa), from 25 psig (172 kPa) to 400 psig (2.8 MPa), or from 50 psig (345 kPa) to 500 psig (3.4 MPa). Other appropriate hydrogen partial pressures in the reaction zone for the formation of the oligomer product are readily apparent from this disclosure. In some non-limiting aspects, the activation vessel can include hydrogen and the activation vessel can independently have any hydrogen partial pressure utilized for the reaction zone described herein.

The second organic reaction medium can be any of the hydrocarbons discussed herein for the first organic reaction medium described herein (e.g., cyclohexane). In some aspects, the second organic reaction medium and the first organic reaction medium are the same hydrocarbon (or mixture of hydrocarbons), although this is not a requirement.

Ethylene, the first mixture from step b) (which contains "activated" catalyst system or catalyst system which has had its induction period reduced), the second organic reaction medium, and hydrogen (when used) can be combined in any order. For instance, the ethylene and the first mixture from step b) can be introduced separately into the reaction zone in step c). In a particular non-limiting aspect of step c), a second feed stream is formed that comprises ethylene, at least a portion (and in some cases, all) of the second organic reaction medium, and hydrogen (when used), and this second feed stream is introduced into the reaction zone separately from the first mixture from step b) (which contains the catalyst system).

In step d) of the first process (or the second process), an oligomer product is formed in the reaction zone. Suitable temperatures, ethylene partial pressures, and hydrogen partial pressures are independently discussed herein. These independently described features can utilized without limitation and in any combination to further the conditions of the reaction zone and/or the conditions at which the oligomerization product is formed. The reaction zone in which the oligomer product is formed can comprise any suitable reactor. Non-limiting examples of reactor types can include a stirred tank reactor, a plug flow reactor, or any combination thereof; alternatively, a fixed bed reactor, a continuous stirred tank reactor, a loop slurry reactor, a solution reactor, a tubular reactor, a recycle reactor, or any combination thereof. In an aspect, the reaction zone can have more than one reactor in series or in parallel, and including any combination of reactor types and arrangements. Moreover, the oligomerization process used to form the oligomer product can be a continuous process or a batch process, or any reactor or vessel within the oligomerization reaction system can be operated continuously or batchwise.

In accordance with the first process (or second process) of this disclosure, the productivity of the catalyst system under oligomerization conditions generally can be greater than 50 kg, greater than 100 kg, greater than 250 kg, greater than 500 kg, greater than 750 kg, greater than 1000 kg, greater than 1250 kg, greater than 1500 kg, or greater than 2000 kg, of normal alpha olefins per gram of chromium per hour. For the purpose of determining the productivity, the conditions under the oligomer product is formed can include MAO, using cyclohexane as the reaction medium and 50 psig hydrogen pressure, and with an oligomerization temperature of 90° C. and an ethylene pressure of 875 psig.

The first process (or the second process) can include a step of discharging (from the reaction zone) a reaction zone effluent stream comprising the oligomer product. The reaction zone effluent stream can further comprise, in some aspects, the catalyst system, ethylene, and organic reaction medium. The catalyst system can be deactivated by contacting the reaction zone effluent stream with a suitable catalyst system deactivating agent, or subjecting the oligomer product to suitable process steps to deactivate the catalyst system, or a combination of both. The reaction zone effluent stream wherein the catalyst system has been deactivated can be referred to as a deactivated reaction zone effluent stream. The catalyst system deactivating agent can comprise (or consist essentially of, or consist of) water, an alcohol compound, an amine compound, or any combination thereof; alternatively, water; alternatively, an alcohol compound; or alternatively, an amine compound. In an aspect, the alcohol compound can be a monoalcohol compound, a diol compound, a polyol compound, or any combination thereof. In some aspects, the alcohol compound can comprise, consist essentially of, or consist of, a $C_1$ to $C_{20}$ mono alcohol. In some aspects, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In some aspects, the alcohol compound can comprise, consist essentially of, or consist of, methanol, ethanol, 1-propanol, 2-propanol, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-dodecanol, a 2-dodecanol, 2-ethyl-1-decanol, or mixtures thereof.

Additionally or alternatively, the catalyst system can be deactivated by contact with an aqueous base solution or aqueous acid solution (e.g., an aqueous Group 1 metal hydroxide solution or an aqueous mineral acid solution). Such deactivation processes to deactivate the catalyst system can also potentially remove a portion, or substantially all, of the metal catalyst system components from the oligomer product.

The first process (or the second process) can further comprise a step of isolating a liquid oligomer product, e.g., from the reaction zone effluent stream, from the deactivated reaction zone effluent stream, from solid polymer product, from the organic reaction medium, etc., using any suitable technique. Various suitable separation techniques can be employed, as would be recognized by those of skill in the art. In an aspect, and not limited thereto, a filtration process, an evaporation process, or a distillation process can be used, as well as combinations of more than one separation technique. The liquid oligomer product can contain $C_6$ olefins; alternatively, $C_8$ olefins; or alternatively, $C_6$ and $C_8$ olefins. Based on the weight of the liquid oligomer product, the amount of $C_6$ and/or $C_8$ olefins ($C_6$ olefins, $C_8$ olefins, or total $C_6+C_8$ olefins) typically can fall within a range from 70 to 99.9 wt. %, from 75 to 99.8 wt. %, or from 80 to 99.6 wt. %.

Selectivity to α-olefins in the liquid oligomer product can be unexpectedly high. In an aspect, the $C_6$ olefins, of a liquid oligomer product comprising at least 10 wt. % $C_6$ olefins, can contain 1-hexene in an amount ranging from 80 to 99.99 mol %, from 82 to 99.99 mol %, from 85 to 99.99 mol %, from 90 to 99.99 mol %, or from 95 to 99.9 mol %. Likewise, in an aspect, the $C_8$ olefins, of a liquid oligomer product comprising at least 10 wt. % $C_8$ olefins, can contain 1-octene in an amount ranging from 80 to 99.99 mol %, from 85 to 99.99 mol %, from 90 to 99.99 mol %, from 95 to 99.9 mol %, or from 97 to 99.99 mol %.

Referring now to the second process disclosed herein, which can comprise a) forming a first mixture in an activation vessel, the first mixture comprising 1) a first catalyst system comprising i) a first heteroatomic ligand chromium compound complex and a first organoaluminum compound, or ii) a first heteroatomic ligand, a first chromium compound, and a first organoaluminum compound, 2) a first feed comprising ethylene, a second catalyst system comprising i) a second heteroatomic ligand chromium compound complex and a second organoaluminum compound, or ii) a second heteroatomic ligand, a second chromium compound, and a second organoaluminum compound, a second organic reaction medium, a second oligomer product, and optionally hydrogen, 3) optionally, a first organic reaction medium, and 4) optionally, hydrogen; b) maintaining the first mixture in the activation vessel for an average residence time; c) introducing into a reaction zone: ethylene, the first mixture from step b), the second organic reaction medium, and optionally, hydrogen; and d) forming an oligomer product in the reaction zone. In the second process, a portion of a reaction zone effluent is fed to the activation vessel as the first feed. All of the features and characteristics disclosed herein for the first process are likewise applicable to the second process disclosed herein. As such, the average residence time (as a range from a minimum time to a maximum time defined by one or more of time, ethylene conversion in the activation vessel, catalyst system productivity in the activation vessel and the reaction zone, fouling rate, oligomer product discharge rate from the activation vessel, and ΔT from the inlet of the activation vessel to the outlet of the activation vessel), the percentage of overall ethylene fed to the activation vessel, the bubble point, the catalyst system organic medium, the pressure and temperature conditions in the activation vessel and reaction zone, the use of hydrogen, the downstream separations, the liquid oligomer product described herein (among other process features described herein) can be utilized without limitation and in any combination to further describe the second process.

In step a) of the second process, a first mixture is formed in the activation vessel and the first mixture comprises 1) a first catalyst system comprising i) a first heteroatomic ligand chromium compound complex and a first organoaluminum compound, or ii) a first heteroatomic ligand, a first chromium compound, and a first organoaluminum compound, 2) a first feed comprising ethylene, a second catalyst system comprising i) a second heteroatomic ligand chromium compound complex and a second organoaluminum compound, or ii) a second heteroatomic ligand, a second chromium compound, and a second organoaluminum compound, a second organic reaction medium, a second oligomer product, and optionally hydrogen, 3) optionally, a first organic reaction medium, and 4) optionally, hydrogen. Suitable heteroatomic ligand chromium compound complexes, heteroatomic ligands, chromium compounds, and organoaluminum compounds are disclosed herein and can be used without limitation in the second process. The first and the second heteroatomic ligand chromium compound complexes, heteroatomic ligands, chromium compounds, and organoaluminum compounds can be the same or different. Generally, however, the first and the second catalyst systems can contain the same components.

While not required, a first organic reaction medium often can be combined with the first catalyst system and the first feed to form the first mixture in the activation vessel. Likewise, while not required, hydrogen also can be fed to the activation vessel and combined with the first catalyst system and the first feed—and the optional first organic reaction medium—to form the first mixture in the activation vessel. The first feed is a portion of a reaction zone effluent stream from the reaction zone, and is often referred to as a slip stream from the reaction zone. Since the first feed comes from the reaction zone, it contains ethylene, the second catalyst system, the second organic reaction medium, a second oligomer product, and optionally hydrogen. Nominally, the first feed can contain 50-75 wt. % of the second organic reaction medium, 10-30 wt. % of the second oligomer product (e.g., hexenes and/or octenes), and 5-15 wt. % of ethylene. While the first feed contains ethylene, this does not preclude a further ethylene feed to the activation vessel.

The first catalyst system components, the first feed comprising ethylene (and other components), and the first organic reaction medium can be combined in any order. For instance, a first feed stream comprising ethylene and at least a portion of the first organic reaction medium can be introduced into the activation vessel separate from the first catalyst system or one or more components of first catalyst system. In another example, the first catalyst system mixture stream can include the first catalyst system and the first organic reaction medium (and optionally, a suitable catalyst system organic medium).

In some aspects, the first heteroatomic ligand chromium compound complex and the first organoaluminum compound can be separately introduced into the activation vessel, or at least one of the first heteroatomic ligand, the first chromium compound, and the first organoaluminum compound can be separately introduced into the activation vessel. In an aspect, the heteroatomic ligand and the chromium compound are separately introduced into the activation vessel; this technique is generally referred to as in-situ formation of the heteroatomic ligand chromium compound complex in the activation vessel. The first organic reaction medium can be mixed with any single catalyst system component, or any combination of catalyst system components, prior to the activation vessel. In other aspects, a catalyst system mixture comprising the first heteroatomic ligand chromium compound complex and the first organoaluminum compound (or the first heteroatomic ligand, the first chromium compound, and the first organoaluminum compound), and optionally at least a portion of the first organic reaction medium, can be formed and then introduced into the activation vessel. The catalyst system mixture can further contain a catalyst system organic medium, such as an aromatic hydrocarbon (e.g., benzene, toluene, xylene (including ortho-xylene, meta-xylene, para-xylene, or mixtures thereof), cumene, and ethylbenzene, or a $C_8$ and/or $C_9$ aromatic stream (Total Atosol 100, ExxonMobil A100, and Shell Solv100, or other streams containing xylenes, cumene, or ethylbenzene, among others), among other aromatic hydrocarbons). Thus, the catalyst system mixture can be formed prior to entering the activation vessel. The catalyst system mixture can be aged for any suitable period of time (e.g., 5 sec to 48 hr, from 10 sec to 36 hr, from 30 sec to 24 hr, from 1 min to 18 hr, from 5 min to 6 hr, from 10 min to 4 hr, or from 20 min to 2 hr) in the substantial absence of ethylene prior to introducing the catalyst system mixture into the activation vessel.

In step b) of the second process, the first mixture can be maintained in the activation vessel for an average residence time as discussed herein for step b). In step c) of the second process, ethylene, the first mixture from step b), the second organic reaction medium, and optionally hydrogen can be introduced into a reaction zone, as discussed herein for step c). The ethylene introduced into the reaction zone in step c) often is substantially devoid of any catalyst system or any catalyst system components. In step d) of the second process, an oligomer product is formed in the reaction zone, as discussed herein for step d). Similar to the first process, the second process also can include steps of discharging a reaction zone effluent stream comprising the oligomer product from the reaction zone, deactivating the catalyst system, isolating a liquid oligomer product, and recovering $C_6$ and/or $C_8$ olefins (e.g., $C_6$ and/or $C_8$ α-olefins).

Oligomerization Reaction Systems A reaction system consistent with aspects of the present disclosure can comprise (a) an activation vessel configured to form a first mixture, wherein the activation vessel is further configured for an average residence time of the first mixture in the activation vessel, (b) one or more activation vessel inlets configured to introduce i) ethylene and a catalyst system mixture, or ii) ethylene and components of a catalyst system mixture, into the activation vessel, (c) an activation vessel outlet configured to withdraw the first mixture from the activation vessel, (d) a reaction zone configured to contact ethylene, the first mixture, a second organic reaction medium, and optionally hydrogen to form an oligomer product, (e) one or more reaction zone inlets configured to introduce ethylene, the second organic reaction medium, and the first mixture from the activation vessel outlet into the reaction zone, and (f) a reaction zone outlet configured to withdraw a reaction zone effluent stream containing the oligomer product from the reaction zone.

In the reaction system, the average residence time of the first mixture in the activation vessel can be in a range from 10 sec, 30 sec, 1 min, or 2 min up to a period of time i) sufficient to form an amount of a first oligomer product in the activation vessel equal to 5% (or 4%, or 3%, or 2%, or 1%) of an amount of the oligomer product formed in the reaction zone; or ii) for a conversion of ethylene in the activation vessel of 5 mol % (or 4 mol %, or 3 mol %, or 2 mol %, 1 mol %, or 0.5 mol %) of a total ethylene utilized in step a) and step c); or iii) for a catalyst system productivity in the activation vessel of 5%, 4%, 3%, 2%, or 1% of a catalyst system mixture productivity in the reaction zone (in units of kg of normal alpha olefin produced per gram of chromium per hour, kg NAO/g Cr per hr); or iv) for a fouling rate in the activation vessel of 0.065 mg/cm$^2$-hr, 0.06 mg/cm$^2$-hr, 0.055 mg/cm$^2$-hr, 0.05 mg/cm$^2$-hr, 0.045 mg/cm$^2$-hr, or 0.04 mg/cm$^2$-hr; or v) for an oligomer product discharge rate from the activation vessel of 0.15 lb/gal/hr, 0.125 lb/gal/hr, 0.1 lb/gal/hr, or 0.075 lb/gal/hr, and an oligomer product discharge rate of the reaction zone can be in a range from 0.75 to 6 lb/gal/hr, from 1 to 6 lb/gal/hr, from 1.2 to 5.5 lb/gal/hr, from 1.4 to 5 lb/gal/hr, from 1.5 to 4.5 lb/gal/hr, or from 1.6 to 4.25 lb/gal/hr; or vi) for a ΔT from the inlet of the activation vessel to the outlet of the activation vessel of 5° C., 4° C., 3° C., 2° C., or 1° C.; or vii) of 8 hr, 6, hr, 4 hr, 2 hr, 1 hr, 45 min, 30 min, 20 min, or 15 min. In the reaction system, an amount of ethylene introduced into the activation vessel can be less than 50%, 40%, 30%, or 20% of an amount of ethylene introduced into the reaction zone; or the activation vessel can be operated at an activation temperature and an activation pressure, and the first mixture in the activation vessel can be below the bubble point at the activation temperature and the activation pressure. All of the features and characteristics disclosed herein for the first and second processes (e.g., average residence time, ethylene conversion in the activation vessel, catalyst system productivity in the activation vessel and the reaction zone, fouling rate, oligomer product discharge rate from the activation vessel and the reaction zone, heat generation in the activation vessel, percentage of overall ethylene fed to the activation vessel, bubble point, catalyst system organic medium, pressure and temperature conditions in the activation vessel and reaction zone, use of hydrogen, downstream separations, and so forth) are likewise applicable to the oligomerization reaction system disclosed herein.

The (a) activation vessel is configured to form the first mixture, and can be further configured for an average residence time of the first mixture in the activation vessel. The activation vessel can comprise any suitable reactor. Non-limiting examples of reactor types can include a stirred tank reactor (e.g., a CSTR), a plug flow reactor, or any combination thereof; alternatively, a fixed bed reactor, a continuous stirred tank reactor, a loop slurry reactor, a solution reactor, a tubular reactor, a recycle reactor, or any combination thereof. Moreover, the activation vessel can be configured to operate continuously or batchwise.

The (b) one or more activation vessel inlets are configured to introduce i) ethylene and a catalyst system mixture, or ii) ethylene and components of a catalyst system mixture, into the activation vessel. Optionally, at least one of the one or more activation vessel inlets can be further configured to introduce a first organic reaction medium and/or hydrogen into the activation vessel. For instance, some or all of the first organic reaction medium can be introduced into the activation vessel along with the catalyst system mixture or the catalyst system mixture components, along with the ethylene, or introduced separately from the catalyst system mixture, catalyst system mixture components, and ethylene. If used, hydrogen can be introduced into the activation vessel with the ethylene feed, the organic reaction medium, or separately from the catalyst system mixture, catalyst system mixture components, ethylene, and organic reaction medium.

In an aspect, the one or more activation vessel inlets can be configured to introduce the catalyst system mixture into the activation vessel, wherein the catalyst system mixture comprises (i) a first heteroatomic ligand chromium compound complex and a first organoaluminum compound, or (ii) a first heteroatomic ligand, a first chromium compound, and a first organoaluminum compound. The catalyst system mixture can further contain a catalyst system organic medium, such as an aromatic hydrocarbon (e.g., ethylbenzene, xylene (any specific or combination thereof), cumene, or a $C_8$ and/or $C_9$ aromatic stream (e.g., Total Atosol 100, ExxonMobil A100, and Shell Solv100, or other streams containing xylenes, cumene, or ethylbenzene, among others), among other aromatic hydrocarbons). In another aspect, the one or more activation vessel inlets can be configured to introduce the components of the catalyst system mixture into the activation vessel, wherein the components comprise (i) a first heteroatomic ligand chromium compound complex and a first organoaluminum compound (and optional catalyst system organic medium), or (ii) a first heteroatomic ligand, a first chromium compound, and a first organoaluminum compound (and optional catalyst system organic medium).

The (c) activation vessel outlet can be configured to withdraw the first mixture from the activation vessel, and (e) one or more reaction zone inlets can be configured to introduce ethylene, the second organic reaction medium, and the first mixture from the activation vessel outlet into the reaction zone. Therefore, the activation vessel outlet and at least one of the one or more reaction zone inlets can be fluidly connected. Further, the one or more reaction zone inlets can be further configured to introduce hydrogen into the reaction zone, and hydrogen can be fed directly into the reaction zone or combined with ethylene, the organic reaction medium, (or with ethylene and the second organic reaction medium) prior to entering the reaction zone.

The (f) reaction zone outlet can be configured to withdraw a reaction zone effluent stream containing the oligomer product from the reaction zone. Often, the reaction zone effluent stream can further comprise ethylene, the second organic reaction medium, or the catalyst system mixture, or any combination thereof.

If desired, the reaction system can further comprise (g) a controller configured to control the average residence time of the first mixture in the activation vessel, and/or an activation temperature in the activation vessel, and/or an activation pressure in the activation vessel, and/or an ethylene conversion in the activation vessel, and/or an ethylene flow rate into the activation vessel. The controller, which can comprise any suitable processing unit or computer system, can be used to analyze the data regarding the reaction system (e.g., the reaction zone and the activation vessel), and adjust the various process parameters based on the prevailing conditions in the overall reaction system. As an example, if fouling and/or ethylene conversion of greater than 1-5% is found in the activation vessel (or any other feature providing an upper limit to the average residence time described herein), the average residence time of the first mixture in the activation vessel can be decreased to decrease the fouling and/or ethylene conversion (or any other feature providing an upper limit to the average residence time described herein) that occurs within the activation vessel.

Referring now to FIG. 1, which illustrates an oligomerization reaction system 100 consistent with an aspect of the present disclosure. The system 100 can include a catalyst preparation vessel 120, an activation vessel 140, a reaction zone 160, and a separations system 180. In FIG. 1, a heteroatomic ligand chromium compound complex feed stream or heteroatomic ligand and chromium compound feed stream (either separately of combined) 102, an organoaluminum feed stream 104, and a first organic reaction medium feed stream 108 enter the catalyst preparation vessel 120. After a suitable period of aging (if needed), a catalyst system mixture stream 105 exits the catalyst preparation vessel, and then enters the activation vessel 140. In some aspects, all or part of the first organic reaction medium feed stream 108 can be fed directly to activation vessel 140. While not specifically shown in FIG. 1, a catalyst system organic medium (e.g., a suitable aromatic hydrocarbon) can be present in the heteroatomic ligand chromium compound complex feed stream or the heteroatomic ligand and chromium compound feed stream (either one or both) 102, and/or the organoaluminum feed stream 104, and/or can be fed as a separate feed stream to the catalyst preparation vessel 120. In an aspect, the catalyst system organic medium can be combined with the heteroatomic ligand chromium compound complex feed stream or the heteroatomic ligand and chromium compound feed stream (either one or both) 102 and/or the organoaluminum feed stream 104, and the resulting mixture then contacted with the first organic reaction medium feed stream 108. It is understood that there are many different methods in which the catalyst system mixture stream 105 can be prepared, and this disclosure is not limited only to those options described in reference to FIG. 1 or otherwise disclosed herein.

An ethylene feed stream 130 in FIG. 1 can be split into two streams, one of which is an activation vessel ethylene feed stream 125, which is combined with the catalyst system mixture stream 105 in the activation vessel 140. As described herein, the catalyst system is first contacted with ethylene in the activation vessel 140 (and prior to the reaction zone 160) for a particular residence time to activate the catalyst, such that some or all of the induction period in the oligomerization reaction zone can be eliminated.

In FIG. 1, the second stream split from the ethylene feed stream 130 is mixed with an optional hydrogen feed stream 115 and a second reaction medium feed stream 155, thereby forming a combined feed stream 135 to reaction zone 160, which is contacted with a first mixture stream 145 exiting the activation vessel 140. Alternatively, and not shown in FIG. 1, all or part of the optional hydrogen feed stream 115 (and/or all or part of the second reaction medium feed stream 155) can be fed directly to reaction zone 160. Ethylene oligomerization occurs in the reaction zone 160, and exiting the reaction zone 160 is a reaction zone effluent stream 175, which enters a separations system 180 for isolation of desired oligomers products, such as 1-hexene and 1-octene. The separations system 180 also can be configured for catalyst system deactivation and/or removal.

Figure 2:
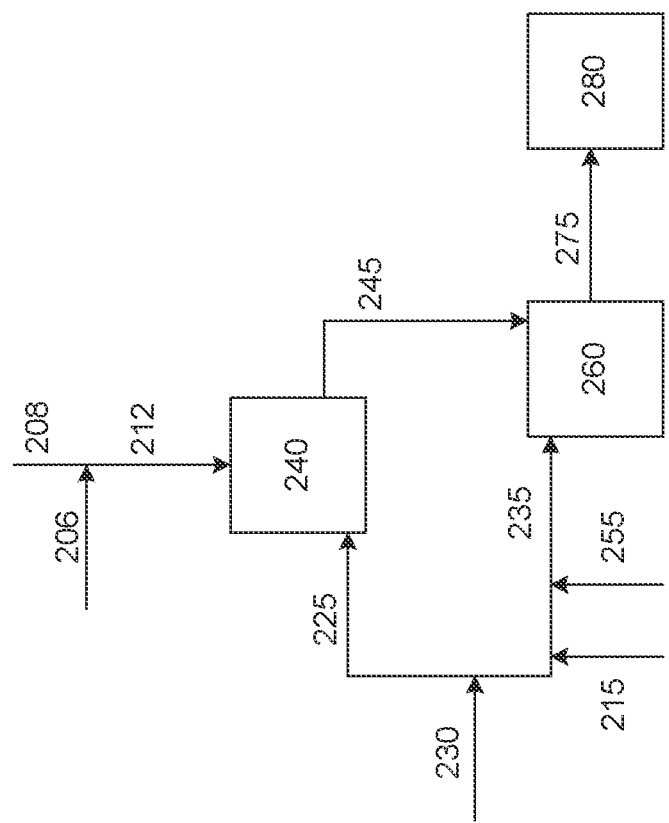
FIG. 2 illustrates an oligomerization reaction system consistent with another aspect of the present disclosure.

Referring now to FIG. 2, which illustrates another oligomerization reaction system 200 consistent with an aspect of the present disclosure. The system 200 can include an activation vessel 240, a reaction zone 260, a separations system 280, an ethylene feed stream 230, an activation vessel ethylene feed stream 225, an optional hydrogen feed stream 215, a second reaction medium feed stream 255, a combined feed stream 235 to the reaction zone 260, and a reaction zone effluent stream 275, which are generally the same as described for the similarly numbered components in FIG. 1.

In FIG. 2, a catalyst preparation vessel is not present, so a first reaction medium feed stream 208 is combined with a catalyst system stream 206 to form a catalyst system mixture stream 212. The catalyst system mixture stream 212 is combined with activation vessel ethylene feed stream 225 in the activation vessel 240 to form a first mixture stream 245, which exits the activation vessel 240 and is fed to the reaction zone 260. Alternatively, and not shown in FIG. 2, the catalyst system mixture (comprising the heteroatomic ligand chromium compound complex, organoaluminum compound, and optionally catalyst system organic medium) or the catalyst system mixture components (the heteroatomic ligand, the chromium compound, the organoaluminum compound, and optionally catalyst system organic medium) can be feed directly (either as a combined stream or as one or more separate feeds) to the activation vessel 240 to form the first mixture stream 245.

Figure 3:
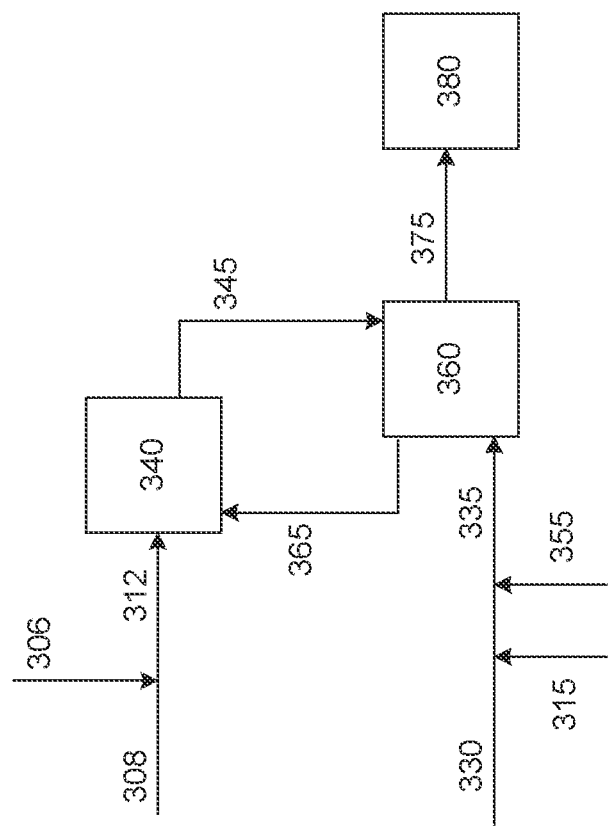
FIG. 3 illustrates an oligomerization reaction system consistent with yet another aspect of the present disclosure.

Referring now to FIG. 3, which illustrates yet another oligomerization reaction system 300 consistent with an aspect of the present disclosure. The system 300 can include an activation vessel 340, a reaction zone 360, a separations system 380, an optional hydrogen feed stream 315, a second reaction medium feed stream 355, a combined feed stream 335 to the reaction zone 360, and a reaction zone effluent stream 375, which are generally the same as described for the similarly numbered components in FIG. 1 and FIG. 2. Likewise, the system 300 can include a first reaction medium feed stream 308, a catalyst system stream 306, and a catalyst system mixture stream 312, which are generally the same as described for the similarly numbered components in FIG. 2. Alternatively, FIG. 3 can employ the catalyst preparation vessel and related streams shown in FIG. 1 (e.g., 102, 104, 108, and 120, with stream 105 entering the activation vessel 140).

In FIG. 3, ethylene feed stream 330 is not split and there is no direct feed of only ethylene into the activation vessel 340. Instead, a first feed 365 from the reaction zone 360 (e.g., it can be a portion of the reaction zone effluent stream 375) enters the activation vessel 340. The first feed 365 contains ethylene (and for example, catalyst, reaction medium, oligomer product, and optionally hydrogen), and is combined with the catalyst system mixture stream 312 in the activation vessel 340 to form a first mixture stream 345, which exits the activation vessel 340 and is fed to the reaction zone 360.

Examples

The disclosure is further illustrated by the following examples, which are not to be construed in any way as imposing limitations to the scope of this disclosure. Various other aspects, modifications, and equivalents thereof which, after reading the description herein, may suggest themselves to one of ordinary skill in the art without departing from the spirit of the present disclosure or the scope of the appended claims.

All manipulations were carried out using a nitrogen filled drybox and standard Schlenk techniques using oven dried glassware (>1 h at 110° C. under vacuum, −30 mm Hg). Cyclohexane diluent was obtained from Sigma-Aldrich in anhydrous grade and degassed prior to use with $N_2$. MMAO-3A/20 was obtained from AkzoNobel/Nouryon and stored in an $N_2$ filled drybox. Methylcyclohexane was obtained from Sigma-Aldrich, degassed under $N_2$, and stored over molecular sieves in the drybox. Ethylbenzene, m-xylene, or xylenes was obtained from Sigma-Aldrich, degassed under $N_2$, and stored over activated 13X molecular sieves in the drybox.

Standard Batch Reactor Procedure

The catalyst system mixture was prepared by dissolving a $N^2$-phosphinyl guanidine chromium(III) trichloride tetrahydrofuran complex having Structure GuCr4 (5.3 µmoles) in 1 g of ethylbenzene and adding MMAO-3A or MMAO-20 to provide the desired Al:Cr ratio. The catalyst system mixture was stirred for 1-5 hr at 50° C. in a vial containing a magnetic stir bar under a nitrogen atmosphere. The contents of the vial were then introduced into 200 mL of dry, degassed cyclohexane. The catalyst mixture in cyclohexane was charged to an evacuated reactor (500 mL stainless steel ZipperClave) held at 60° C. under vacuum. The reactor was then charged with 50 psig $H_2$ and 875 psig ethylene. The reactor temperature was increased to 90° C. and ethylene fed on demand to maintain a pressure of 875 psig. The reactor was maintained at 90° C. using internal cooling coils using tower water and an external water bath if necessary. Once 90° C. was reached, the reaction was allowed to continue for 20-30 min after which reactor was cooled to 35° C. The ethylene was then vented, and the product collected and filtered. Polymer, if observed, was dried and weighed. A sample of the liquid reactor contents was then analyzed by GC on an Agilent 7890-LTM equipped with an Agilent DB-5msUI column (Agilent P/N 222-5532UIL™) with a 30 m length, 0.25 ID, and 0.25 µm film thickness and a flame ionization detector. Table 3 summarizes the catalyst systems, oligomerization conditions, oligomer product properties, and catalyst productivities for Examples 1-4.

Figure 4:
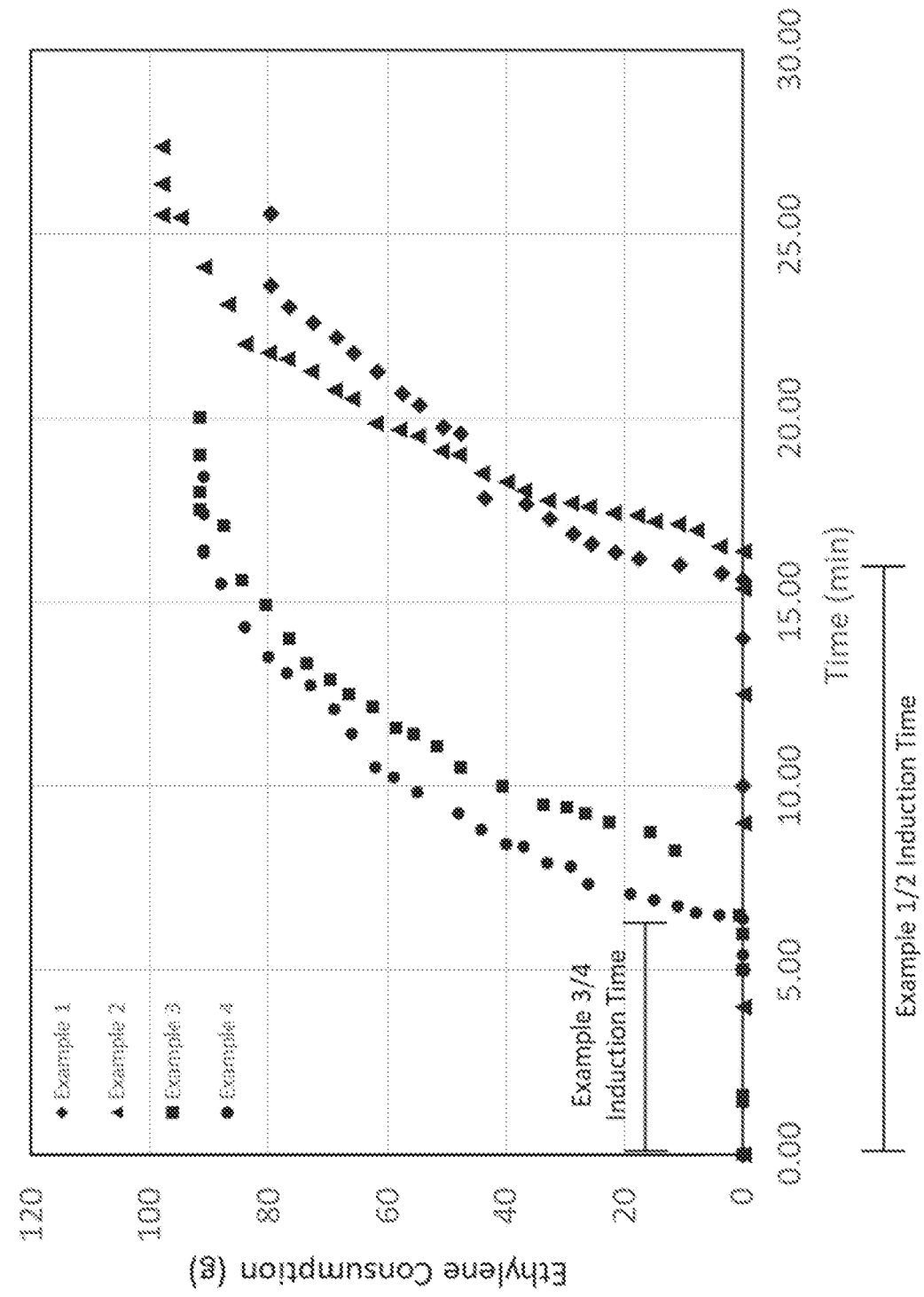
FIG. 4 is a plot of the induction times of the catalyst systems of Examples 1-4.

FIG. 4 shows the ethylene demand for Examples 1-4 and demonstrates that the catalyst induction period was approximately 6.5 min when MMAO-20 was used and approximately 16.5 min when MMAO-3A was used. After pressure equilibration at the desired 875 psig pressure, the reactor ethylene demand was low until the catalyst system was "fully" activated and initiated the ethylene oligomerization reaction at the respective times (6.5 min or 16.5 min) as shown by the rapid increase in ethylene consumption. Without being limited by theory, the ethylene oligomerization reaction appears to be initiated by the presence of high pressure ethylene. Experiments in batch reactors with low pressure ethylene (15 psig) did not prove viable and led to catalyst decomposition, poor reactor performance, or both.

Thus, the catalyst systems of Examples 1-4 could benefit significantly from exposure in an activation vessel to ethylene, as described herein, for a suitable residence time (e.g., up to approximately 6.5 min or 16.5 min, respectively), such that the catalyst system would be fully activated for ethylene oligomerization when it enters the reactor (no induction time needed).

Figure 5:
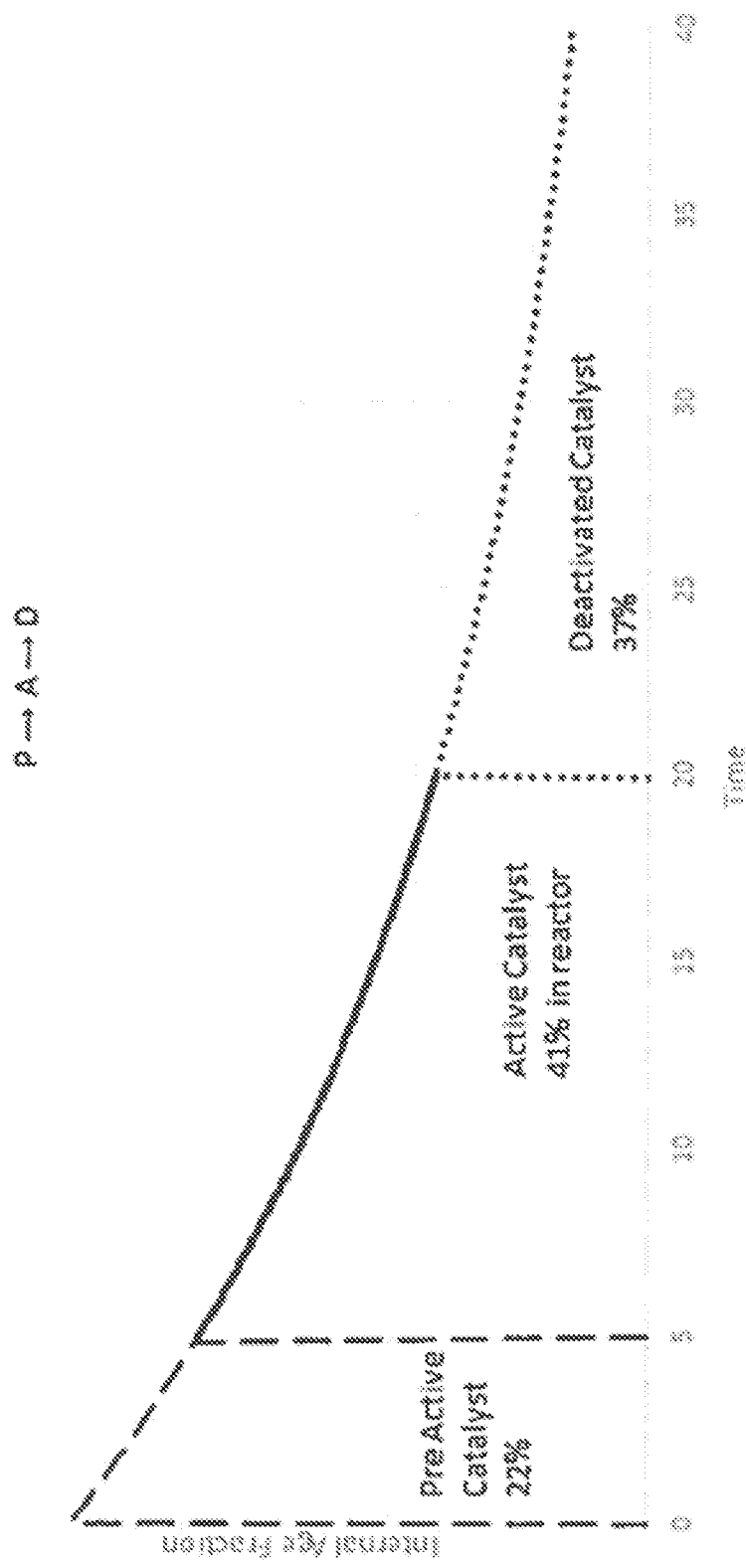
FIG. 5 is a plot illustrating the amount of active catalyst of constructive Example 5 in an ethylene oligomerization reactor without the use of an activation vessel.
Figure 6:
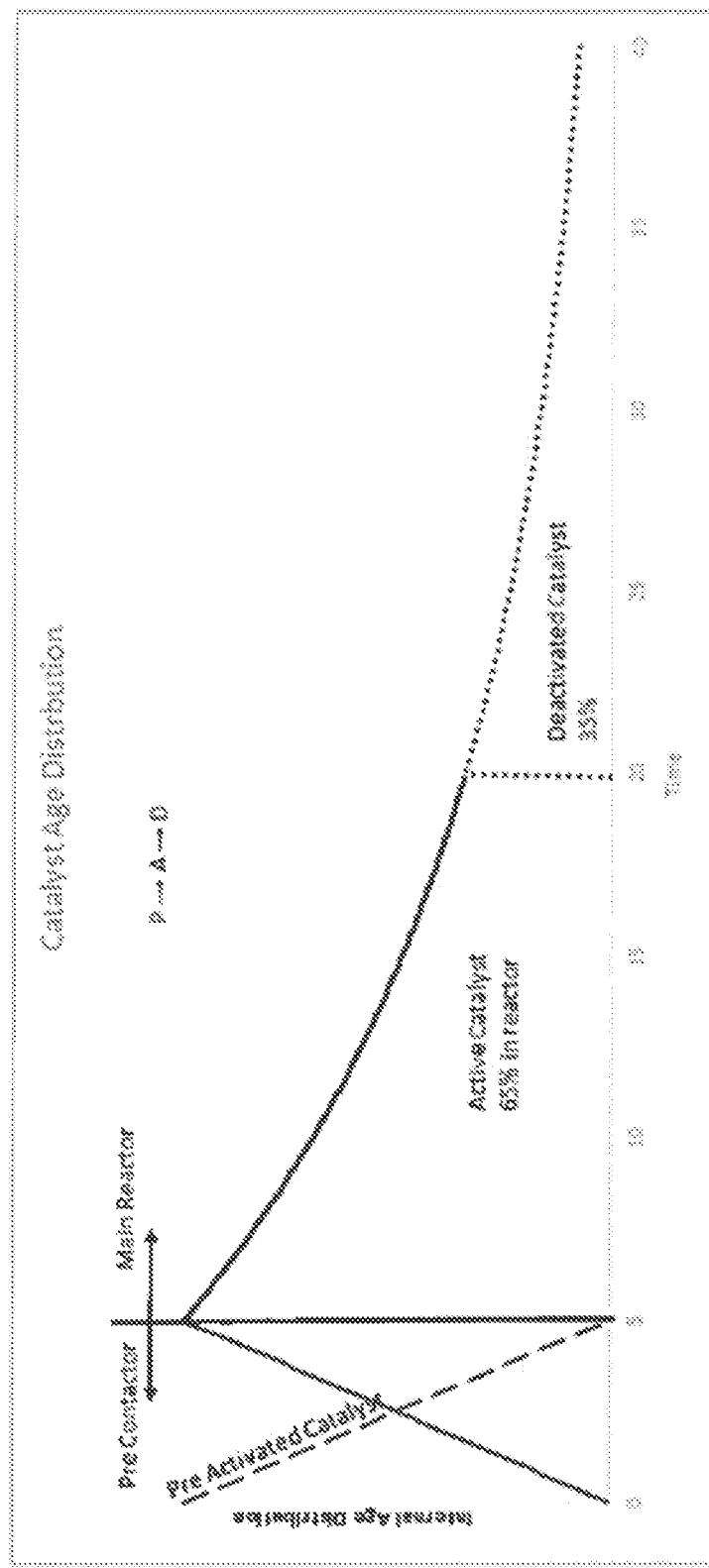
FIG. 6 is a plot illustrating the amount of active catalyst of constructive Example 5 in an ethylene oligomerization reactor with the use of an activation vessel to eliminate the catalyst induction period.

Example 5 is a constructive example that demonstrates the impact of adding an activation vessel prior to an oligomerization reactor. Using a simple pre-catalyst to activated catalyst system to dead catalyst system model and simple CSTR kinetics, a theoretical plot for a catalyst system with an induction period of 5 min is illustrated in FIG. 5. Surprisingly, less than half of the catalyst system (only 41%) is active during the residence time of the reactor. However, if the activation vessel can provide sufficient conditions and residence time to activate the catalyst system before entering the reactor, an increase in active catalyst system can be achieved. The impact of utilizing a catalyst system activation vessel prior to the oligomerization reactor is shown graphically in FIG. 6. Note the significant increase in the amount of active catalyst in the reactor. Elimination of the induction period in the oligomerization reactor results in 65% active catalyst—a significant 59% increase in active catalyst in the reactor. The end result is more productivity (more oligomer product) per amount of chromium (or catalyst), since the catalyst is being used more efficiently, and there is more total active catalyst present in the oligomerization reactor due to the use of an activation vessel.

TABLE 3

Summary of Examples 1-4.

| Example | 1 | 2 | 3 | 4 |
|---|---|---|---|---|
| Solvent | Ethylbenzene | Ethylbenzene | Ethylbenzene | Ethylbenzene |
| Solvent Mass (g) | 1 | 1 | 1 | 1 |
| Diluent | Cyclohexane | Cyclohexane | Cyclohexane | Cyclohexane |
| Diluent Volume (mL) | 200 | 200 | 200 | 200 |
| Complex (mmol) | 0.0053 | 0.0053 | 0.0053 | 0.0053 |
| Chromium (mg) | 0.2767 | 0.2767 | 0.2767 | 0.2767 |
| Al:Cr ratio | 623 | 623 | 623 | 623 |
| Organo-aluminum | MMAO-3A | MMAO-3A | MMAO-20 | MMAO-20 |
| Aging Time (hr) | 1 | 5 | 1 | 1 |
| MAO (g) | 1.275 | 1.275 | 1.275 | 1.275 |
| Reaction Time (min) | 25 | 30 | 20 | 20 |
| $H_2$ Pressure (psig) | 50 | 50 | 50 | 50 |
| Reaction Temperature (° C.) | 90 | 90 | 90 | 90 |
| Ethylene Pressure (psig) | 875 | 875 | 875 | 875 |
| Ethylene Used (g) | 159 | 174 | 171 | 167 |
| Ethylene Conversion (%) | 70 | 57 | 64 | 57 |
| Oligomer Product | | | | |
| Polymer Product (g) | 1.9 | 3.1 | 3.3 | 2.2 |
| Liquid NAO Product (g) | 109 | 95 | 107 | 93 |
| Polymer (wt. %) | 1.7 | 3.2 | 3.0 | 2.3 |
| Ethylbenzene (wt. %) | 0.9 | 1.0 | 0.9 | 1.1 |
| C# dist data (wt. %) | | | | |
| $C_6$ | 40.5 | 41.8 | 38.1 | 40.3 |
| $C_8$ | 40.6 | 49.2 | 46.5 | 50.1 |
| $C_{10}$ | 1.9 | 2.6 | 2.2 | 2.3 |
| $C_{12}$ | 17.0 | 6.4 | 13.3 | 7.3 |
| $C_{14+}$ | 0.0 | 0.0 | 0.0 | 0.0 |
| ($C_6 + C_8$) | 81.1 | 90.9 | 84.5 | 90.4 |
| $C_6$ Purity | 85.36 | 84.93 | 83.68 | 83.80 |
| Methyl-cyclopentane | 6.42 | 6.80 | 7.17 | 7.17 |
| Methylenecyclopentane | 6.49 | 6.88 | 7.10 | 7.14 |
| $C_8$ Purity | 96.15 | 96.11 | 95.93 | 95.93 |
| 1-Octene (wt. %) | 39.05 | 47.24 | 44.56 | 48.09 |
| 1-Hexene (wt. %) | 34.54 | 35.48 | 31.87 | 33.77 |
| Productivities | | | | |
| kg($C_6 + C_8$)/ (g Cr) | 319 | 314 | 325 | 304 |
| kg($C_6 + C_8$)/ (g Cr)/hr | 767 | 627 | 976 | 912 |
| kg($C_6 + C_8$)/ (g Complex) | 35 | 35 | 36 | 34 |

The disclosure refers to numerous aspects and specific examples. Many variations will suggest themselves to those skilled in the art in light of the above detailed description. All such obvious variations are within the full intended scope of the appended claims. Other statements of the disclosure can include, but are not limited to, the following (statements are described as "comprising" but, alternatively, can "consist essentially of" or "consist of"):

Statement 1. A process comprising:
a) forming a first mixture in an activation vessel, the first mixture comprising:
1) ethylene,
2) a catalyst system comprising i) a heteroatomic ligand chromium compound complex and an organoaluminum compound, or ii) a heteroatomic ligand, a chromium compound, and an organoaluminum compound,
3) optionally, a first organic reaction medium, and
4) optionally, hydrogen;
b) maintaining the first mixture in the activation vessel for an average residence time;
c) introducing into a reaction zone:
i) ethylene,
ii) the first mixture from step b),
iii) a second organic reaction medium, and
iv) optionally, hydrogen; and
d) forming an oligomer product in the reaction zone;
wherein the average residence time of the first mixture in the activation vessel is in a range from 10 sec up to a period of time
i) sufficient to form an amount of a first oligomer product in the activation vessel equal to 5% of an amount of the oligomer product formed in the reaction zone; or
ii) where a conversion of ethylene in the activation vessel is equal to 5 mol % of a total ethylene utilized in step a) and step c); or
iii) where a catalyst system productivity in the activation vessel is equal to 5% of a catalyst system mixture productivity in the reaction zone; or iv) where a fouling rate in the activation vessel is equal to 0.065 mg/cm²-hr; or
v) where an oligomer product discharge rate from the activation vessel is equal to 0.15 lb/gal/hr, and an oligomer product discharge rate from the reaction zone is in a range from 0.75 to 6 lb/gal/hr; or
vi) where a ΔT from the inlet of the activation vessel to the outlet of the activation vessel is equal to 5° C.; or
vii) of 8 hr; or
viii) any combination thereof; or
wherein an amount of ethylene introduced into the activation vessel is less than 50% of an amount of ethylene introduced into the reaction zone; or
wherein step b) is performed at an activation temperature and an activation pressure, and the first mixture in the activation vessel is below the bubble point at the activation temperature and the activation pressure; or
any combination thereof.

Statement 2. The process defined in statement 1, wherein, in step a), a first feed stream comprising ethylene and at least a portion of the first organic reaction medium is introduced into the activation vessel separate from a catalyst system mixture comprising the catalyst system.

Statement 3. The process defined in statement 1 or 2, wherein i) the heteroatomic ligand chromium compound complex and the organoaluminum compound are, or ii) at least one of the heteroatomic ligand, the chromium compound, and the organoaluminum compound is, separately introduced into the activation vessel.

Statement 4. The process defined in statement 1 or 2, wherein a catalyst system mixture comprising i) the heteroatomic ligand chromium compound complex and the organoaluminum compound, or ii) the heteroatomic ligand, the chromium compound, and the organoaluminum compound, and optionally at least a portion of the first organic reaction medium, is formed and then introduced into the activation vessel.

Statement 5. The process defined in statement 4, wherein the catalyst system mixture is aged for any suitable period of time in the substantial absence of ethylene prior to introducing the catalyst system mixture into the activation vessel.

Statement 6. A process comprising:
a) forming a first mixture in an activation vessel, the first mixture comprising:
1) a first catalyst system comprising i) a first heteroatomic ligand chromium compound complex and a first organoaluminum compound, or ii) a first heteroatomic ligand, a first chromium compound, and a first organoaluminum compound,
2) a first feed comprising ethylene, a second catalyst system comprising i) a second heteroatomic ligand chromium compound complex and a second organoaluminum compound, or ii) a second heteroatomic ligand, a second chromium compound, and a second organoaluminum compound, a second organic reaction medium, a second oligomer product, and optionally hydrogen,
3) optionally, a first organic reaction medium, and
4) optionally, hydrogen;
b) maintaining the first mixture in the activation vessel for an average residence time;
c) introducing into a reaction zone:
i) ethylene,
ii) the first mixture from step b),
iii) the second organic reaction medium, and
iv) optionally, hydrogen; and
d) forming an oligomer product in the reaction zone;

wherein a portion of a reaction zone effluent is fed to the activation vessel as the first feed, and
wherein the average residence time of the first mixture in the activation vessel is in a range from 10 sec up to a period of time
i) sufficient to form an amount of a first oligomer product in the activation vessel equal to 5% of an amount of the oligomer product formed in the reaction zone; or
ii) where a conversion of ethylene in the activation vessel is equal to 5 mol % of a total ethylene utilized in step a) and step c); or
iii) where a catalyst system productivity in the activation vessel is equal to 5% of a catalyst system mixture productivity in the reaction zone; or
iv) where a fouling rate in the activation vessel is equal to 0.065 mg/cm²-hr; or
v) where an oligomer product discharge rate from the activation vessel is equal to 0.15 lb/gal/hr, and an oligomer product discharge rate from the reaction zone is in a range from 0.75 to 6 lb/gal/hr; or
vi) where a ΔT from the inlet of the activation vessel to the outlet of the activation vessel is equal to 5° C.; or
vii) of 8 hr; or
viii) any combination thereof; or
wherein an amount of ethylene introduced into the activation vessel is less than 50% of an amount of ethylene introduced into the reaction zone; or
wherein step b) is performed at an activation temperature and an activation pressure, and the first mixture in the activation vessel is below the bubble point at the activation temperature and the activation pressure; or
any combination thereof.

Statement 7. The process defined in statement 6, wherein, in step a), a first feed stream comprising ethylene and at least a portion of the first organic reaction medium is introduced into the activation vessel separate from a catalyst system mixture comprising the first catalyst system.

Statement 8. The process defined in statement 6 or 7, wherein i) the first heteroatomic ligand chromium compound complex and the first organoaluminum compound are, or ii) at least one of the first heteroatomic ligand, the first chromium compound, and the first organoaluminum compound is, separately introduced into the activation vessel.

Statement 9. The process defined in statement 6 or 7, wherein a catalyst system mixture comprising i) the first heteroatomic ligand chromium compound complex and the first organoaluminum compound, or ii) the first heteroatomic ligand, the first chromium compound, and the first organoaluminum compound, and optionally at least a portion of the first organic reaction medium, is formed and then introduced into the activation vessel.

Statement 10. The process defined in statement 9, wherein the catalyst system mixture is aged for any suitable period of time in the substantial absence of ethylene prior to introducing the catalyst system mixture into the activation vessel.

Statement 11. The process defined in any one of statements 6-10, wherein, in step c), the ethylene introduced into the reaction zone is substantially devoid of catalyst system or catalyst system components.

Statement 12. The process defined in any one of statements 1-11, wherein, in step c), the ethylene and the first mixture from step b) are introduced separately into the reaction zone.

Statement 13. The process defined in any one of statements 1-11, wherein, in step c), a second feed stream comprising ethylene, at least a portion of the second organic reaction medium, and optionally hydrogen is introduced into the reaction zone separate from the first mixture from step b).

Statement 14. The process defined in any one of the preceding statements, wherein the amount of a first oligomer product in the activation vessel is less than or equal to 5% (or any or value or range disclosed herein, e.g., less than or equal to 4%, 3%, 2%, or 1%) of the amount of the oligomer product formed in the reaction zone.

Statement 15. The process defined in any one of the preceding statements, wherein the conversion of ethylene in the activation vessel is less than or equal to 5 mol % (or in any range of molar ratios disclosed herein, e.g., less than or equal to 4 mol %, less than or equal to 3%, less than or equal to 2%, etc.) of the total ethylene utilized in step a) and step c).

Statement 16. The process defined in any one of the preceding statements, wherein the catalyst system productivity in the activation vessel is less than or equal to 5% (or in any range disclosed herein, e.g., less than or equal to 4%, less than or equal to 3%, less than or equal to 2%, etc.) of the catalyst system mixture productivity in the reaction zone.

Statement 17. The process defined in any one of the preceding statements, wherein the fouling rate in the activation vessel is less than or equal to 0.065 mg/cm$^2$-hr, or in any range of fouling rates disclosed herein, e.g., less than or equal to 0.06 mg/cm$^2$-hr, less than or equal to 0.055 mg/cm$^2$-hr, less than or equal to 0.05 mg/cm$^2$-hr, etc.

Statement 18. The process defined in any one of the preceding statements, wherein the oligomer product discharge rate from the activation vessel is less than or equal to 0.15 lb/gal/hr, or in any range of any oligomer product discharge rate from the activation vessel disclosed herein, e.g., less than or equal to 0.125 lb/gal/hr, less than or equal to 0.1 lb/gal/hr, less than or equal to 0.075 lb/gal/hr, etc.

Statement 19. The process defined in any one of the preceding statements, wherein the oligomer product discharge rate from the reaction zone is in a range from 0.75 to 6 lb/gal/hr, or in any range of any oligomer product discharge rate from the reaction zone disclosed herein, e.g., 0.75 to 6 lb/gal/hr, 1 to 6 lb/gal/hr, 1.2 to 5.5 lb/gal/hr, 1.4 to 5 lb/gal/hr, 1.5 to 4.5 lb/gal/hr, or 1.6 to 4.25 lb/gal/hr, etc.

Statement 20. The process defined in any one of the preceding statements, wherein a $\Delta T$ from the inlet of the activation vessel to the outlet of the activation vessel is less than or equal to 5° C. (or any other value disclosed herein, e.g., less than or equal to 4° C., 3° C., 2° C., or 1° C.).

Statement 21. The process defined in any one of the preceding statements, wherein the average residence time is less than or equal to 8 hr (or any time or any range disclosed herein, e.g., less than or equal to 6 hr, 4 hr, 2 hr, 1 hr, less than or equal to 45 min, less than or equal to 30 min, less than or equal to 20 min, or less than or equal to 15 min, or in a range from 10 sec to 45 min, from 10 sec to 30 min, from 30 sec to 20 min, from 1 min to 30 min, or from 2 min to 15 min).

Statement 22. The process defined in any one of the preceding statements, wherein the amount of ethylene introduced into the activation vessel is less than or equal to 50% (or in any range disclosed herein, e.g., less than or equal to 40%, less than or equal to 30%, less than or equal to 25%, etc.) of the amount of ethylene introduced into the reaction zone.

Statement 23. The process defined in any one of the preceding statements, wherein:

step b) is performed at the activation temperature and the activation pressure; and the first mixture in the activation vessel is below the bubble point at the activation temperature and the activation pressure.

Statement 24. The process defined in any one of the preceding statements, wherein hydrogen is present in step a).

Statement 25. The process defined in any one of the preceding statements, wherein hydrogen is present in step c).

Statement 26. A reaction system comprising:

(a) an activation vessel configured to form a first mixture, wherein the activation vessel is further configured for an average residence time of the first mixture in the activation vessel;

(b) one or more activation vessel inlets configured to introduce i) ethylene and a catalyst system mixture, or ii) ethylene and components of a catalyst system mixture, into the activation vessel;

(c) an activation vessel outlet configured to withdraw the first mixture from the activation vessel;

(d) a reaction zone configured to contact ethylene, the first mixture, a second organic reaction medium, and optionally hydrogen to form an oligomer product;

(e) one or more reaction zone inlets configured to introduce ethylene, the second organic reaction medium, and the first mixture from the activation vessel outlet into the reaction zone; and (f) a reaction zone outlet configured to withdraw a reaction zone effluent stream containing the oligomer product from the reaction zone;

wherein the average residence time of the first mixture in the activation vessel is in a range from 10 sec up to a period of time i) sufficient to form an amount of a first oligomer product in the activation vessel equal to 5% of an amount of the oligomer product formed in the reaction zone; or ii) where a conversion of ethylene in the activation vessel is equal to 5 mol % of a total ethylene utilized in step a) and step c); or iii) where a catalyst system productivity in the activation vessel is equal to 5% of a catalyst system mixture productivity in the reaction zone; or iv) where a fouling rate in the activation vessel is equal to 0.065 mg/cm$^2$-hr; or v) where an oligomer product discharge rate from the activation vessel is equal to 0.15 lb/gal/hr and an oligomer product discharge rate from the reaction zone is in a range from 0.75 to 6 lb/gal/hr; or vi) where a $\Delta T$ from the inlet of the activation vessel to the outlet of the activation vessel is equal to 5° C.; or vii) of 8 hr; or viii) any combination thereof; or wherein an amount of ethylene introduced into the activation vessel is less than 50% of an amount of ethylene introduced into the reaction zone; or wherein step b) is performed at an activation temperature and an activation pressure, and the first mixture in the activation vessel is below the bubble point at the activation temperature and the activation pressure; or any combination thereof.

Statement 27. The system defined in statement 26, wherein the one or more reaction zone inlets are further configured to introduce hydrogen into the reaction zone.

Statement 28. The system defined in statement 26 or 27, wherein the activation vessel outlet and at least one of the one or more reaction zone inlets are fluidly connected.

Statement 29. The system defined in any one of statements 26-28, wherein the reaction zone effluent stream further comprises ethylene, the second organic reaction medium, the catalyst system mixture, or any combination thereof.

Statement 30. The system defined in any one of statements 26-29, wherein the amount of a first oligomer product in the activation vessel is less than or equal to 5% (or any or value or range disclosed herein, e.g., less than or equal to 4%, 3%, 2%, or 1%) of the amount of the oligomer product formed in the reaction zone.

Statement 31. The system defined in any one of statements 26-30, wherein the activation vessel is further configured for the conversion of ethylene of less than or equal to 5 mol % (or in any range of molar ratios disclosed herein, e.g., less than or equal to 4 mol %, less than or equal to 3%, less than or equal to 2%, etc.) of the total ethylene utilized in the activation vessel and the reaction zone.

Statement 32. The system defined in any one of statements 26-31, wherein the activation vessel is further configured for a catalyst system productivity of less than or equal to 5% (or in any range disclosed herein, e.g., less than or equal to 4%, less than or equal to 3%, less than or equal to 2%, etc.) of a catalyst system mixture productivity in the reaction zone.

Statement 33. The system defined in any one of statements 26-32, wherein the fouling rate in the activation vessel is less than or equal to 0.065 $mg/cm^2$-hr, or in any range of fouling rates disclosed herein, e.g., less than or equal to 0.06 $mg/cm^2$-hr, less than or equal to 0.055 $mg/cm^2$-hr, less than or equal to 0.05 $mg/cm^2$-hr, etc.

Statement 34. The system defined in any one of statements 26-33, wherein the oligomer product discharge rate from the activation vessel is less than or equal to 0.15 lb/gal/hr, or in any range of any oligomer product discharge rate from the activation vessel disclosed herein, e.g., less than or equal to 0.125 lb/gal/hr, less than or equal to 0.1 lb/gal/hr, less than or equal to 0.075 lb/gal/hr, etc.

Statement 35. The system defined in any one of statements 26-34, wherein the oligomer product discharge rate from the reaction zone is in a range from 1 to 6 lb/gal/hr, or in any range of any oligomer product discharge rate from the reaction zone disclosed herein, e.g., 0.75 to 6 lb/gal/hr, 1 to 6 lb/gal/hr, 1.2 to 5.5 lb/gal/hr, 1.4 to 5 lb/gal/hr, 1.5 to 4.5 lb/gal/hr, or 1.6 to 4.25 lb/gal/hr, etc.

Statement 36. The system defined in any one of statements 26-35, wherein the activation vessel is further configured for a $\Delta T$ from the inlet of the activation vessel to the outlet of the activation vessel of less than or equal to 5° C. (or any other value or range disclosed herein, e.g., less than or equal to 4° C., 3° C., 2° C., or 1° C.).

Statement 37. The system defined in any one of statements 26-36, wherein the average residence time is less than or equal to 2 hr (or any time or any range disclosed herein, e.g., less than or equal to 1 hr, less than or equal to 45 min, less than or equal to 30 min, less than or equal to 20 min, or less than or equal to 15 min, or in a range from 10 sec to 45 min, from 10 sec to 30 min, from 30 sec to 20 min, from 1 min to 30 min, or from 2 min to 15 min).

Statement 38. The system defined in any one of statements 26-37, wherein the amount of ethylene introduced into the activation vessel is less than or equal to 50% (or in any range disclosed herein, e.g., less than or equal to 40%, less than or equal to 30%, less than or equal to 25%, etc.) of the amount of ethylene introduced into the reaction zone.

Statement 39. The system defined in any one of statements 26-38, wherein:

the activation vessel is further configured to operate at the activation temperature and the activation pressure; and the first mixture in the activation vessel is below the bubble point at the activation temperature and the activation pressure.

Statement 40. The system defined in any one of statements 26-39, wherein at least one of the one or more activation vessel inlets is further configured to introduce a first organic reaction medium and/or hydrogen into the activation vessel.

Statement 41. The system defined in any one of statements 26-40, wherein the one or more activation vessel inlets are configured to introduce the catalyst system mixture into the activation vessel, wherein the catalyst system mixture comprises (i) a first heteroatomic ligand chromium compound complex and a first organoaluminum compound, or (ii) a first heteroatomic ligand, a first chromium compound, and a first organoaluminum compound.

Statement 42. The system defined in any one of statements 26-40, wherein the one or more activation vessel inlets are configured to introduce the components of the catalyst system mixture into the activation vessel, wherein the components comprise (i) a first heteroatomic ligand chromium compound complex and a first organoaluminum compound, or (ii) a first heteroatomic ligand, a first chromium compound, and a first organoaluminum compound.

Statement 43. The system defined in any one of statements 26-42, wherein the activation vessel is configured to operate batchwise or continuously.

Statement 44. The system defined in any one of statements 26-43, wherein the activation vessel is any suitable vessel or any vessel disclosed herein, e.g., a stirred tank (CSTR), a flow reactor (plug flow), etc.

Statement 45. The system defined in any one of statements 26-44, wherein the reaction system further comprises (g) a controller configured to control the average residence time of the first mixture in the activation vessel, and/or temperature in the activation vessel, and/or pressure in the activation vessel, and/or ethylene conversion in the activation vessel, and/or ethylene flow rate into the activation vessel.

We claim:

1. A process comprising:
    a) forming a first mixture in an activation vessel, the first mixture comprising:
        1) ethylene,
        2) a catalyst system comprising i) a heteroatomic ligand chromium compound complex and an organoaluminum compound, or ii) a heteroatomic ligand, a chromium compound, and an organoaluminum compound,
        3) optionally, a first organic reaction medium, and
        4) optionally, hydrogen;
    b) maintaining the first mixture in the activation vessel for an average residence time;
    c) introducing into a reaction zone:
        i) ethylene,
        ii) the first mixture from step b),
        iii) a second organic reaction medium, and
        iv) optionally, hydrogen; and
    d) forming an oligomer product in the reaction zone;
    wherein the average residence time of the first mixture in the activation vessel is in a range from 10 sec up to a period of time sufficient for a conversion of ethylene in the activation vessel to equal 5 mol % of a total ethylene utilized in step a) and step c).

2. The process of claim 1, wherein:
the first organic reaction medium and the second organic reaction medium comprise cyclohexane;
in step c), the first mixture from step b) and the ethylene are introduced separately into the reaction zone; and
the oligomer product comprises $C_6$ and/or $C_8$ olefins.

3. The process of claim 1, wherein hydrogen is present in step c) and not present in step a).

4. The process of claim 1, wherein the average residence time of the first mixture in the activation vessel is in a range from 1 min up to a period of time sufficient for a conversion of ethylene in the activation vessel to equal 3 mol % of a total ethylene utilized in step a) and step c).

5. The process of claim 4, wherein i) the heteroatomic ligand chromium compound complex and the organoaluminum compound are, or ii) at least one of the heteroatomic ligand, the chromium compound, and the organoaluminum compound is, separately introduced into the activation vessel.

6. The process of claim 4, wherein a catalyst system mixture comprising:
(a) i) the heteroatomic ligand chromium compound complex and the organoaluminum compound, or ii) the heteroatomic ligand, the chromium compound, and the organoaluminum compound, and
(b) a catalyst system organic medium comprising an aromatic hydrocarbon,
is formed and then introduced into the activation vessel.

7. The process of claim 4, wherein, in step c), a second feed stream comprising ethylene, at least a portion of the second organic reaction medium, and hydrogen is introduced into the reaction zone separate from the first mixture from step b).

8. The process of claim 4, wherein the first organic reaction medium and the second organic reaction medium independently comprise a cyclic aliphatic hydrocarbon, an acyclic aliphatic hydrocarbon, an aromatic hydrocarbon, or any combination thereof.

9. The process of claim 4, wherein:
the first organic reaction medium and the second organic reaction medium comprise cyclohexane;
in step c), the first mixture from step b) and the ethylene are introduced separately into the reaction zone; and
the oligomer product comprises $C_6$ and/or $C_8$ olefins.

10. A process comprising:
a) forming a first mixture in an activation vessel, the first mixture comprising:
1) a first catalyst system comprising i) a first heteroatomic ligand chromium compound complex and a first organoaluminum compound, or ii) a first heteroatomic ligand, a first chromium compound, and a first organoaluminum compound,
2) a first feed comprising ethylene, a second catalyst system comprising i) a second heteroatomic ligand chromium compound complex and a second organoaluminum compound, or ii) a second heteroatomic ligand, a second chromium compound, and a second organoaluminum compound, a second organic reaction medium, a second oligomer product, and optionally hydrogen,
3) optionally, a first organic reaction medium, and
4) optionally, hydrogen;
b) maintaining the first mixture in the activation vessel for an average residence time;
c) introducing into a reaction zone:
i) ethylene,
ii) the first mixture from step b),
iii) the second organic reaction medium, and
iv) optionally, hydrogen; and
d) forming an oligomer product in the reaction zone;
wherein a portion of a reaction zone effluent is fed to the activation vessel as the first feed, and
wherein the average residence time of the first mixture in the activation vessel is in a range from 10 sec to 45 min.

11. The process of claim 10, wherein, in step c), a second feed stream comprising ethylene, at least a portion of the second organic reaction medium, and hydrogen is introduced into the reaction zone separate from the first mixture from step b).

12. The process of claim 10, wherein the average residence time is in a range from 30 sec to 45 min.

13. The process of claim 12, wherein, in step a), a first feed stream comprising ethylene and at least a portion of the first organic reaction medium is introduced into the activation vessel separate from a catalyst system mixture comprising the first catalyst system.

14. The process of claim 10, wherein the average residence time is in a range from 1 min to 30 min.

15. The process of claim 14, wherein, in step c), the ethylene and the first mixture from step b) are introduced separately into the reaction zone.

16. The process of claim 14, wherein a catalyst system mixture comprising i) the first heteroatomic ligand chromium compound complex and the first organoaluminum compound, or ii) the first heteroatomic ligand, the first chromium compound, and the first organoaluminum compound, and optionally at least a portion of the first organic reaction medium, is formed and then introduced into the activation vessel.

17. A reaction system comprising:
(a) an activation vessel configured to form a first mixture, wherein the activation vessel is further configured for an average residence time of the first mixture in the activation vessel;
(b) one or more activation vessel inlets configured to introduce i) ethylene and a catalyst system mixture, or ii) ethylene and components of a catalyst system mixture, into the activation vessel;
(c) an activation vessel outlet configured to withdraw the first mixture from the activation vessel;
(d) a reaction zone configured to contact ethylene, the first mixture, a second organic reaction medium, and optionally hydrogen to form an oligomer product;
(e) one or more reaction zone inlets configured to introduce ethylene, the second organic reaction medium, and the first mixture from the activation vessel outlet into the reaction zone; and
(f) a reaction zone outlet configured to withdraw a reaction zone effluent stream containing the oligomer product from the reaction zone;
(g) a controller configured to control the average residence time of the first mixture in the activation vessel, and/or a temperature in the activation vessel, and/or a pressure in the activation vessel, and/or an ethylene conversion in the activation vessel, and/or an amount of ethylene introduced into the activation vessel;
wherein the average residence time of the first mixture in the activation vessel is in a range from 10 sec up to a period of time sufficient to form an amount of a first oligomer product in the activation vessel equal to 5% of an amount of the oligomer product formed in the reaction zone; and
wherein the activation vessel is a stirred tank.

18. The reaction system of claim 17, wherein the activation vessel is further configured for a conversion of ethylene in the activation vessel that is less than or equal to 5 mol % of a total ethylene utilized in the activation vessel and the reaction zone.

19. A reaction system comprising:

(a) an activation vessel configured to form a first mixture, wherein the activation vessel is further configured for an average residence time of the first mixture in the activation vessel;

(b) one or more activation vessel inlets configured to introduce i) ethylene and a catalyst system mixture, or ii) ethylene and components of a catalyst system mixture, into the activation vessel;

(c) an activation vessel outlet configured to withdraw the first mixture from the activation vessel;

(d) a reaction zone configured to contact ethylene, the first mixture, a second organic reaction medium, and optionally hydrogen to form an oligomer product;

(e) one or more reaction zone inlets configured to introduce ethylene, the second organic reaction medium, and the first mixture from the activation vessel outlet into the reaction zone; and (f) a reaction zone outlet configured to withdraw a reaction zone effluent stream containing the oligomer product from the reaction zone;

(g) a controller configured to control the average residence time of the first mixture in the activation vessel, and/or a temperature in the activation vessel, and/or a pressure in the activation vessel, and/or an ethylene conversion in the activation vessel, and/or an amount of ethylene introduced into the activation vessel;

wherein the average residence time of the first mixture in the activation vessel is in a range from 30 sec to 45 min; and wherein the activation vessel is a stirred tank.

20. The reaction system of claim 19, wherein the average residence time is in a range from 2 min to 15 min.

21. The reaction system of claim 19, wherein the average residence time is in a range from 1 min to 30 min.

* * * * *